(12) United States Patent
Boock et al.

(10) Patent No.: US 11,471,081 B2
(45) Date of Patent: Oct. 18, 2022

(54) CONTINUOUS GLUCOSE MONITORING DEVICE

(71) Applicant: Zense-Life Inc., Carlsbad, CA (US)

(72) Inventors: Robert James Boock, Carlsbad, CA (US); Jocelyn Lo, Poway, CA (US); Paul Smith, Poway, CA (US)

(73) Assignee: Zense-Life Inc., Carlsbad, CA (US)

( * ) Notice: Subject to any disclaimer, the term of this patent is extended or adjusted under 35 U.S.C. 154(b) by 806 days.

(21) Appl. No.: 16/375,895

(22) Filed: Apr. 5, 2019

(65) Prior Publication Data

US 2019/0307381 A1    Oct. 10, 2019

Related U.S. Application Data

(60) Provisional application No. 62/653,821, filed on Apr. 6, 2018.

(51) Int. Cl.
*A61B 5/00* (2006.01)
*A61B 5/1486* (2006.01)
(Continued)

(52) U.S. Cl.
CPC ........ *A61B 5/14865* (2013.01); *A61B 5/0002* (2013.01); *A61B 5/14532* (2013.01); *A61B 5/4839* (2013.01); *A61B 5/6823* (2013.01); *A61B 5/6824* (2013.01); *A61B 5/024* (2013.01); *A61B 5/1072* (2013.01); *A61B 5/1468* (2013.01);
(Continued)

(58) Field of Classification Search
CPC ............ A61B 5/14865; A61B 5/14532; A61B 5/1468
See application file for complete search history.

(56) References Cited

U.S. PATENT DOCUMENTS 4,440,175 A    4/1984   Wilkins
8,414,750 B2   4/2013   Heller et al.
(Continued)

FOREIGN PATENT DOCUMENTS

EP    0649628 A1    4/1995
EP    2017607 B1   10/2012
(Continued)

OTHER PUBLICATIONS

International Search Report dated Oct. 29, 2019 for PCT Patent Application No. PCT/US2019/026028.
(Continued)

*Primary Examiner* — Christian Jang
(74) *Attorney, Agent, or Firm* — MLO, a professional corp.

(57) ABSTRACT

An apparatus includes a body and an actuator is coupled to the body. A needle is mounted to the actuator. The needle comprises a slot along a length to a tip. A sensor is coupled to a plurality of wires. A base is configured to be moveable by the actuator and includes a cutout, a circuit board having a microprocessor, and a plurality of contacts. Each contact is coupled to a wire of the plurality of wires. A power source is connected to the circuit board and to the base. A bracket is coupled to the bottom surface of the body and configured to receive the base. A patch is coupled to the bracket and has an adhesive. A needle is configured to be moveable by the actuator. The plurality of wires extend from the circuit board of the base, through the needle and out of the slot.

16 Claims, 42 Drawing Sheets

(51) Int. Cl.
*A61B 5/145* (2006.01)
*A61B 5/1468* (2006.01)
*A61B 5/024* (2006.01)
*A61B 5/107* (2006.01)
*A61B 5/16* (2006.01)
*A61B 10/00* (2006.01)

(52) U.S. Cl.
CPC .............. *A61B 5/165* (2013.01); *A61B 5/442* (2013.01); *A61B 5/443* (2013.01); *A61B 5/444* (2013.01); *A61B 5/4806* (2013.01); *A61B 5/4866* (2013.01); *A61B 5/4872* (2013.01); *A61B 5/6848* (2013.01); *A61B 10/0012* (2013.01)

(56) References Cited

U.S. PATENT DOCUMENTS

| | | | |
|---|---|---|---|
| 8,906,210 | B2 | 12/2014 | Curry |
| 2003/0129314 | A1 | 7/2003 | Russell et al. |
| 2003/0217966 | A1 | 11/2003 | Tapsak et al. |
| 2007/0027385 | A1 | 2/2007 | Brister et al. |
| 2007/0197889 | A1 | 8/2007 | Brister et al. |
| 2007/0197890 | A1 | 8/2007 | Boock et al. |
| 2008/0279909 | A1 | 11/2008 | Cleek et al. |
| 2009/0062767 | A1 | 3/2009 | Antwerp et al. |
| 2009/0203978 | A1 | 8/2009 | Say et al. |
| 2009/0247856 | A1 | 10/2009 | Boock et al. |
| 2010/0025238 | A1* | 2/2010 | Gottlieb ............. A61B 5/14532 204/403.01 |
| 2010/0270175 | A1 | 10/2010 | Pei et al. |
| 2011/0027458 | A1 | 2/2011 | Boock et al. |
| 2011/0028815 | A1 | 2/2011 | Simpson et al. |
| 2011/0144465 | A1 | 6/2011 | Shults et al. |
| 2011/0230735 | A1 | 9/2011 | Wolfe et al. |
| 2014/0305804 | A1 | 10/2014 | Madangopal et al. |
| 2014/0348703 | A1 | 11/2014 | Thomas et al. |
| 2014/0367246 | A1 | 12/2014 | Shah et al. |
| 2015/0025346 | A1 | 1/2015 | Simpson et al. |
| 2015/0122645 | A1 | 5/2015 | Yang et al. |
| 2015/0122647 | A1 | 5/2015 | Shah et al. |
| 2015/0366493 | A1 | 12/2015 | Cremers |
| 2017/0164881 | A1 | 6/2017 | Fujita et al. |
| 2017/0188916 | A1 | 7/2017 | Wang et al. |
| 2017/0290512 | A1 | 10/2017 | Antonio et al. |
| 2017/0325723 | A1* | 11/2017 | Larson ............... A61B 5/14532 |
| 2018/0094290 | A1 | 4/2018 | Feldman et al. |
| 2019/0310218 | A1 | 10/2019 | Boock et al. |
| 2019/0310219 | A1 | 10/2019 | Boock |
| 2019/0320947 | A1 | 10/2019 | Chen et al. |
| 2020/0196924 | A1 | 6/2020 | Brister |

FOREIGN PATENT DOCUMENTS

| | | |
|---|---|---|
| WO | 2016049243 A1 | 3/2016 |
| WO | 2018107168 A1 | 6/2018 |

OTHER PUBLICATIONS

Notice of Allowance and Fees dated Oct. 20, 2021 for U.S. Appl. No. 16/375,887.
C. Saby et al: "Glucose sensor based on carbon paste electrode incorporating poly(ethylene glycol)—modified glucose oxidase and various mediators", Analytica Chimica Acta, vol. 304, No. 1, Mar. 1, 1995 (Mar. 1, 1995) pp. 33-39, XP055646277, Amsterdam, NL ISSN: 0003-2670, DOI:10.1016/0003-2670(94)00545-W.
Extended European Search Report dated Dec. 15, 2021 for European Patent Office Patent Application No. 19782061.6.
International Search Report and Written Opinion dated Jan. 3, 2022 for PCT Patent Application No. PCT/IB2021/058968.
International Search Report and Written Opinion dated Jan. 4, 2022 for PCT Patent Application No. PCT/IB2021/059023.
International Search Report and Written Opinion dated Oct. 21, 2021 for PCT Patent Application No. PCT/IB2021/054938.
Notice of Allowance and Fees dated Jun. 8, 2021 for U.S. Appl. No. 16/375,884.
Notice of Allowance dated Apr. 14, 2021 for U.S. Appl. No. 16/375,880.
Office Action dated Apr. 27, 2021 for U.S. Appl. No. 16/375,887.
Office Action dated Feb. 8, 2021 for U.S. Appl. No. 16/375,884.
Office Action dated Jan. 21, 2021 for U.S. Appl. No. 16/375,887.
Restriction Requirement dated Dec. 30, 2020 for U.S. Appl. No. 16/375,880.
Shin, J. et al., Potentiometric biosensors using immobilized enzyme layers mixed with hydrophilic polyurethane, Sensors and Actuators B 50, Mar. 24, 1998, 8 pgs, Elsevier, Korea.
Continuous Glucose Monitoring System, Freestyle Libre System, Abbott Laboratories, Oct. 2018, 4 pages, Accessed Online on Mar. 22, 2019, https://www.freestylelibre.us/.
MiniMed 670G Insulin Pump System, Medtronic Diabetes, 2018, 6 pages, Accessed Online on Mar. 22, 2019, https://www.medtronicdiabetes.com/products/minimed-670g-insulin-pump-system.
Richardo Tucceri, "Non-Conducting Poly(O-Aminophenol) Films in the Field of the Bioelectrochemistry," American Journal of Analytical Chemistry, 2013, 4, 13-26, http://dx.doi.org/10.4236/ajac.2013.46A003 Published Online Jun. 2013 (http://www.scirp.org/journal/ajac).
Screen-Printed Carbon Electrodes, DropSens, 2 pages, Accessed on Mar. 15, 2018.
The Dexcom G5 Mobile CGM System, Dexcom, 2009, 22 pages, Accessed Online on Mar. 22, 2019. https://www.dexcom.com/g5-mobile-cgm.
International Search Report dated Jul. 30, 2019 for PCT Patent Application No. PCT/US2019/025962.
European Search Report dated Jan. 28, 2022 for European Patent Application No. 19780733.2.
International Search Report and Written Opinion dated Mar. 8, 2022 for PCT Patent Application No. PCT/IB2021/061432.
Office Action dated Apr. 12, 2022 for U.S. Appl. No. 16/375,891.
Office Action dated Apr. 14, 2022 for U.S. Appl. No. 16/375,877.
Office Action dated May 9, 2022 for U.S. Appl. No. 16/375,873.
Notice of Allowance and Fees dated Aug. 3, 2022 for U.S. Appl. No. 16/375,891.
Office Action dated Aug. 4, 2022 for U.S. Appl. No. 16/375,875.
Spyropoulos et al., "Fabrication and Utilization of Bifunctional Protein/Polysaccharide Coprecipitates for the Independent Codelivery of Two Model Actives from Simple Oil-in-Water Emulsions", Langmuir, Mar. 2018, vol. 34, pp. 3934-3948 (Year: 2018).
Tucceri et al., "Electrosynthesis and Spectroscopic Characterization of Poly-o-Aminophenol) Film Electrodes", International Scholarly Research Notices, May 15, 2012, vol. 2012, Article ID 942920, 26 pages. (Year: 2012).

* cited by examiner

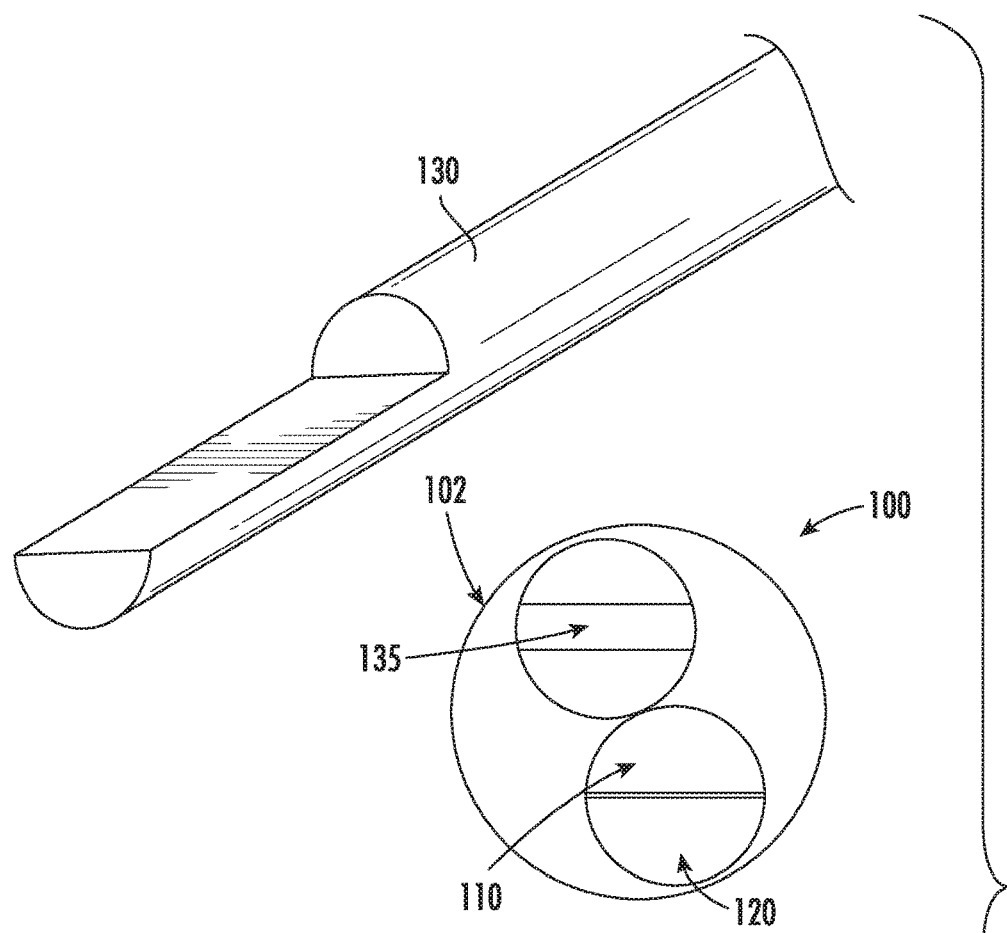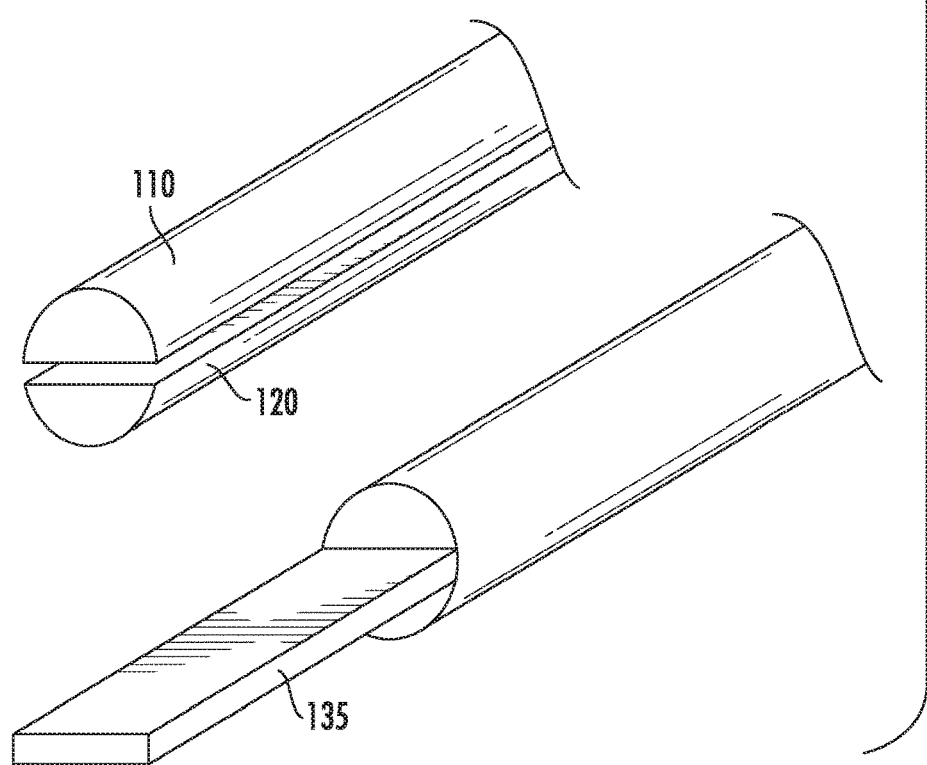
FIG. 1

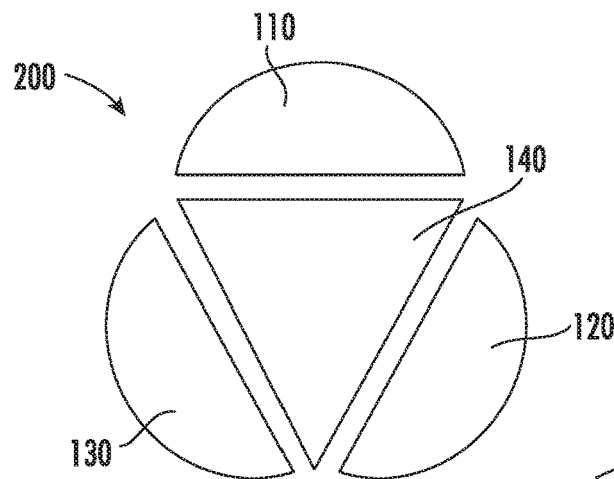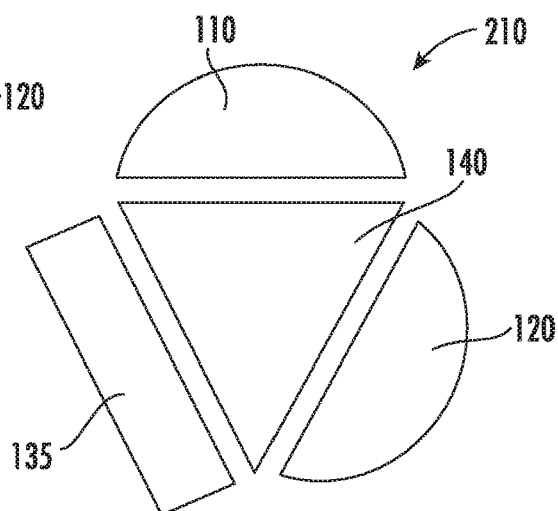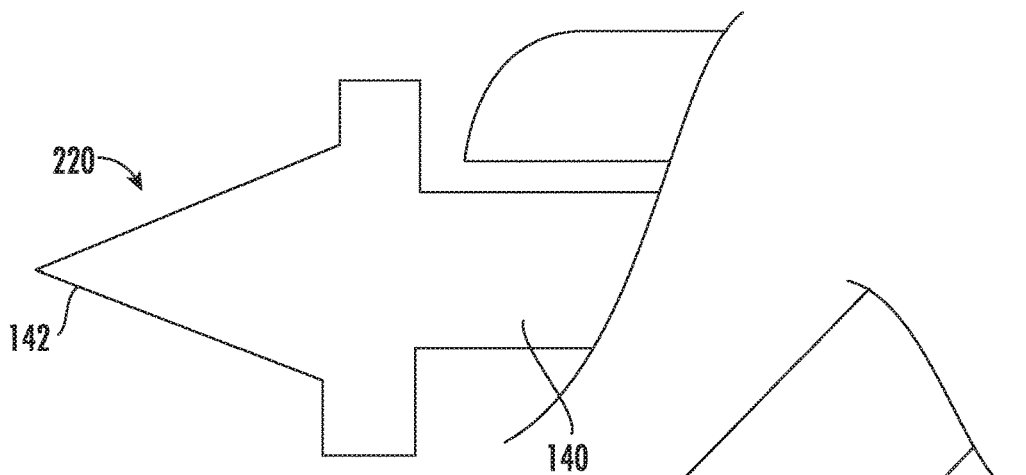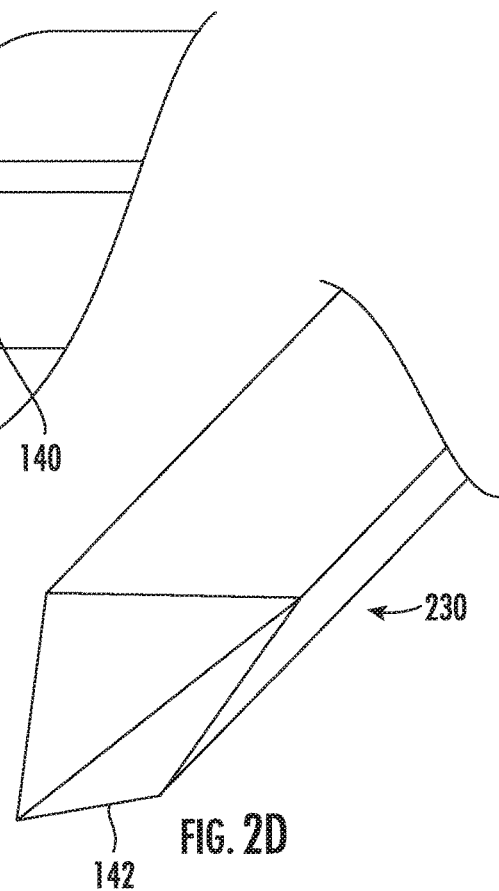

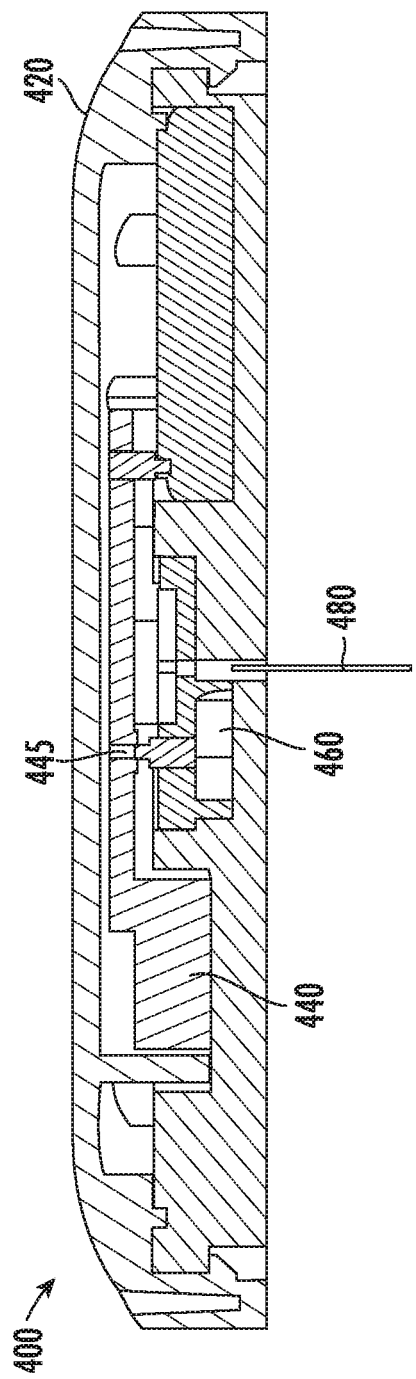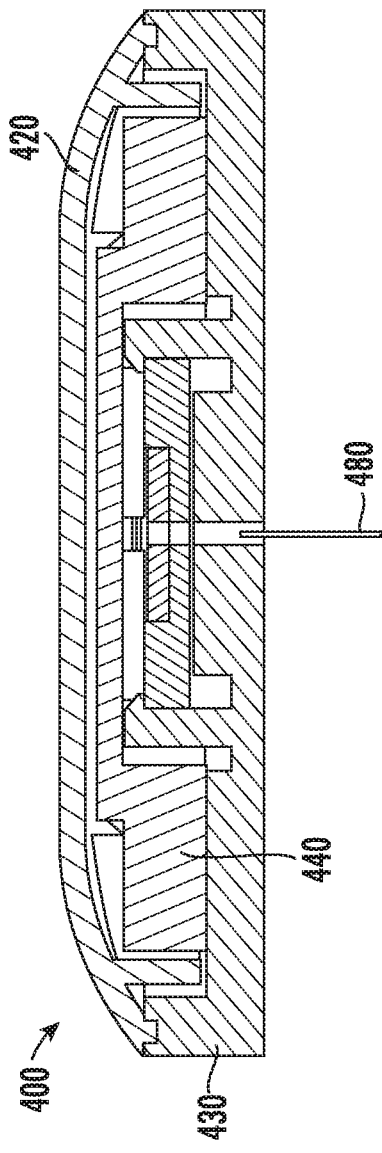

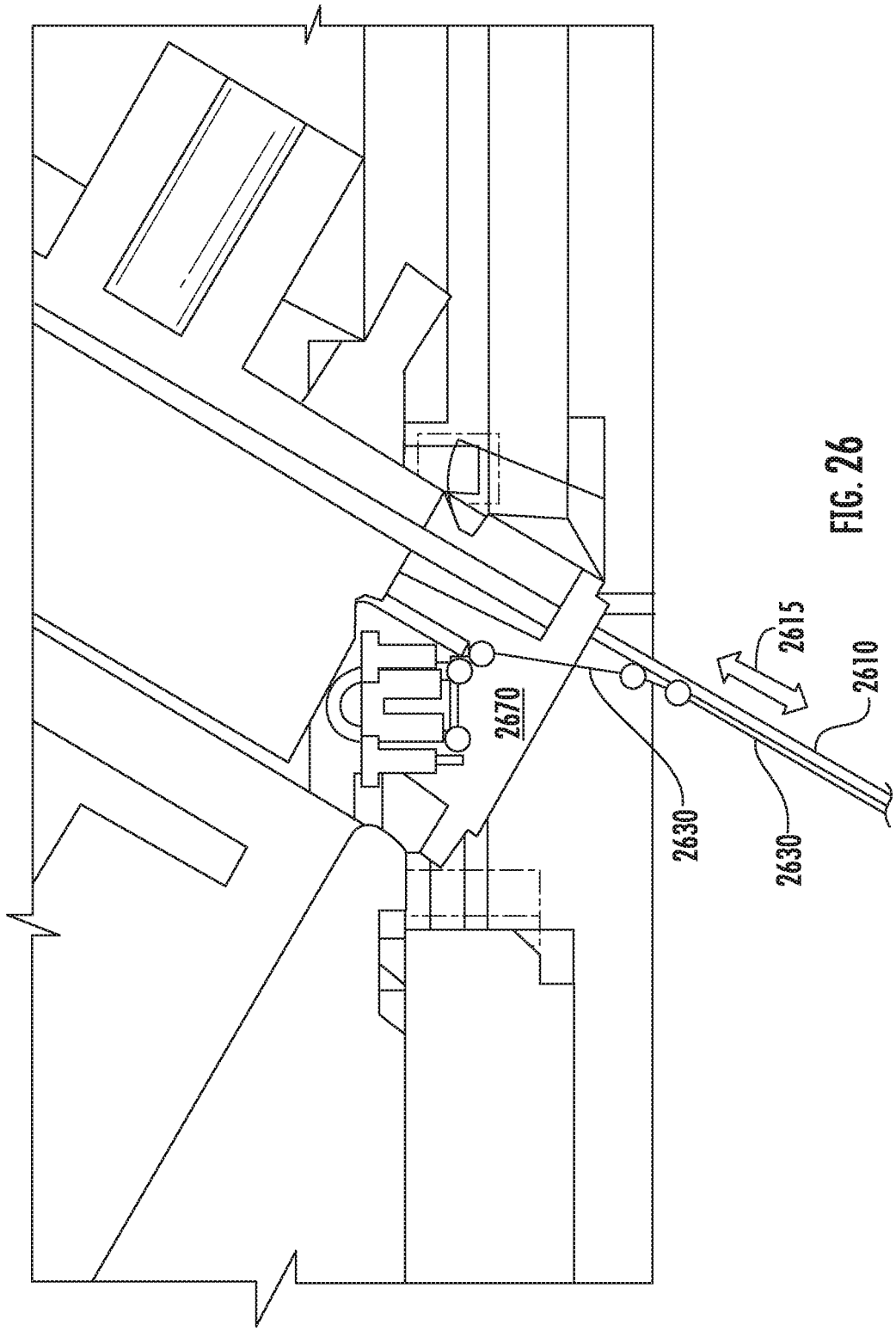

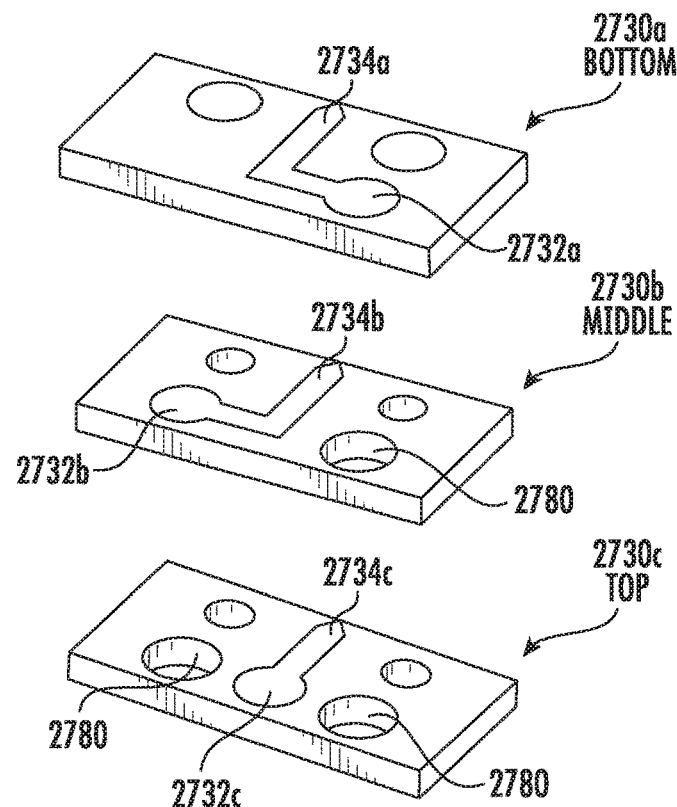
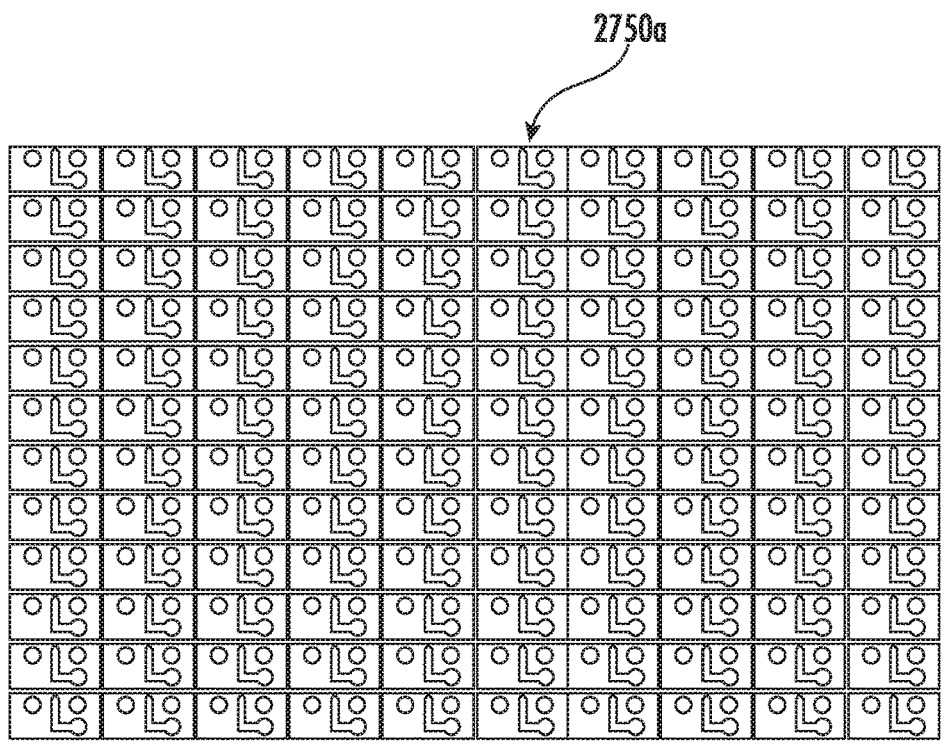
FIG. 27

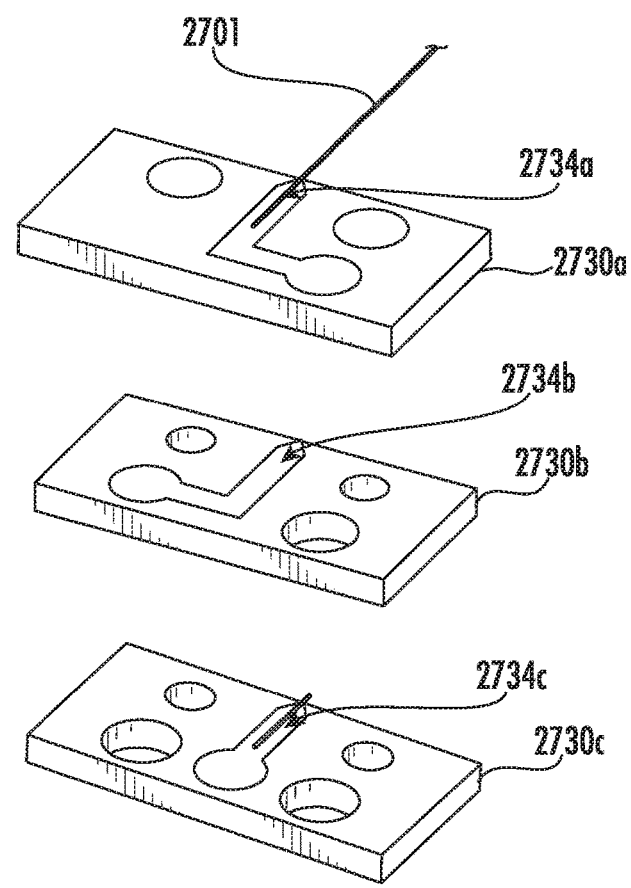
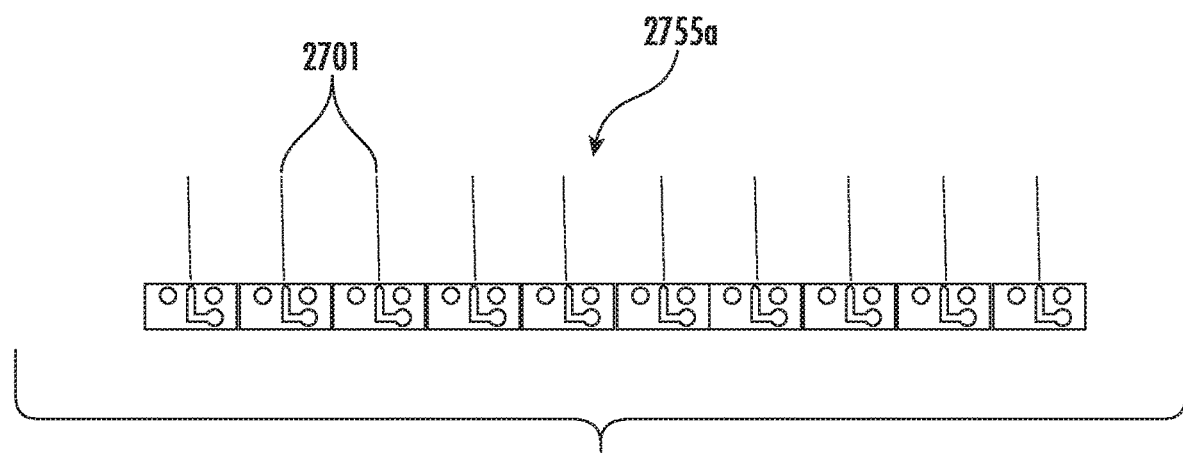
FIG. 28

2701

4200

4120
COUPLING A SENSOR TO A PLURALITY OF WIRES WHEREIN THE SENSOR AND THE PLURALITY OF WIRES BEING SIZED TO FIT TRHOUGH THE INNER DIAMETER OF THE NEEDLE

4220
COUPLING A WIRE OF THE PLURALITY OF WIRES TO A CONTACT OF THE PLURALITY OF CONTACTS, EACH CONTACT HAVING AN OPENING OF A PLURALITY OF OPENINGS ON A CIRCUIT BOARD, THE OPENING HAVING A METAL COATING

4230
ATTACHING A FASTENER HAVING A PROTRUSION INTO THE OPENING, WHEREIN A DIAMETER OF THE PROTRUSION IS LESS THAN A DIAMETER OF THE OPENING, AND WHEREIN THE WIRE OF THE PLURALITY OF WIRES IS BETWEEN THE OPENING AND THE PROTRUSION

4240
CONNECTING A POWER SOURCE TO THE CIRCUIT BOARD

4250
ASSEMBLING THE CIRCUIT BOARD AND POWER SOURCE IN A BASE

FIG. 42

CONTINUOUS GLUCOSE MONITORING DEVICE

RELATED APPLICATIONS

This application claims priority to U.S. Provisional Patent Application No. 62/653,821 filed on Apr. 6, 2018 and entitled "Continuous Glucose Monitoring Device," which is hereby incorporated by reference in full.

BACKGROUND

Monitoring of glucose levels is critical for diabetes patients. Continuous glucose monitoring (CGM) sensors are a type of device in which glucose is measured from fluid sampled in an area just under the skin multiple times a day. CGM devices are administered with an applicator and typically involve a small housing in which the electronics are located and which is adhered to the patient's skin to be worn for a period of time. A small needle within the device delivers the subcutaneous sensor which is often electrochemical.

Electrochemical glucose sensors operate by using electrodes which typically detect an amperometric signal caused by oxidation of enzymes during conversion of glucose to gluconolactone. The amperometric signal can then be correlated to a glucose concentration. Two-electrode (also referred to as 2-pole) designs use a working electrode and a reference electrode, where the reference electrode provides a reference against which the working electrode is compared. Three-electrode (or 3-pole) designs have a working electrode, a reference electrode and a counter electrode. The counter electrode replenishes ionic loss at the reference electrode and is part of the ionic circuit.

Glucose readings taken by the sensor can be tracked and analyzed by a monitoring device, such as by scanning the sensor with a customized receiver or by transmitting signals directly from the monitoring device to a device such as a smartphone or computer that has an associated software application. Software features that have been included in CGM systems include viewing glucose levels over time, indicating glucose trends, and alerting the patient of high and low glucose levels.

SUMMARY

In some embodiments, an apparatus includes a body having a bottom surface and a top surface. An actuator is coupled to the body and extends through the top surface of the body. A needle is mounted to the actuator. The needle comprises an inner diameter and a slot along a length of the needle to a tip of the needle. A sensor is coupled to a plurality of wires. The sensor and the plurality of wires are sized to fit through the inner diameter of the needle. A base is configured to be moveable by the actuator and includes a cutout, a circuit board having a microprocessor electrically connected to the circuit board, and a plurality of contacts. Each contact is coupled to a wire of the plurality of wires. A power source is electrically connected to the circuit board and coupled to the base. A bracket is coupled to the bottom surface of the body and configured to receive the base. A patch is coupled to the bracket and has an adhesive. A needle is configured to be moveable by the actuator through the cutout on the base. The plurality of wires extend from the circuit board of the base, through the needle and out of the slot of the needle.

In some embodiments, a system includes the sensor coupled to a plurality of wires. A base includes a circuit board having a microprocessor electrically connected to the circuit board and a plurality of contacts. Each contact is coupled to a wire of the plurality of wires. A power source is electrically connected to the circuit board and coupled to the base. A needle is configured to be moveable through a cutout on the base. The plurality of wires extend from the circuit board of the base, through the needle and out of the slot of the needle.

In some embodiments, a method for constructing the base includes coupling a sensor to a plurality of wires. The sensor and the plurality of wires are sized to fit through the inner diameter of the needle. A wire of the plurality of wires is coupled to a contact of the plurality of contacts. Each contact has an opening of a plurality of openings on a circuit board and the opening has a metal coating. A fastener having a protrusion is attached into the opening. A diameter of the protrusion is less than a diameter of the opening, and the wire of the plurality of wires is between the opening and the protrusion. A power source is connected to the circuit board. The circuit board and power source is assembled in a base. The base having the circuit board, the microprocessor, the contact of the plurality of contacts coupled to the wire of the plurality of wires, and the power source is a sealed unit.

BRIEF DESCRIPTION OF THE DRAWINGS

FIG. 1 shows various views of flat-surface electrodes, in accordance with some embodiments.

FIGS. 2A and 2B show cross-sectional views of a core wire with a triangular cross-section, in accordance with some embodiments.

FIGS. 2C and 2D depict a longitudinal cross-sectional view and a perspective view, respectively, of the end of the triangular core wire, in accordance with some embodiments.

FIGS. 8A-8C are views of components of the base assembly of FIGS. 4A-4C, in accordance with some embodiments.

FIG. 26 is a cross-sectional view of wire connections in a device assembly, in accordance with some embodiments.

FIG. 27 provides views of formed contacts that are fabricated using printed circuit board components, in accordance with some embodiments.

FIG. 28 shows the contacts of FIG. 27 in a subsequent manufacturing stage, in accordance with some embodiments.

FIG. 42 is a simplified flowchart for a method for constructing the base, in accordance with some embodiments.

DETAILED DESCRIPTION

Figure 3:
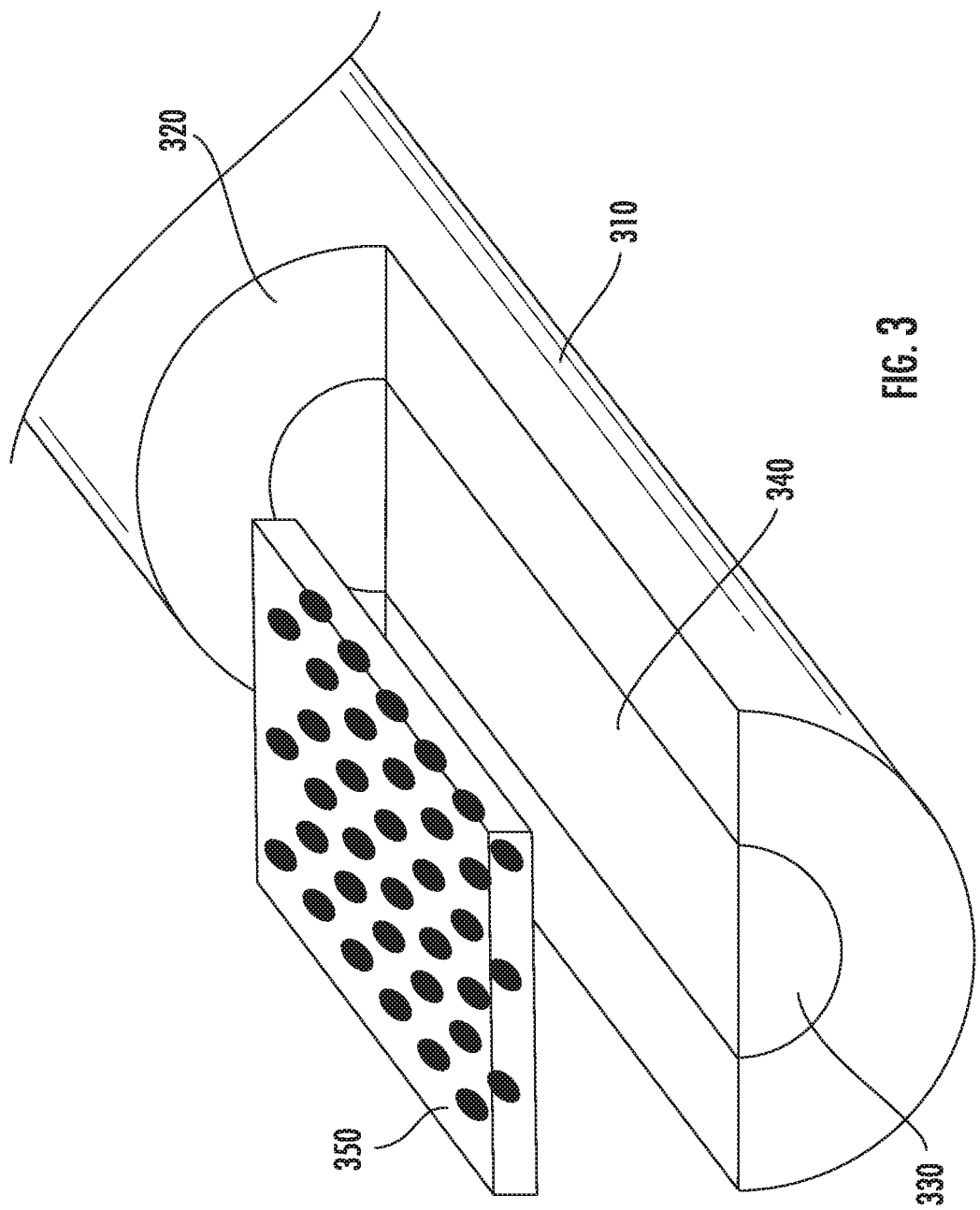
FIG. 3 shows an electrochemical element being mounted to a flat-surface electrode, in accordance with some embodiments.

Most CGM sensor designs are either planar (flat substrate) or wire-based. Planar types are more amenable to use with 3-pole electrochemical designs since simple wire traces and small electrodes can be easily constructed. However, planar types have deficiencies regarding physiology since a planar substrate has some directionality and also has sharp edges due to its geometry, which leads to a more aggressive biologic response to the device. Wire-based systems result in better physiological responses from the patient than planar systems due to the smooth nature of their geometry but have been mostly confined to a single wire for ease of insertion through a needle. This single wire constraint due to the space limitations of needle-based sensor delivery typically limits the designs to 2-pole electrochemical designs. In the 2-pole design, the reference electrode is non-renewable and thus the electrode material is consumed to complete the electrochemical circuit, which limits the working life of the system.

A challenge of wire-based sensor designs is making electrical connections on the distal end. The single wire configuration requires in-situ fabrication of working membranes and chemistries and thus limits the approaches and materials that can be used in such designs. Separate wires for working, reference and counter electrodes would be ideal for ease of fabrication; however, this approach is limited by the internal diameter of the insertion needles.

In some embodiments, a sensor with a wire-based 3-pole design is used. The design uses a split-wire configuration which enables three wires for the working, reference and counter electrodes to occupy the space of only two full wires. For example, the reference electrode and the counter electrode have a cross-section such that the two wires coupled together occupy the space of one full wire while providing nearly the same surface area as two full wire electrodes. Therefore, the 3-pole design can fit within the inner diameter of a typical insertion needle instead of two full wires.

The present embodiments disclose a wire-based 3-pole electrochemical design where the working chemistries are made separately from the wires and then bonded to the underlying sensor wires. This allows for lower cost materials and methods since components of the present CGM devices can be made independently from each other. Also, more cost-effective scaled manufacturing is enabled since manufacturing the wires separately does not require 100% sensor quality testing, and quality testing can be performed on a sheet or lot basis. Some embodiments of the disclosed wire-based systems use carbon-based, such as graphene-based, electrodes manufactured in large-scale sheets with working chemistries that are then attached to the working electrode.

Furthermore, applicator designs and electrical connection configurations are disclosed that support simple insertion of the 2-pole or 3-pole wire designs. Embodiments of applicators include vertical and angular insertions, and a design features for improving robustness, reliability, and cost of these designs with an on-board battery included into the base of the applicator. In some embodiments, the applicator design uses of a slotted needle that creates the penetration into the skin and then can be retracted back over sensor wires that are "hardwired" to the electronics such as the circuit board and power source in the base. The present embodiments also include methods of making electrical connections of the wire sensors within a sensor applicator. In some embodiments, a unique feature of these designs is "flag" shaped electrical connections that move with the wires during insertion and then lock into the base, allowing the needle to be retracted while leaving the wires in place.

FIG. 1 illustrates an embodiment of a wire-based 3-pole system 100 of a continuous glucose monitoring sensor in which a split wire design is used. In this embodiment, a portion of a wire such as a half-wire is provided for a reference electrode 110. The wire is a sensor wire for the reference electrode 110 in a plurality of sensor wires. Likewise, a portion of a wire such as a half-wire is provided for a counter electrode 120 and is a sensor wire for the counter electrode 120 in the plurality of sensor wires. The sensor wire for the reference electrode and the sensor wire for the counter electrode each have a flat surface across approximately its diameter such that the wires have semi-circular cross-sections. In some embodiments, the flat surface of the reference electrode 110 and the flat surface of the counter electrode 120 face toward each other.

Each half-wire electrode, such as the reference electrode 110 and the counter electrode 120, may have an 82% of the surface area of a full wire having the same diameter, while still allowing the reference and counter electrode assembly to fit within a small diameter insertion needle 102 for insertion under the skin. In other words, the split-wire configuration enables the reference electrode 110 and the counter electrode 120 to provide nearly the same surface area as two full wire electrodes, but only occupy the space of one wire within the insertion needle 102 instead of two full wires. Although half-wires are depicted for the reference electrode 110 and counter electrode 120—where each wire has been split along its diameter along a length of the wire—other partial fractions of the wire may be utilized to form the flat surface electrodes. The flat surface of the reference electrode 110 and counter electrode 120 may be defined by a chord across a circular cross-section of the wire so that the cross-sectional area of the reference electrode 110 and the counter electrode 120 is 30% to 70% of the cross-section of the wire. Therefore, the circular cross-section of the wire may be more than or less than a semicircle. This enables the wire to obtain larger percentages of surface area of a full wire.

A working electrode is fabricated by also creating a flat portion on a wire. FIG. 1 shows two embodiments—a 1-sided working electrode 130 and a 2-sided working electrode 135—either of which may be used. The 1-sided working electrode 130 has a semicircular cross-section where half of the wire's cross-sectional area has been removed. As described with reference to the reference electrode 110 and the counter electrode 120, other partial fractions of the wire may be utilized to form the flat surface electrodes by defining by a chord across a circular cross-section of the wire so that the cross-section of the wire may be 30% to 70% of the full wire. The 2-sided working electrode 135 has a rectangular cross-section where portions of the wire above and below the flat portion have been removed. The portions removed may be equal or one portion—either the top portion or the bottom portion—may be larger than the other. The flat portion(s) of working electrode 130 or 135 is used to support an electrochemical element which is the reactive component that senses glucose in the patient's interstitial fluid, and the wire is the sensor wire for the working electrode in a plurality of sensor wires.

In some embodiments, the sensor is a 3-pole design and includes the working electrode having a first wire with a first flat surface and an electrochemical element on the first flat surface. The first wire is a first sensor wire for the working electrode. A reference electrode has a second wire with a second flat surface. The second wire is a second sensor wire for the reference electrode. A counter electrode has a third wire with a third flat surface. The third wire is a third sensor wire for the counter electrode. The first sensor wire, the second sensor wire and the third sensor wire are a plurality of sensor wires.

FIG. 1 also shows insertion of the electrodes into an insertion needle 102, where it can be seen that this 3-pole design of the sensor occupies a space within the needle lumen equivalent to only two wires instead of three wires. The working electrode (where 2-sided working electrode 135 is shown in this illustration) utilizes the space of one wire, and the reference electrode 110 and counter electrode 120 together occupy the space of another wire. For example, the combined diameter of the plurality of sensor wires such as the working electrode 135, the reference electrode 110 and counter electrode 120, is less than the inner diameter of an insertion needle 102. Diameters of each of the plurality of sensor wires used for the reference electrode 110, counter electrode 120 or working electrode 135 may be, for example, from 0.002 inches to 0.007 inches while typical insertion needles may have an internal diameter of 0.16 inches to 0.21 inches or 25 to 27 gauge. The length or surface area of the electrode portions themselves can be tailored according to the desired sensor sensitivity and required design specifications.

FIGS. 2A-2D show other embodiments of systems used in a continuous glucose monitoring sensor with flat surface electrodes and a support core wire 140. FIGS. 2A and 2B show cross-sectional views of a core wire 140 with a triangular cross-section, in accordance with some embodiments. For example, designs 200 and 210 are compact systems assembled with the core wire 140. The first wire of the working electrode 135, the second wire of the reference electrode 110 and the third wire of the counter electrode 120 are coupled to the core wire 140 and surround the core wire 140 with the triangular cross-section. Each of the wires for the working electrode 135, the reference electrode 110 and the counter electrode 120 have flat surfaces that are positioned to be facing a surface of the triangular-shaped core wire 140. The reference electrode 110 and the counter electrode 120 may be approximately semicircular in cross-section, while the working electrode may be semicircular (as shown in FIG. 2A, design 200) or rectangular (as shown in FIG. 2B, design 210) in cross-section. Other cross-sectional shapes may be used for the working electrode 135, the reference electrode 110 and the counter electrode 120 when coupled to the core wire 140.

FIGS. 2C and 2D depict a longitudinal cross-sectional view and a perspective view, respectively, of the end of the triangular core wire 140, in accordance with some embodiments. Schematics 220 and 230 illustrate that the triangular design can be a completely self-inserting sensor. That is, a tip 142 of the triangular core wire 140 may be sharpened to a point, or pointed, such that the sensor can be inserted directly, without requiring the use of a needle to place the sensor within the subcutaneous tissue.

The flat surfaces of the electrodes in these various embodiments provide support for fragile electrochemistry materials, such as a carbon-based sheet which is typically brittle. In some embodiments, a support sheet (e.g., consisting of an electrodeposited of melt extrusion of pyrrole or polyaniline) can be created, and then a carbon material is deposited onto the support sheet. The support sheet provides a substrate to which the carbon bonds well, and also should be conductive to electrically couple the electrochemical (e.g., carbon/pyrrole) sheet to the electrode wire. The conductive sheet material can then be impregnated or coated with sensing chemistries via various drawn membrane or spin coating techniques.

The electrochemistry material sheet can be made separately from the electrode wire, and then mounted on the flat surface of the electrode as shown in FIG. 3. In this example of FIG. 3, a wire 310 having insulation 320 surrounding a conductive wire core 330 has a portion of its end removed to form a flat surface 340. A carbon or carbon/graphene/pyrrole sheet 350 is cut to size and placed on the flat surface of the flat electrode wire so that the electrochemical element comprises carbon. For example, once the flat sheets are fabricated with sensing chemistries, these sheets 350 can be laser cut into small portions and then assembled onto the flat surface 340 of the wire 310.

The support sheet can be made by, for example, melt extrusion of a pyrrole layer to make electrical contact to the flat surface of the electrode. In other embodiments, an electro-polymerization of additional pyrrole can be used to connect the electrode metal to the sheet, or conductive adhesives or other electrical contact bonding methods can be used to make electrical contact as well.

In other embodiments, the electrochemistry components can be formed in-situ on the electrode instead of forming a sheet separately from the electrode. For example, an alternative fabrication method for in-situ creation of sensing chemistry and membrane may include pad or screen printing, painting, or 3D-printing directly onto the flat plane(s) of the wire.

The carbon material can be in the form of, for example, an ink or a paste, and the carbon can include various allotropes such as but not limited to graphite, graphene, fullerenes, and/or nanotubes. Materials other than pure carbon can be used, including platinum black, carbon platinum pastes, carbon gold pastes or other known working electrode surface materials, alone or in combination (e.g., carbon, platinum, gold, palladium, rhodium, iridium). In some embodiments, high surface area nano-porous materials of graphene and/or other nanomaterials can be used, to increase the number of active chemical sites available for reactions.

Carbons are lower cost than the noble metals that are typically used for biocompatible applications (e.g., gold and platinum). However, due to the inherent brittle nature of carbon materials, carbon-based electrodes have been conventionally used in planar style electrodes (such as finger sticks) where the carbon can be supported by the planar substrate without applying undue mechanical loads on the electrode. The present embodiments overcome the difficulties of using carbon-based materials on a wire electrode by providing the mechanical support required for the carbon material and by eliminating the typical need for in-situ fabrication of the working chemistries on the wire (although in-situ fabrication may be used).

After the sensing chemistry has been created on the electrode, whether separately or in-situ, a final dip coating may be used to seal the entire system using hoop strength created by polymer shrinkage upon drying. This final polymer layer also serves as a biocompatible and glucose limiting membrane required for creating a linear glucose response, and provides the biosafety required for an implanted sensor.

The present flat-wire embodiments may also be used to optimize the electrochemical substrate so that it can be tuned for direct electron transfer chemistries by keeping the redox center close to the porous carbon surface or within encapsulating polymers. One such embodiment uses an aminophenol covalently bonded to the carbon electrode by electrografting and is subsequently linked by diazonium chemistry to glucose oxidase (GOX) to provide direct electron transfer. Embodiments can be directly used with conductive polymers (e.g., PEDOT-PSS, poly-pyrroles, polyanilenes, etc.) formed in-situ on a porous carbon sheet that would work with normal enzymes (either glucose oxidase (GOX) or glucose dehydrogenase (GDH)) and/or enzymes with a mediator to create hybrid enzyme systems that alter the need for high bias voltages and thus reduce interferences from all sources.

In some embodiments, a redox enzyme can be immobilized on the electrode surface in a new manner such that direct electron transfer between the active side of the enzyme and the transducer is possible. The major unique character of such embodiments of an amperometric glucose sensor is that the biased potential is in the range of 0 to −0.5V, ideally to be around −0.1V. In comparison, a conventional CGM sensor has a biased potential of typically +0.55V. There are two major methods to achieve the lower biased potential of the present designs. A first method is an in-situ electro-polymerization of a conductive polymer with a redox enzyme. The sensing layer is formed by applying potential cycles or sequences of suitable potential pulses with the enzyme and monomer/comonomers solution. An advantage of this approach is that the films are formed exclusively on the electrode surfaces due to the electrochemical initiation of the deposition process. A second method is the incorporation of a redox mediator into the polymers or the prepolymer. The polymer that contains the redox mediator can be physically mixed with the enzyme, then be deposited onto the electrodes through dip coating, spin coating or other coating methods. This can also be achieved through the in-situ polymerization of the redox-mediator-containing prepolymer with other active prepolymers in the presence of the enzyme solution and the electrodes. The resulting sensing layer on the electrode contains the matrixed enzyme inside the polymer network with the covalently linked redox mediator.

Various embodiments of applicators for inserting the CGM sensors into a patient shall now be described.

Figure 4A:
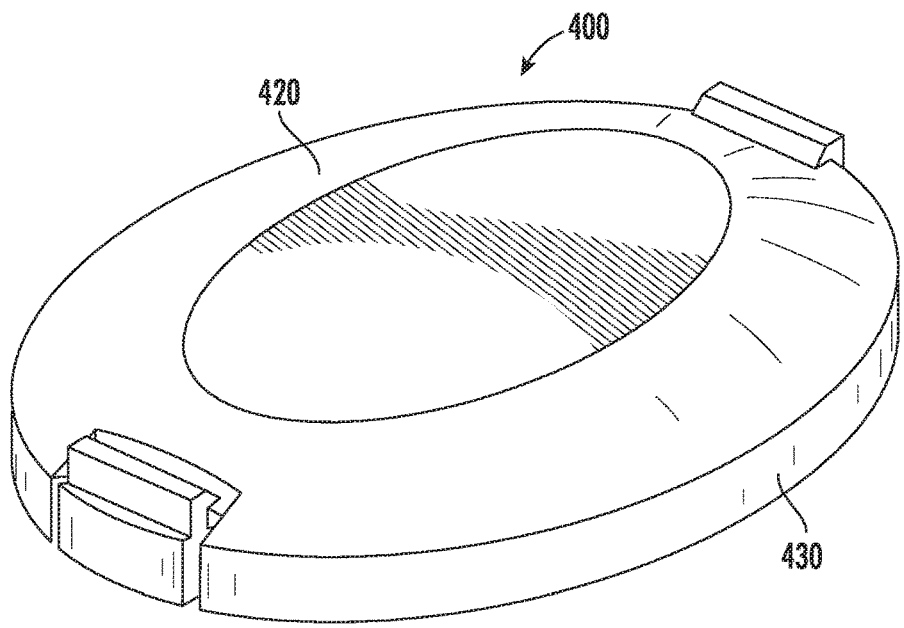
FIGS. 4A-4C are various views of a base assembly, in accordance with some embodiments.
Figure 4B:
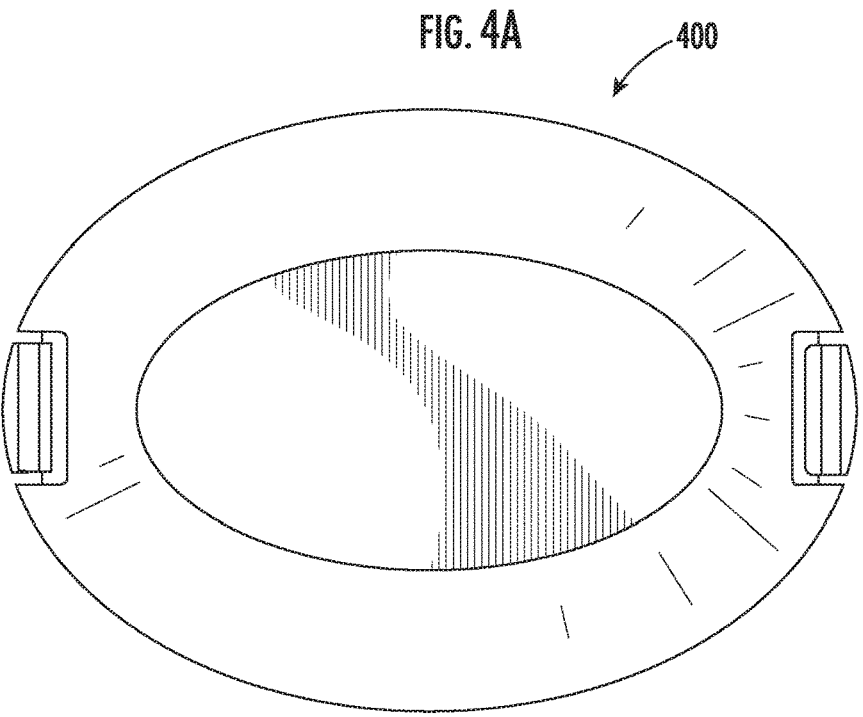
Figure 4C:
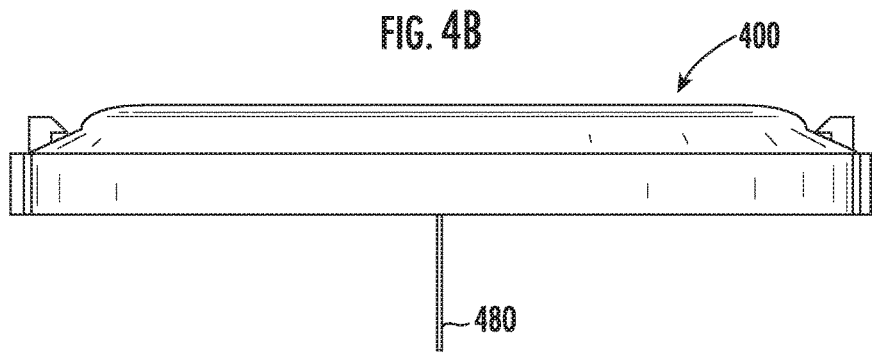

FIGS. 4A-4C show an embodiment of a base assembly 400 which will be worn by a patient during glucose monitoring. The base assembly 400 includes cover 420 and base 430, and can be adhered to an abdomen or an arm of the patient, for example. FIG. 4A is a perspective view, FIG. 4B is a top view, and FIG. 4C is a side view. Base assembly 400 holds a glucose sensor 480 in place on the patient and houses the electronics to which the glucose sensor 480 is attached. The glucose sensor 480 measures glucose in the patient's interstitial fluid and can be seen in FIG. 4C extending from the bottom surface of the base assembly 400. In some embodiments, the base assembly 400 may have a length of 2.13 inches, a width of 1.50 inches, and a height of 0.27 inches. These sizes may be smaller due to further miniaturization of electronics and smaller battery usage. To deliver the CGM sensor into the patient, the cover 420 is removed from the base 430, and an applicator attaches to the base 430. A cover 420, which is dome-shaped in this embodiment, serves as a lid for the base 430 after the applicator has inserted the sensor and has been removed from the base.

Figure 5:
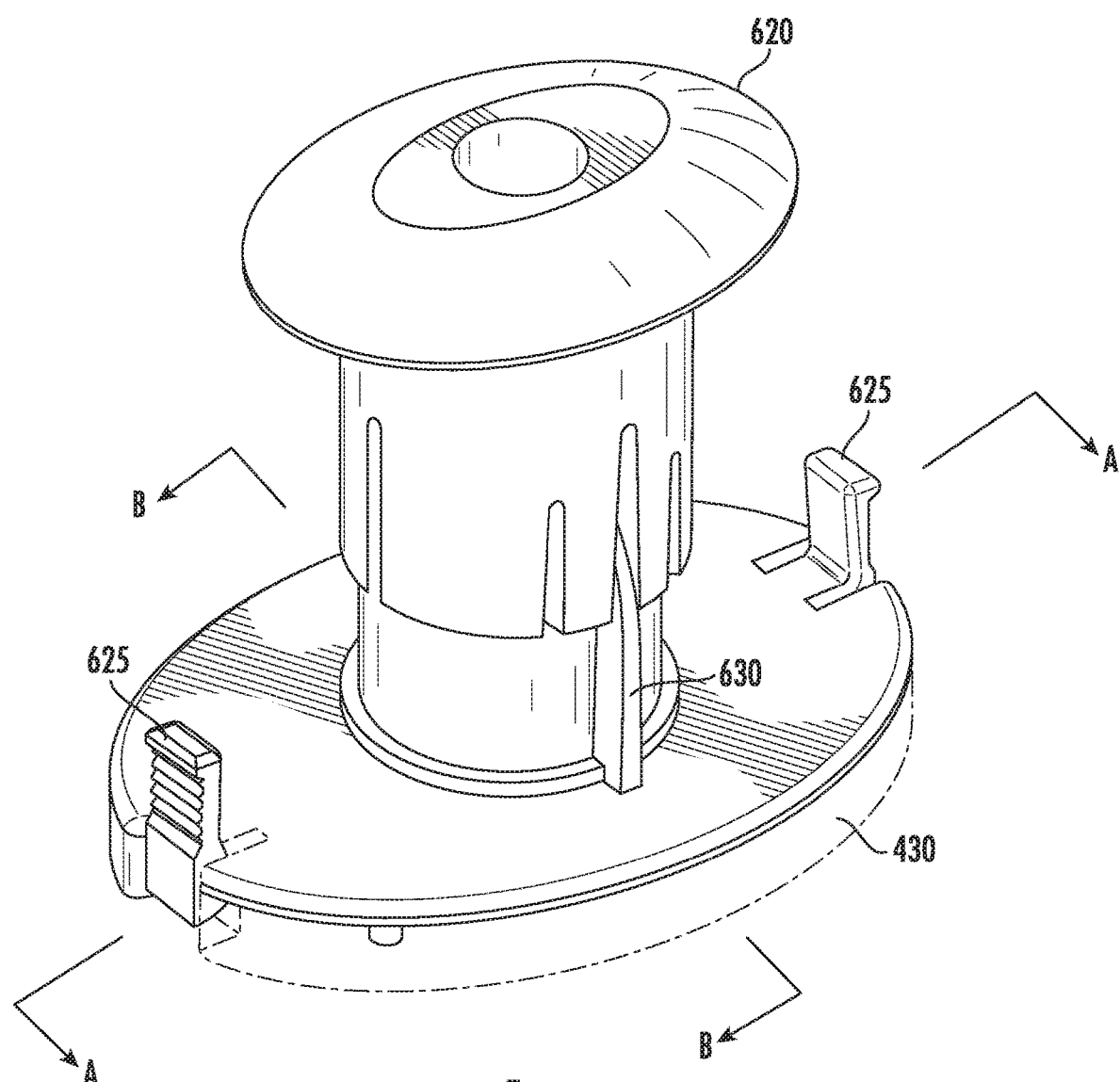
FIG. 5 is a perspective view of a vertical insertion applicator, in accordance with some embodiments.

An embodiment of an applicator for a glucose monitoring system is shown in FIG. 5, in which a rail 630 and a plunger 620 are used for a vertical insertion design. The applicator is coupled to the base 430 by tabs 625 in this embodiment. FIG. 5 is a perspective view before the needle 610 is deployed, such that plunger 620 is raised relative to base 430. After the needle 610 has been deployed, the plunger 620 moves downward towards base 430, guided by rails 630.

Figure 6:
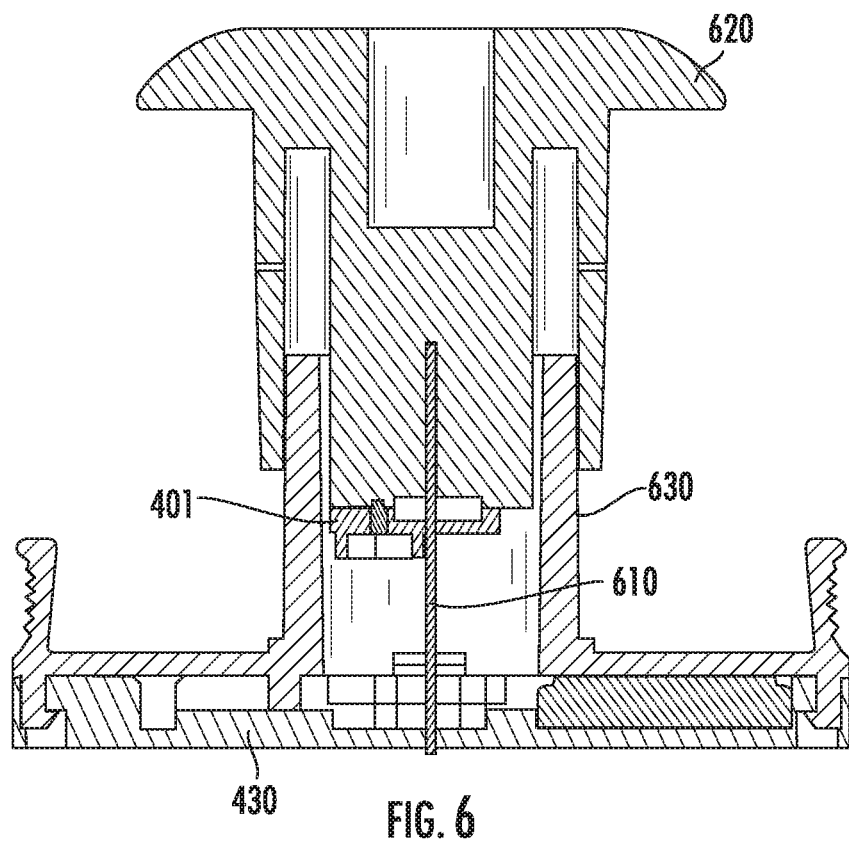
FIGS. 6 and 7 are cross-sectional views of the applicator of FIG. 5, in accordance with some embodiments.
Figure 7:
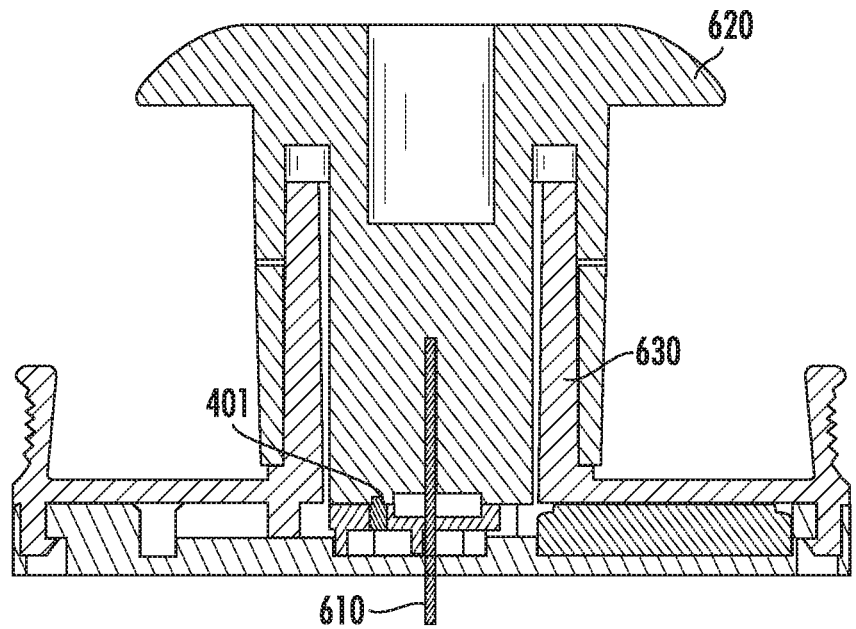

FIGS. 6 and 7 are vertical cross-sectional views taken along section A-A and B-B of FIG. 5, respectively, where FIG. 6 is before needle deployment and FIG. 7 is after deployment. A sensor base 401, which includes the CGM sensor and associated wiring, moves with the needle 610 during insertion. After the needle 610 has been deployed, the sensor base 401 locks into and stays in the base 430 when the needle is removed. An advantage of this vertical style of insertion is that it does not rely on manual dexterity to deploy the sensor. A patient can use the palm of the hand to push down and provide the force for deployment. This vertical deployment style can be advantageous in, for example, very young or elderly populations for self-insertion of the sensors.

Figure 8A:
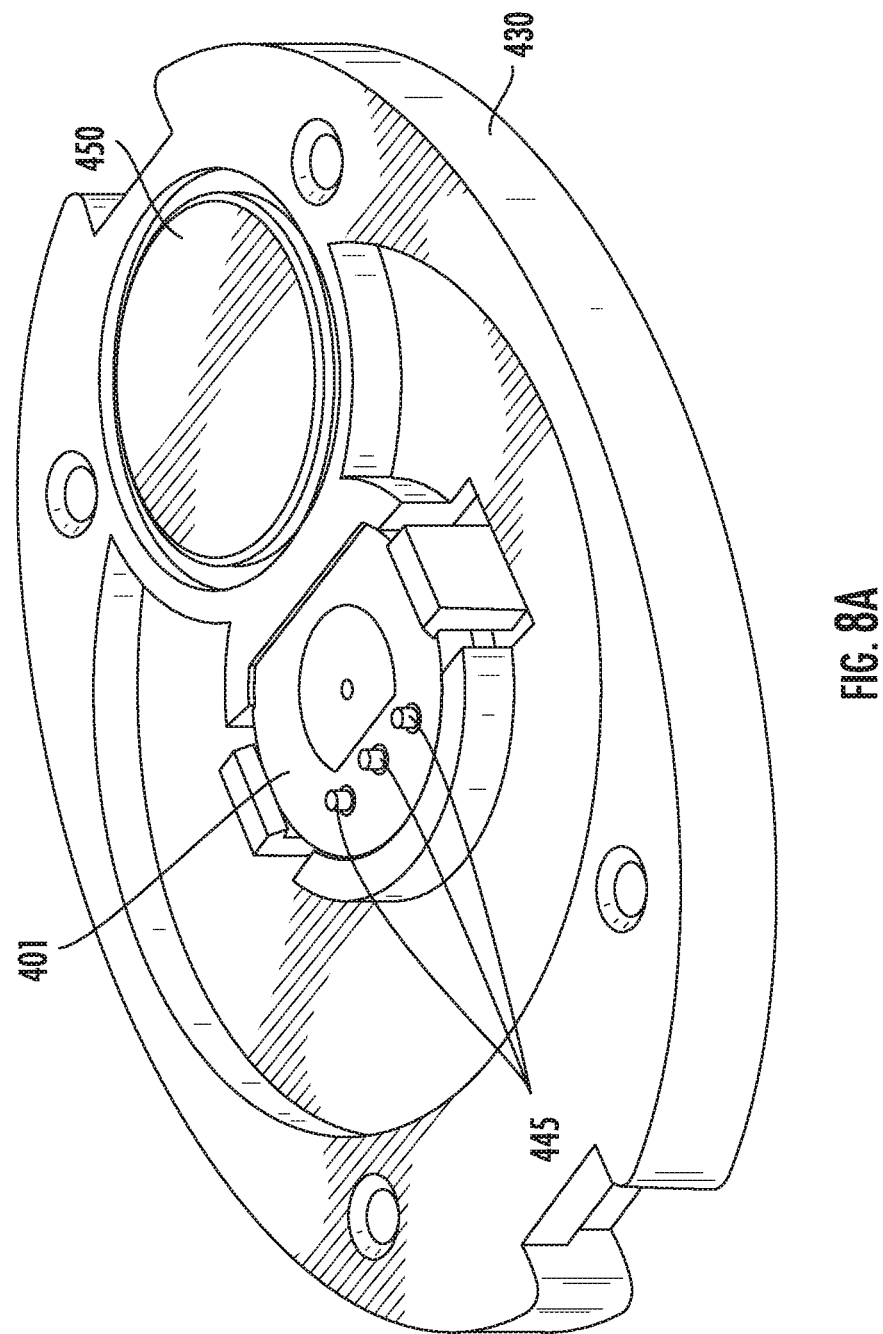

FIGS. 8A-8C show perspective, side cross-sectional and end cross-sectional views, respectively, of the base assembly 400 after the sensor has been placed in the patient. In FIG. 8A, the dome-shaped cover 420 has been removed to show the interior of base 430, where a battery 450 and the installed sensor base 401 are seen. Sensor base 401 has electrical contacts 445 for sensor wires 460 of the glucose sensor 480. FIGS. 8B-8C show cover 420 installed on base 430, where cover 420 has a circuit board 440 included in its underside. Thus, when the cover 420 is coupled to base 430, the circuit board 440 is placed in contact with the electrical contacts 445. Circuit board 440 retrieves the amperometric readings, such as by sending the readings to a mobile device. The sensor wires 460, which may also be referred to as lead wires in this disclosure, are electrically coupled to the contacts 445 (described hereafter).

Figure 9:
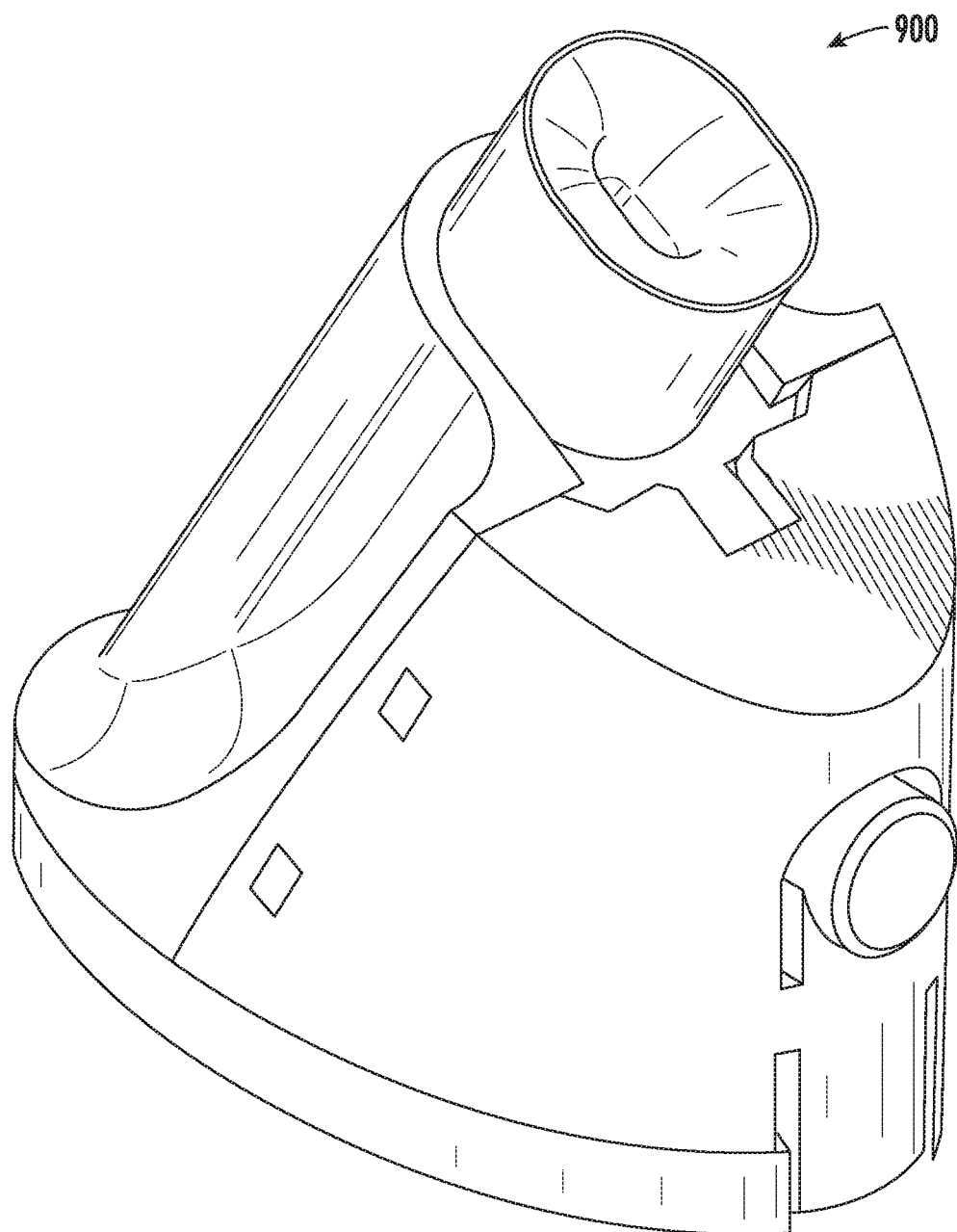
FIG. 9 shows a perspective view of an angled insertion applicator, in accordance with some embodiments.

FIG. 9 shows a perspective view of another embodiment of an applicator for a glucose monitoring system in which an angled insertion of the needle is achieved using a plunger assembly 900. This angled style of applicator helps reduce sensor noise caused by micro-motion of the sensor tip when the sensor is monitoring the patient. Noise can come from forces that are transmitted down the wire from the base mounted onto the surface of the skin from any forces applied onto the base by the normal act of wearing the device.

Figure 10A:
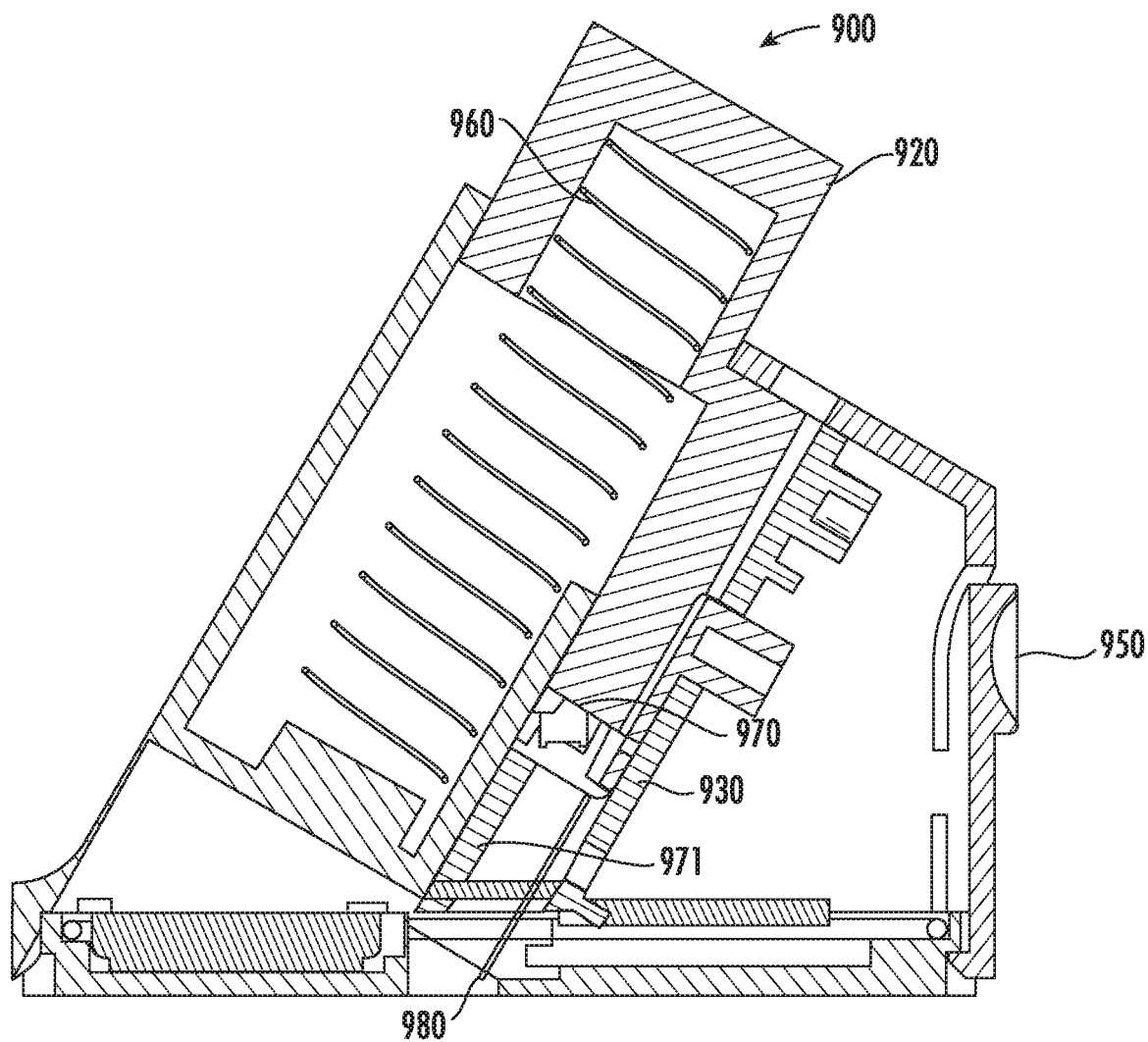
FIGS. 10A-10B are cross-sectional views of the applicator of FIG. 9, in accordance with some embodiments.
Figure 10B:
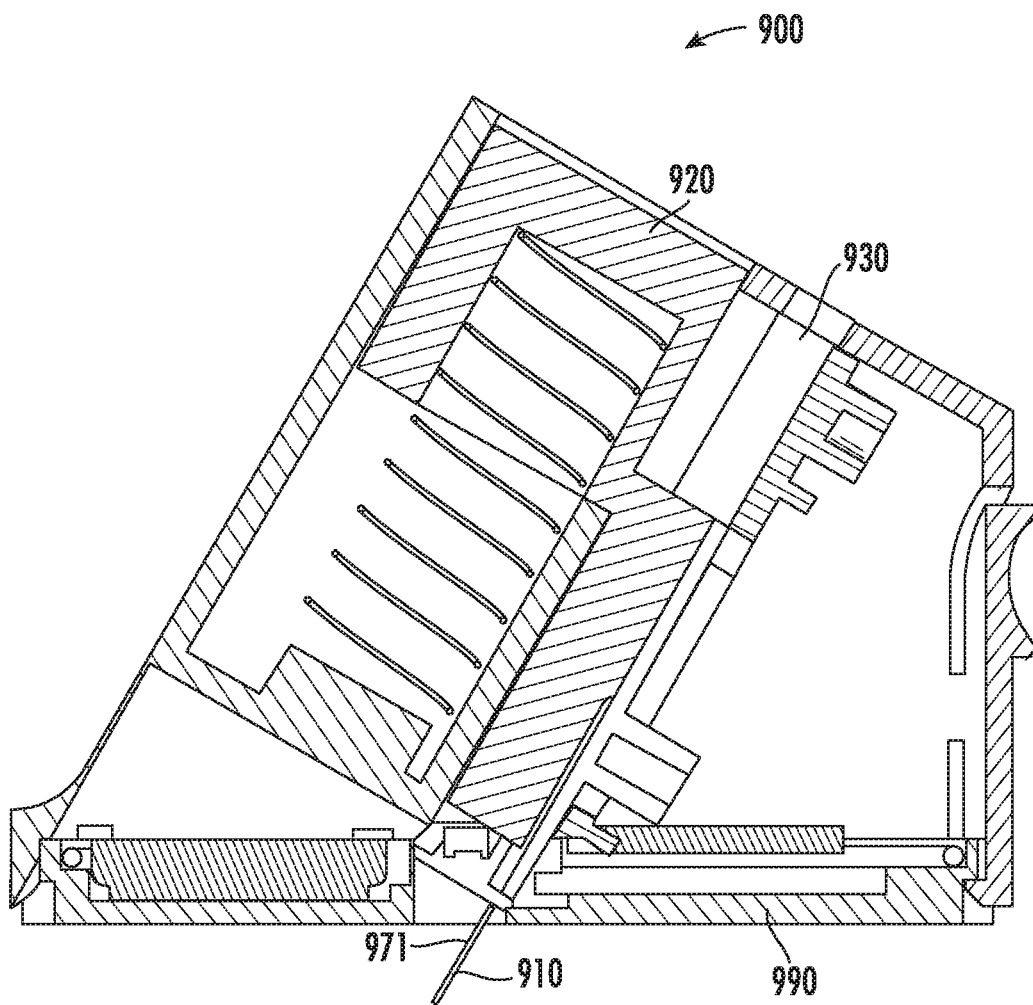

FIGS. 10A and 10B are vertical cross-sectional views of the plunger assembly 900 in undeployed and deployed states, respectively. Plunger assembly 900 includes a plunger 920, a rail 930, a release button 950 and a spring 960. In other embodiments the plunger 920 can take other forms, such as a rod. A sensor base 970 moves with needle 910 which is fixedly mounted to plunger 920. Sensor wires 971 (one for each of the working, reference and counter electrodes) are connected to sensor base 970 at one end, and a glucose sensor 980 is formed at an opposite end of sensor wires 971. To deploy the needle 910, a user pushes release button 950 which allows spring 960 to contract. Consequently, plunger 920 slides downward on rail 930 as shown in FIG. 10B, and the lead wires 971 with glucose sensor 980 are inserted through needle 910 into the patient. Sensor base 970 becomes locked into base 990 when the needle is inserted, such that the sensor base 970 stays in base 990 when the needle is removed.

Figure 12:
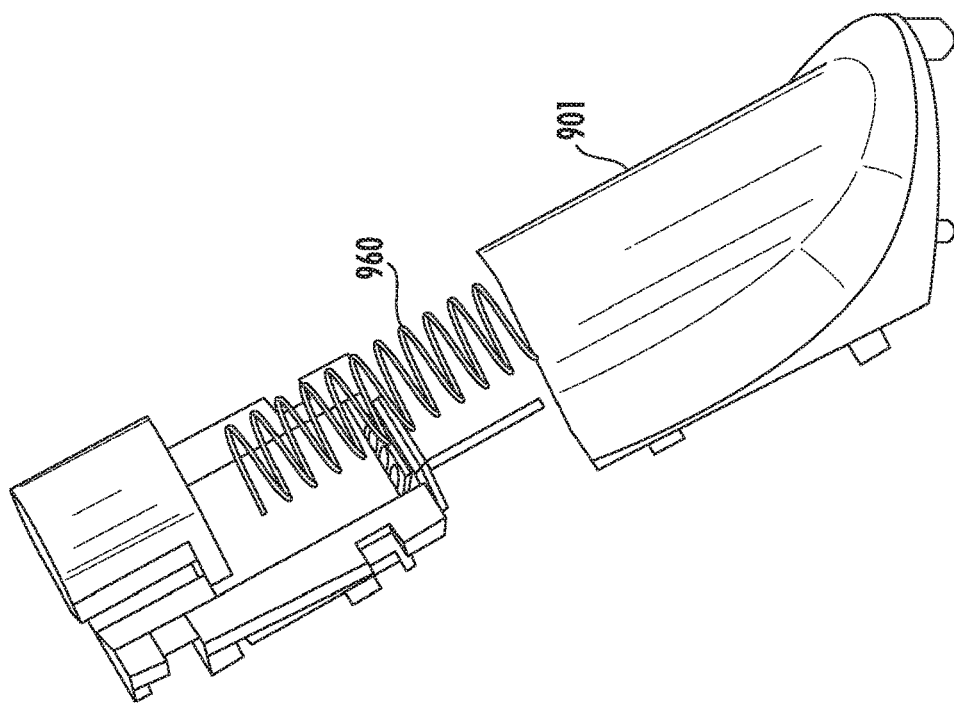
FIGS. 11A, 11B and 12 are perspective views of subassemblies of the applicator of FIG. 9 in accordance with some embodiments.
Figure 11B:
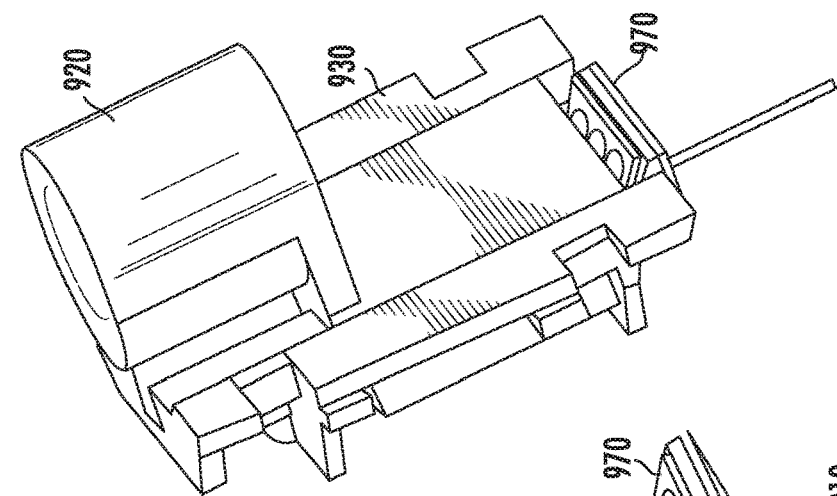
Figure 11A:
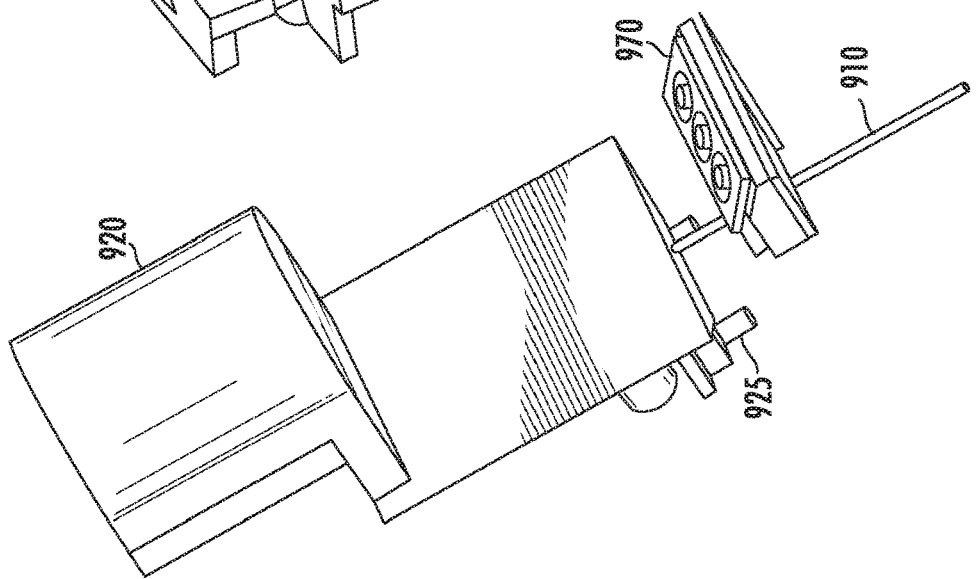

FIGS. 11A, 11B and 12 are perspective views of assembly stages for the angled insertion applicator. In FIG. 11A, plunger 920 has needle 910 fixedly attached to it. Sensor base 920 is slid onto needle 910, where pins 925 of the plunger 920 connect to the sensor base 970. In FIG. 11B, the combined sub-assembly of plunger 920 and sensor base 970 are installed onto the rail 930. In FIG. 12, the sub-assembly of FIG. 11B is placed onto a spring 960 and installed into the front cover 901.

Figure 13A:
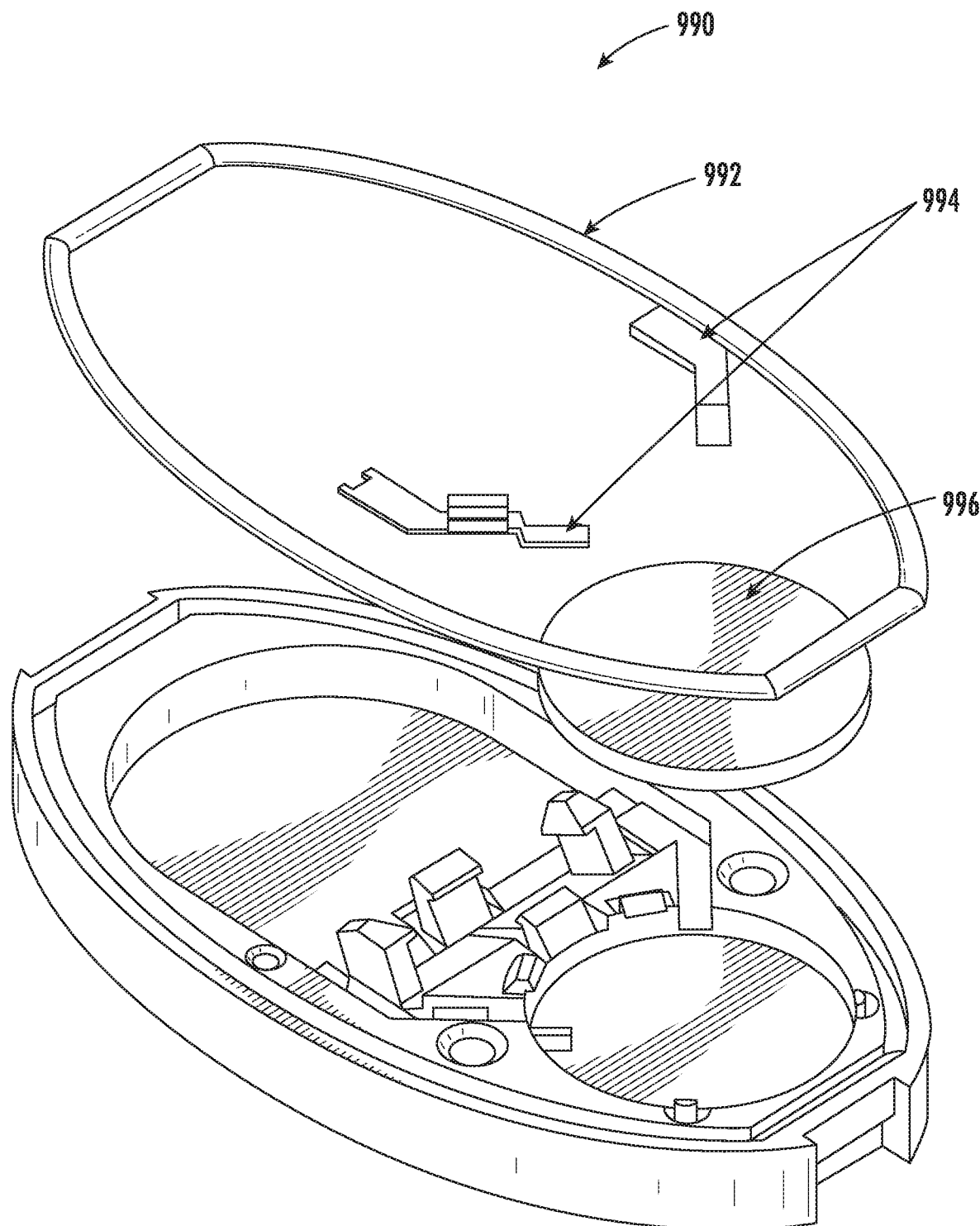
FIGS. 13A-13B are perspective views of a base assembly for an angled insertion applicator, in accordance with some embodiments.
Figure 13B:
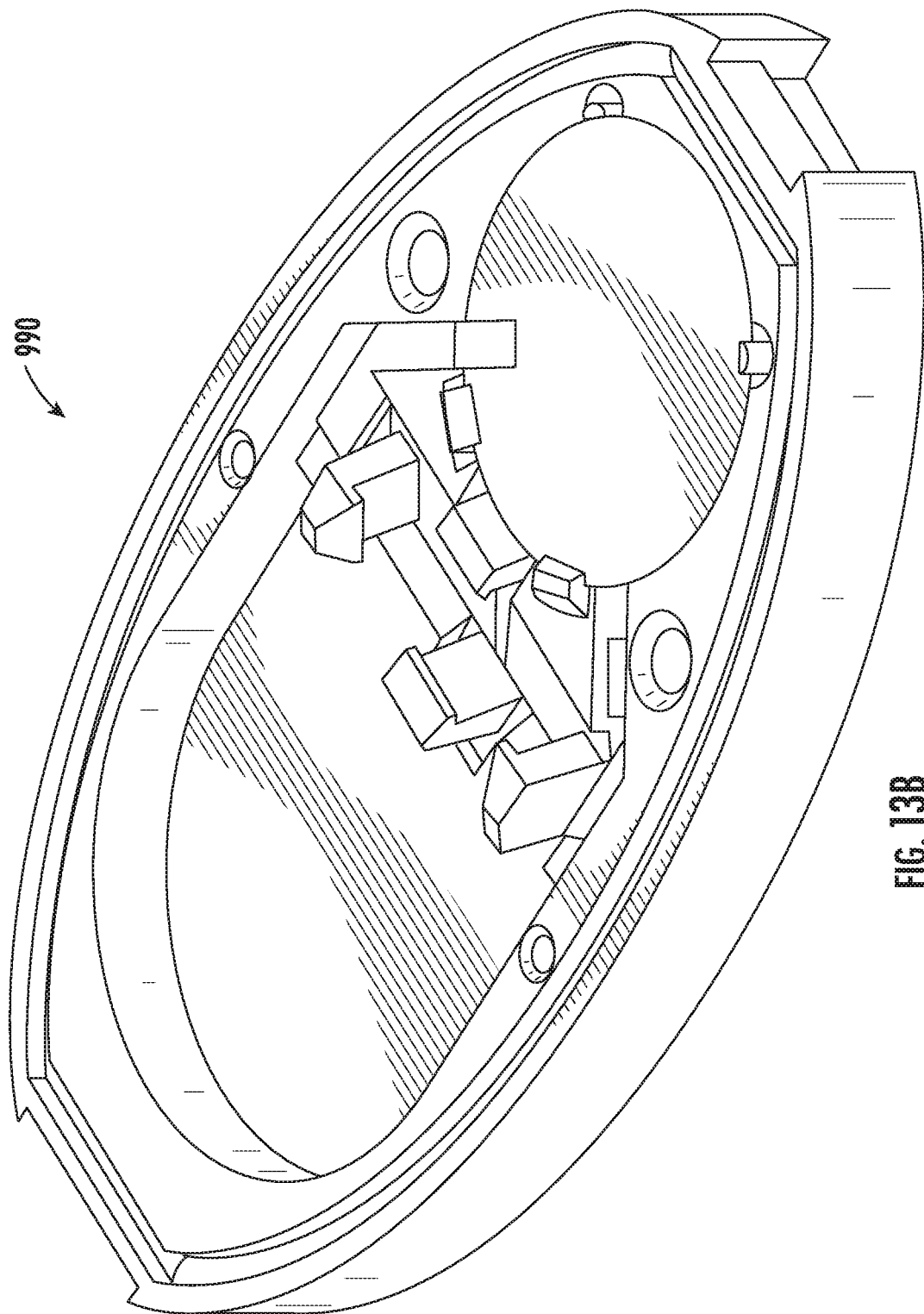

FIGS. 13A and 13B are perspective views of the base 990 for the angled insertion design, prior to sensor installment. FIG. 13A is an exploded view, showing O-ring gasket 992, battery contacts 994 and battery 996 (e.g., CR 1632 type battery). FIG. 13B is an assembled view, where battery contacts 994 serve as a conduit for supplying power from battery 996 to the circuit board and sensor.

Figure 14A:
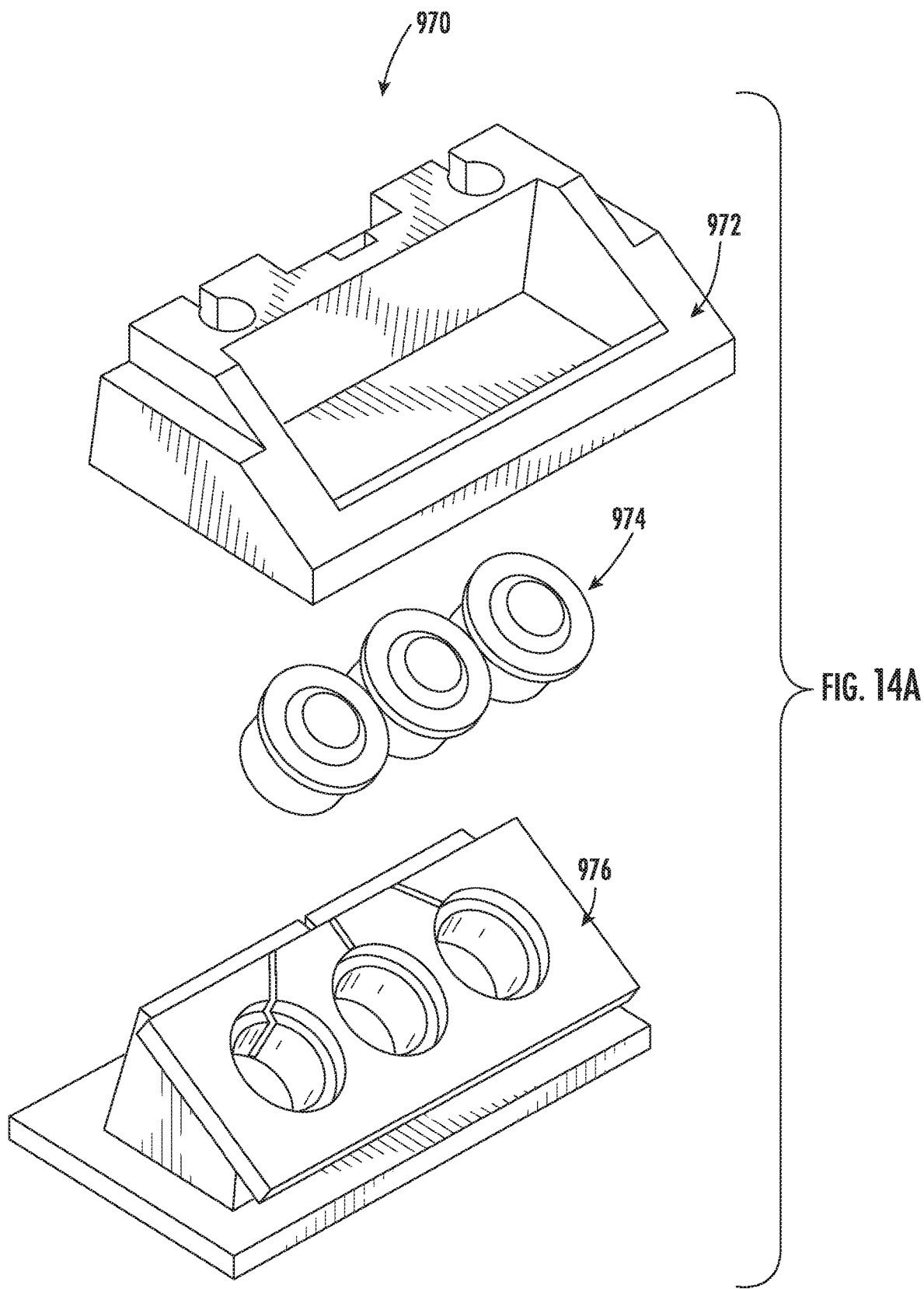
FIGS. 14A-14B are perspective views of a sensor base for an angled insertion applicator, in accordance with some embodiments.
Figure 14B:
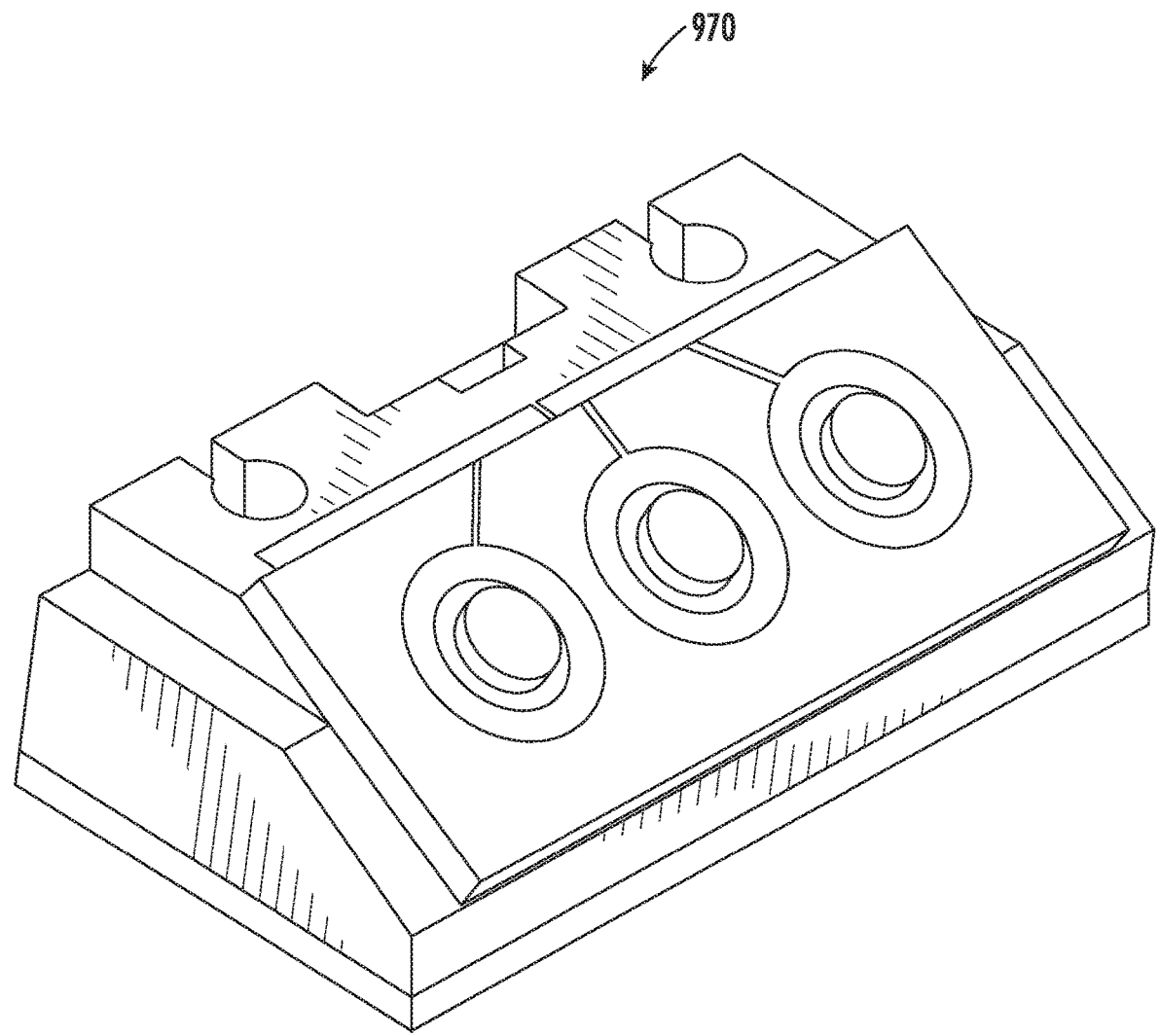

FIGS. 14A and 14B show the sensor base 970 for the angled insertion design. FIG. 14A is an exploded view, showing sensor base frame 972 (e.g., polycarbonate), sensor contacts 974 (note, the wires to the sensor are not shown for clarity), and sensor mount 976 (e.g., silicone rubber).

Figure 15A:
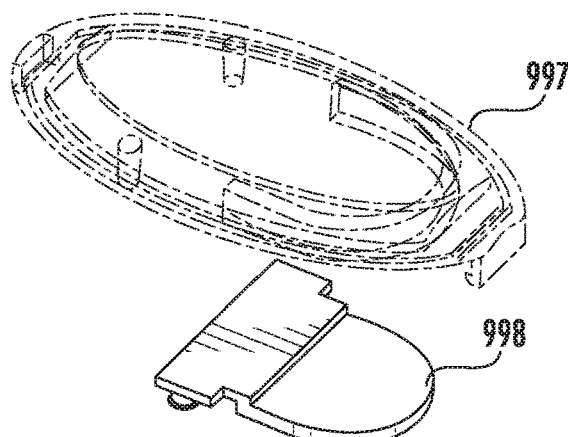
FIGS. 15A-15D show various views of a base assembly, in accordance with some embodiments.
Figure 15B:
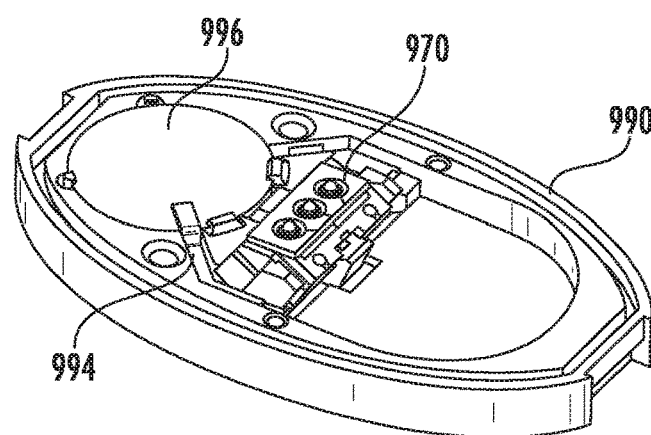
Figure 15C:
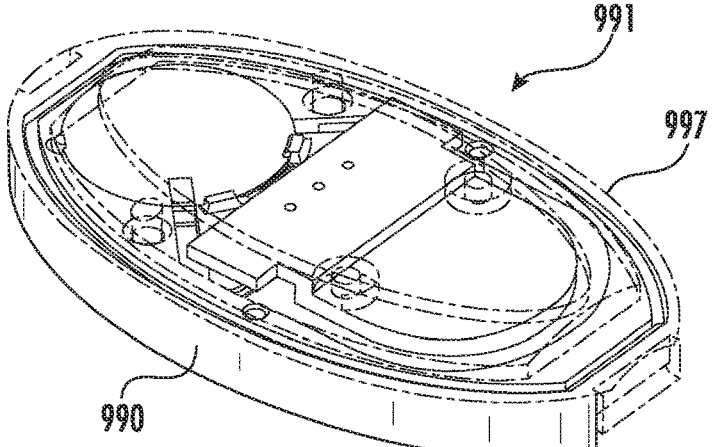
Figure 15D:
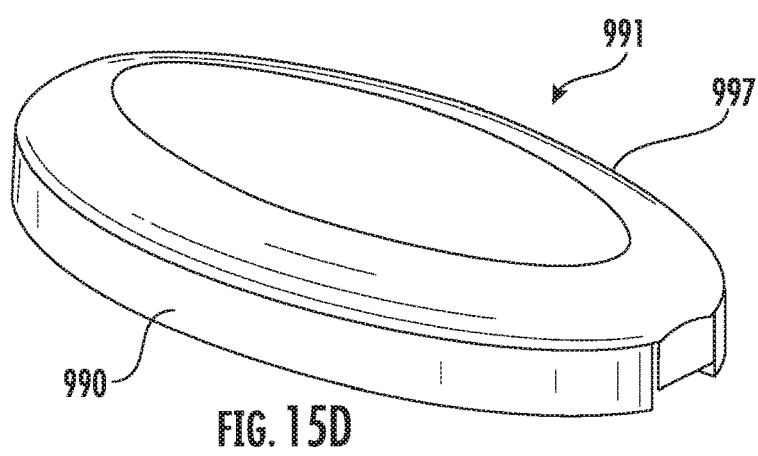

FIGS. 15A-15D show various views of the full base assembly 991 after the sensor has been inserted into a patient. Base assembly 991 includes base 990 and a cover 997. FIG. 15A is an exploded view of the cover 997 and circuit board 998, where cover 997 will be supplied with circuit board 998 mounted to its interior. FIG. 15B shows base 990 where sensor base 970 has now been installed into the original base of FIGS. 13A-13B. FIGS. 15C and 15D show the final body-worn assembly, where the applicator (including the plunger 920, front cover 901 and rear cover 902) have been replaced with cover 997. FIG. 15C shows the dome cover 997 as transparent for illustrative purposes of the interior components, and FIG. 15D shows the dome cover 997 as the actual opaque material. As can be seen in FIG. 15C, the circuit board 998 is placed over the sensor base 970. The adhesive pad for coupling the device to the user is not shown in these figures.

Other embodiments involve a self-inserting applicator which utilizes a hinged design to insert the sensor into the skin. This hinged design can provide increased mechanical advantage for delivering the self-inserting triangular needle of FIG. 3, although the hinged design may be used for inserting standard needles into the skin as well. In the hinged design, the needle is at an angle relative to the surface of the patient's skin for both self-insertion and needle removal.

Figure 16B:
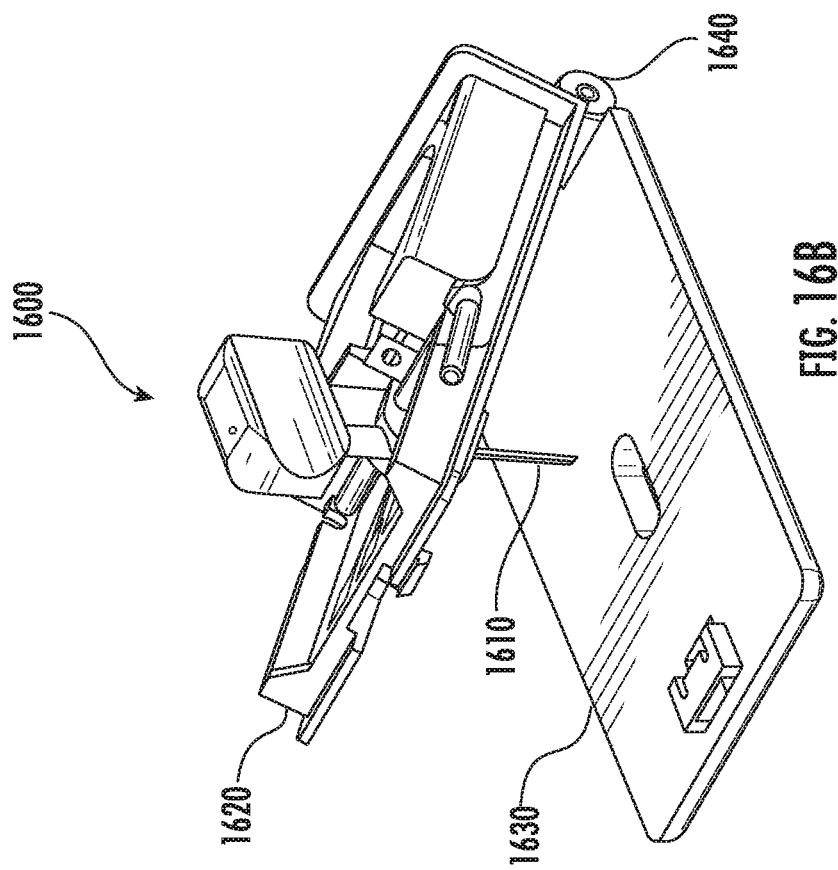
FIGS. 16A-16B are perspective views of a hinged applicator, in accordance with some embodiments.
Figure 16A:
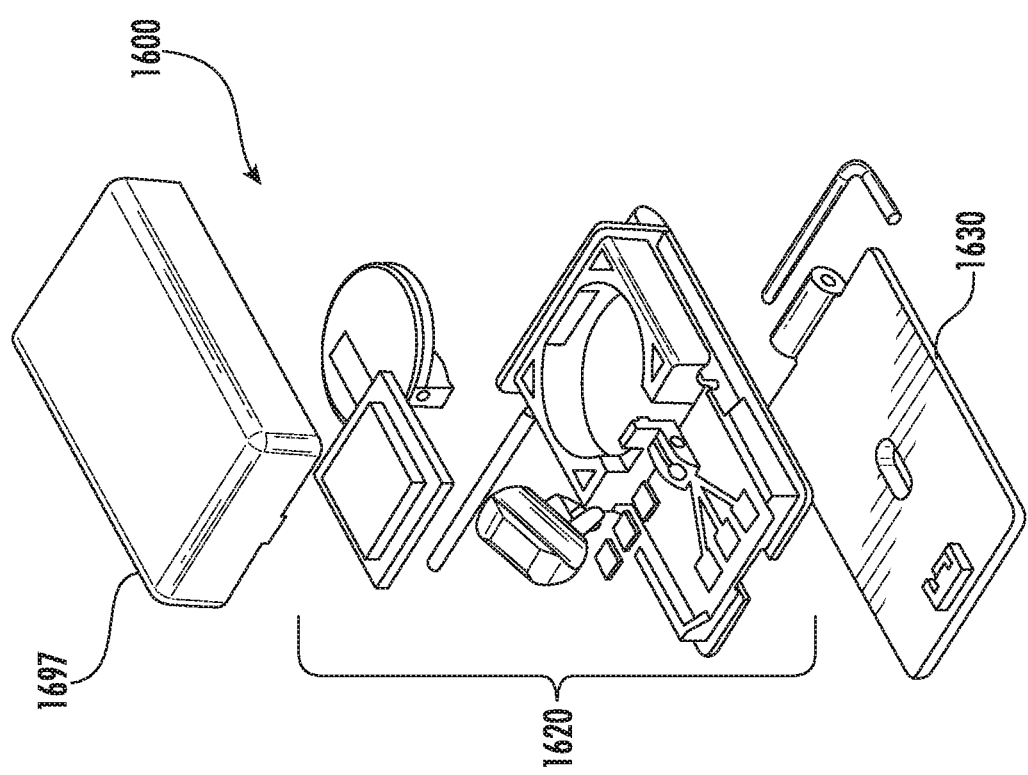

FIGS. 16A and 16B are perspective views of an embodiment of a hinged applicator 1600 with retractable needle 1610. In this hinged design, a top assembly 1620 is hinged to a platform 1630 by a hinge 1640, similar to a suitcase. FIG. 16A is an exploded view, while FIG. 16B is an assembled view excluding cover 1697.

Figure 17:
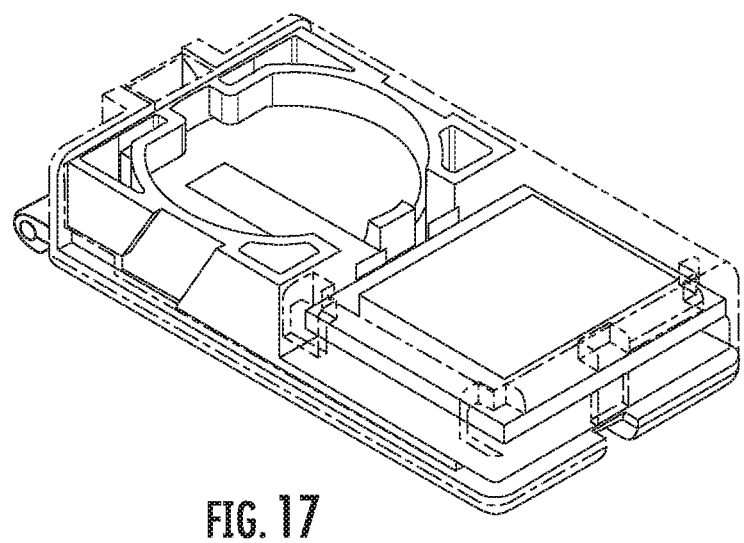
FIG. 17 is a perspective view of portions of the applicator of FIGS. 16A-16B, in accordance with some embodiments.
Figure 18A:
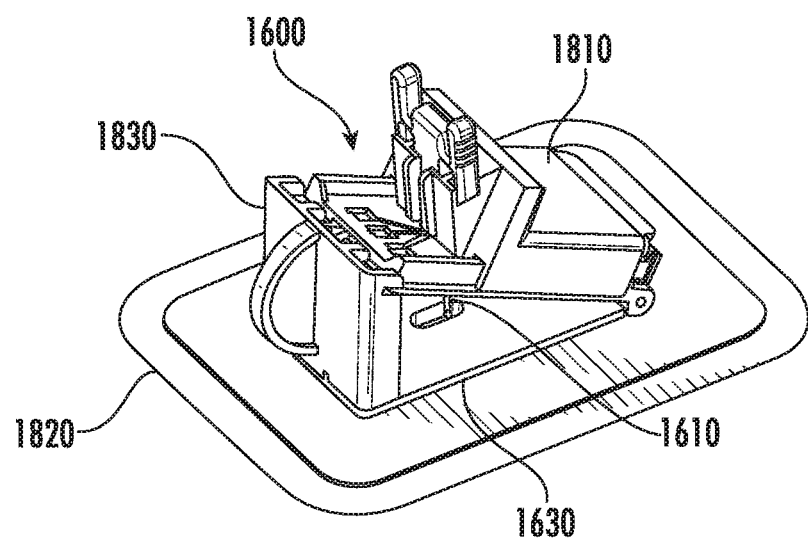
FIGS. 18A-18B are perspective views of the applicator of FIGS. 16A-16B as packaged, in accordance with some embodiments.
Figure 18B:
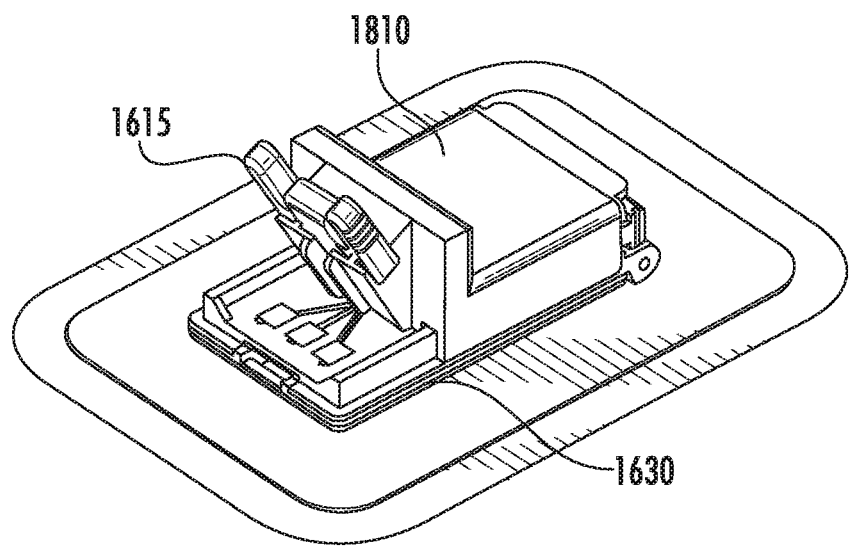

FIG. 17 is a perspective view of the body-worn components, where a cover 1697 includes circuit board 1698. FIG. 17 shows the device with the cover 1697 installed. FIG. 18A shows the hinged applicator 1600 as packaged (prior to needle deployment), where applicator 1600 is mounted on adhesive pad 1820. A spacer 1830 with an integrated lock feature keeps the applicator 1600 in an open state while packaged, to prevent needle 1610 from being deployed prior to being applied to the user. Although needle 1610 is not visible in these views, the needle is attached to tab 1615 which is accessible by the user. The needle and tab 1615 are held by front cover 1810. FIG. 18B shows the hinged suitcase design with the needle deployed, where the user has pressed down on cover 1810 so that it closed against platform 1630. Consequently, the needle 1610 has been moved through an opening in platform 1630, to subcutaneously insert a glucose sensor into the patient. The hinged design provides the user with a mechanical advantage so that the needle is easily inserted into the patient.

Figure 19:
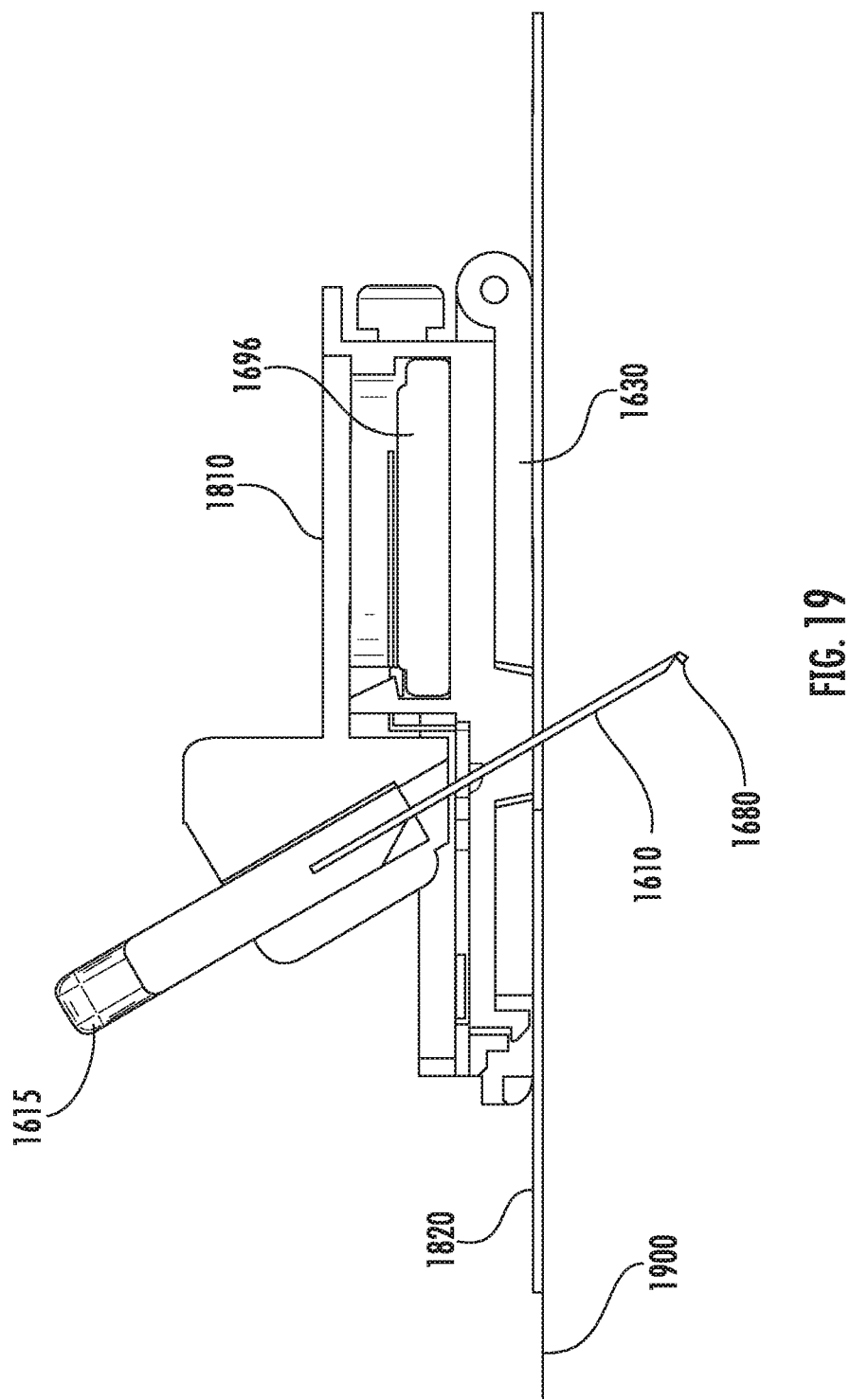
FIG. 19 is a cross-sectional view of the applicator of FIGS. 16A-16B with the needle deployed, in accordance with some embodiments.

FIG. 19 is a side cross-sectional view with the needle 1610 deployed, being inserted through patient's skin 1900 to deliver glucose sensor 1680. The needle 1610 with tab 1615 are still in place, along with front cover 1810. FIG. 19 also shows the relative location of the battery 1696 (same as battery 996) within the base.

Figure 20:
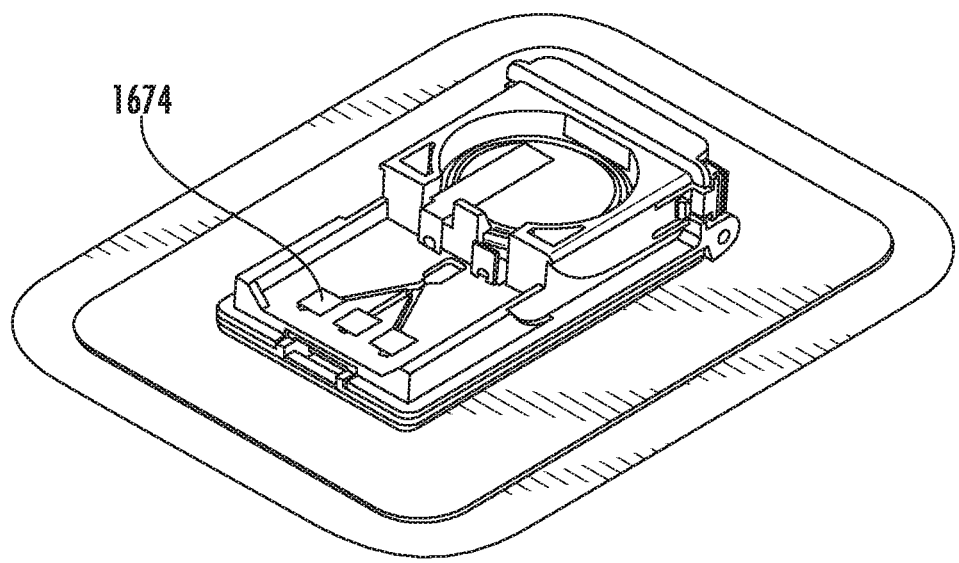
FIG. 20 is a perspective view of selected components of the hinged applicator, in accordance with some embodiments.
Figure 21:
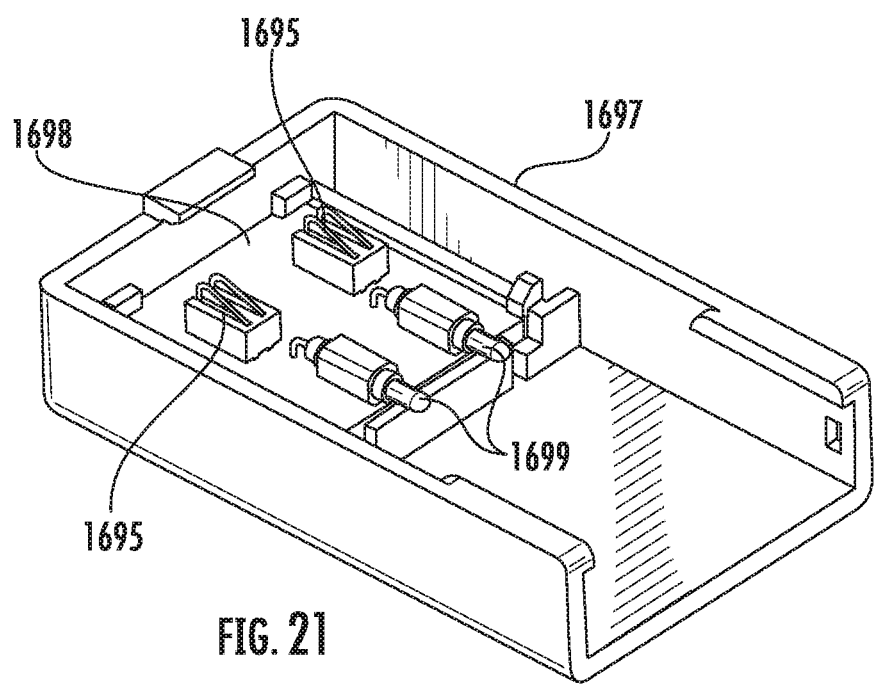
FIG. 21 is a perspective view of a cover of the hinged applicator, in accordance with some embodiments.

FIG. 20 is a perspective view of selected components of the base assembly, including contact pads 1674. FIG. 21 is a perspective view of the interior of cover 1697, which includes circuit board 1698. Contact pads 1674 provide electrical connection to the lead wires of the glucose sensor and are connected via compression connectors 1695 to the circuit board 1698. Additional pin style connectors 1699 on the circuit board 1698 make contact to the battery 1696 that is also located within the base.

Figure 22:
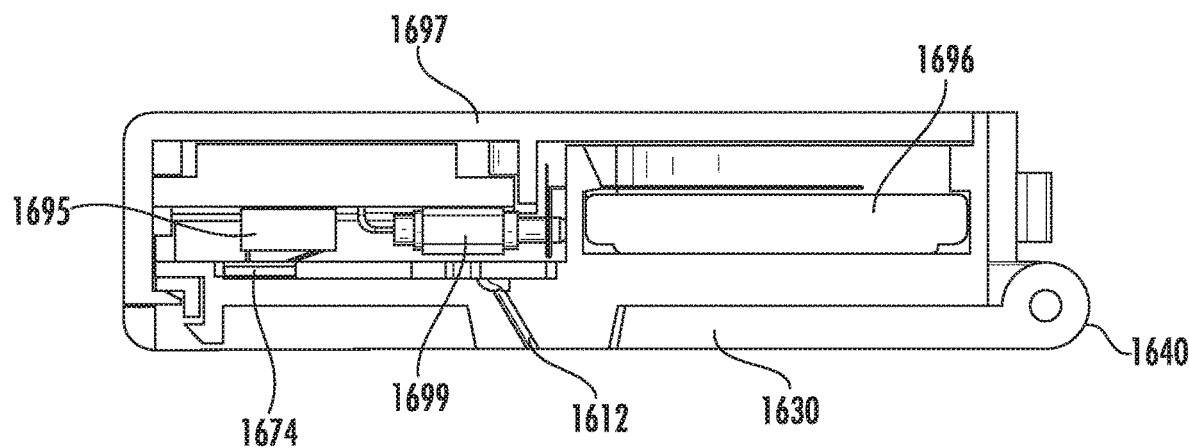
FIG. 22 is a cross-sectional view of the hinged applicator in a closed state, in accordance with some embodiments.
Figure 23:
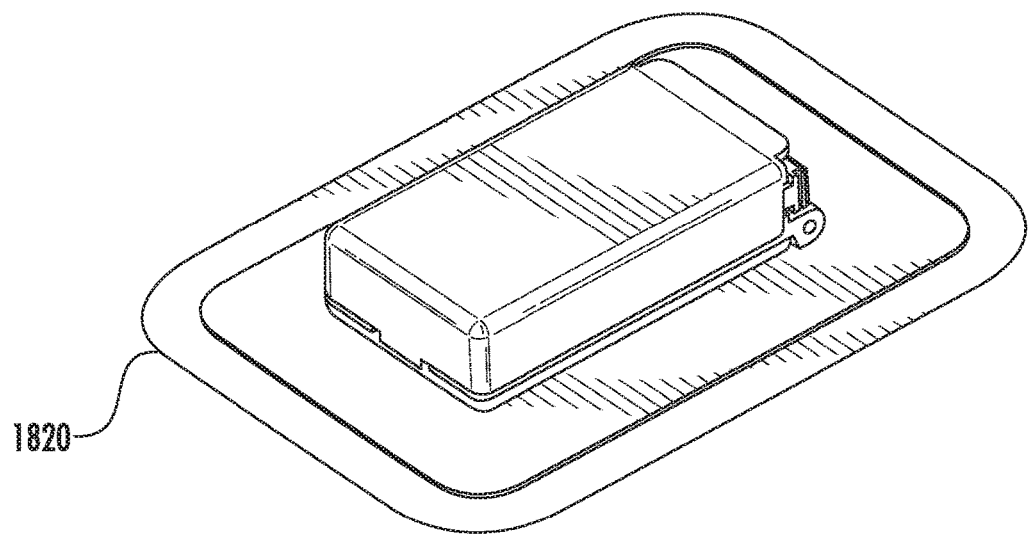
FIG. 23 is a perspective view of the hinged applicator in a closed state, in accordance with some embodiments.

FIG. 22 is a cross-sectional view of the body-worn device with the needle removed. Channel 1612 is a passageway through which the needle was inserted. Battery 1696 is shown, which provides power to the circuit board and sensor. FIG. 22 also shows the compressed states of the connectors 1695 and 1699 to both the sensor pads 1674 and the battery 1696 contacts. FIG. 23 is a perspective view of FIG. 22 showing the applicator after the sensor has been implanted, in its body-worn state via adhesive pad 1820.

The electrical connections between the sensor and the device circuitry will now be described, which can be used with the applicator embodiments above. Embodiments of the applicator device uniquely use a slotted needle that allows movement of the needle into and out of the skin without moving the wires that are attached to the sensor. Conventional slotted needles typically have the sensors bonded to the circuit boards, in contrast to the sliding "flag" contact mechanisms of the present disclosure. Embodiments also include unique configurations for forming and assembling wire contacts that enable low-cost, compact designs conducive to large-scale manufacturing. The wire contacts in some embodiments have a "flag" design that allow the wire contacts and sensor to be disposable components rather than being hard-wired to the long-term, durable circuit board of the overall device. The wire contacts have contact areas which the device's circuit board can be placed in electrical contact with, without bonding. Thus, the circuit board (e.g., device transceiver) can be reused, while the sensor and wire contacts can be single-use components.

Figure 24C:
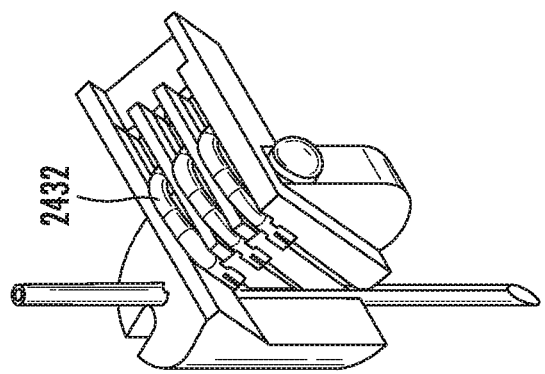
FIGS. 24A-24C are perspective views of a wire connection assembly, in accordance with some embodiments.
Figure 24B:
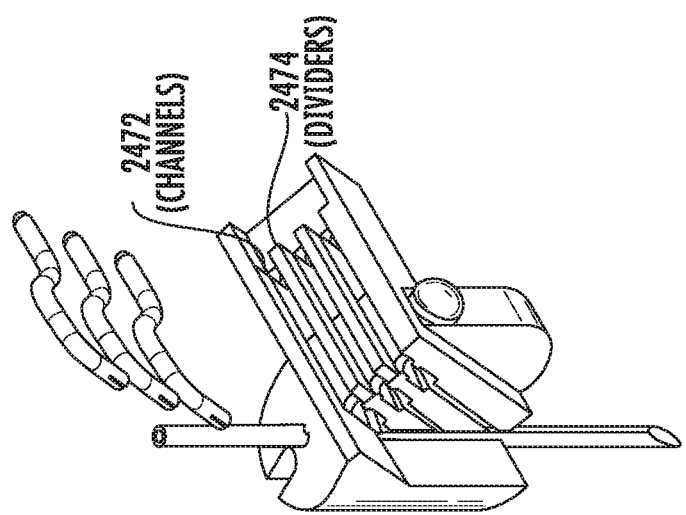
Figure 24A:
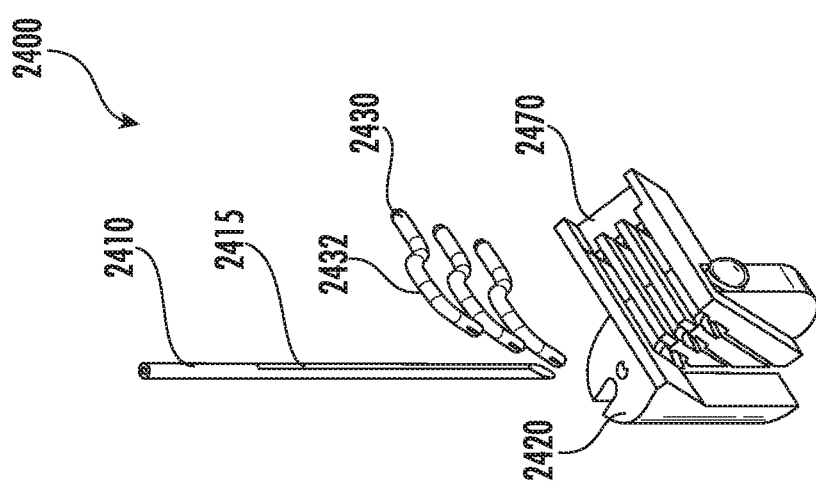

FIGS. 24A-24C are perspective views of a wire connection assembly 2400 with "flag" shaped wire contacts. A needle support 2420 is shown, through which needle 2410 is inserted and to which sensor base 2470 is attached. Needle 2410 has a slot 2415 along its length, through which the sensor's lead wires are run. Wire contacts 2430 have a contact area 2432 and are placed into channels 2472 of sensor base 2470. Because of the presence of three connection wires for the 3-pole sensor design and a limited amount of space in the overall device, the thickness of dividers 2474 between channels 2472 may be small, for example from 0.010" to 0.020", such as 0.015". These small dimensions can be problematic for manufacturing tolerances of the sensor base 2470 and for assembling the wires 2430 into the device.

Figure 25C:
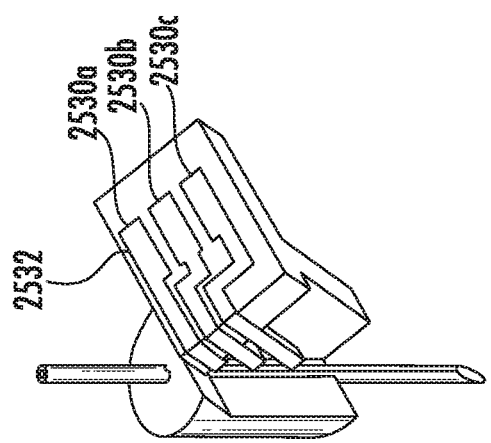
FIGS. 25A-25C are perspective views of a wire connection assembly with formed contacts, in accordance with some embodiments.
Figure 25B:
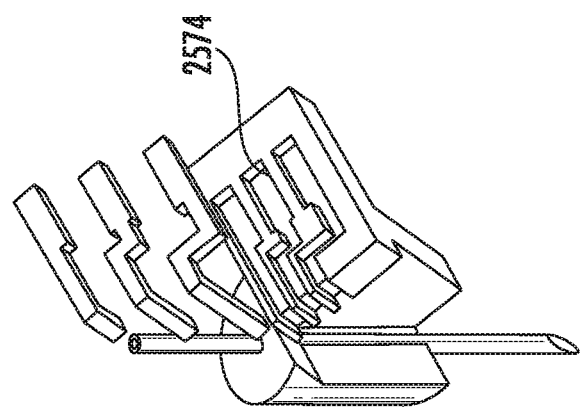
Figure 25A:
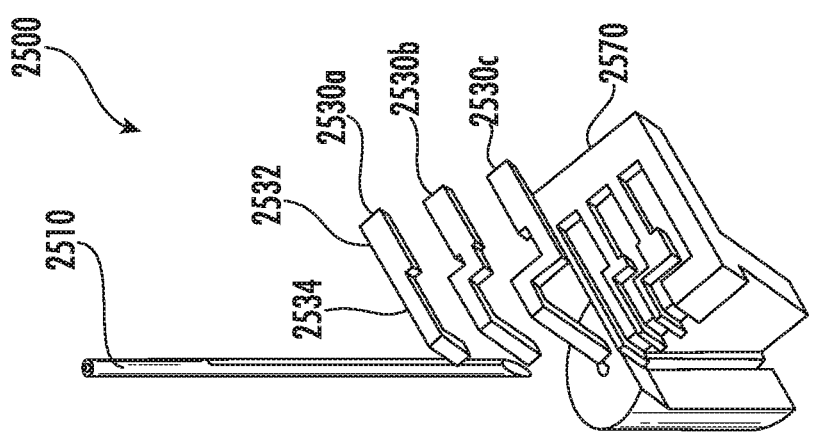

FIGS. 25A-25C show another embodiment of a wire connection assembly 2500 with flag-shaped formed contacts 2530a, 2530b, and 2530c instead of wire contacts 2430. Needle 2510 is slotted as described previously. The formed contacts 2530a/b/c are pre-formed metal components instead of wires, and each contact 2530a/b/c has an arm 2534 that ends in contact area 2532. As can be seen, the shape of the arms 2534 is different for each contact 2530a, 2530b, and 2530c in order to space the contact areas 2532 apart on the sensor base 2570. Contact 2530a has a straight arm 2534, contact 2530b has a small L-shaped arm, and contact 2530c has a larger L-shaped arm. The space 2574 between the three contact areas 2532 in the sensor base 2570 can be tailored by the shape of the arms 2534.

In use, sensor wires are attached to the arms 2534 at the end opposite of the contact areas 2530a/b/c. The wires may be attached by, for example, crimping, soldering, conductive adhesive, or the like.

FIG. 26 shows the wire connections in a device assembly, where sensor wires 2630 are routed through needle 2610 to be attached to sensor base 2670. The sensors (not visible in this figure) are at the opposite ends of the sensor lead wires 2630 and are made of electrodes having a flat surface design as described in FIGS. 1-3. The sensors are delivered subcutaneously by slotted needle 2610. Thus, the needle 2610 can retract into the device, as indicated by arrow 2615, while the sensor remains implanted since the sensor wires are fixed to sensor base 2670, which becomes locked into the base of the device.

FIG. 27 shows an embodiment of fabricating the formed contacts of FIGS. 25A-25C using printed circuit board components. In FIG. 27, three contacts are shown when using a 3-pole design: bottom contact 2730a having an L-shaped arm, middle contact 2730b having an inverse L-shaped arm, and top contact 2730c having a straight arm. The designations of top, middle and bottom indicate the order in which the contacts will be stacked with respect to each other using locating holes 2780. Each contact has an arm 2734a/b/c and a contact area 2732a/b/c, where the contact areas 2732a/b/c are where the sensor wires will be connected to. In some embodiments when using a 2-pole design, the same technology may be employed but by using two contacts stacked together such as the bottom contact 2730a having an L-shaped arm and the middle contact 2730b having an inverse L-shaped arm. Each type of contact 2730a/b or 2730a/b/c can be made in large quantities using PCB manufacturing methods, such as sheet 2750a which shows a 10×10 perforated PCB grid of the bottom contact 2730a.

FIG. 28 shows the next step in connecting the contacts to the sensors. Sensor wires 2701 are attached to the PCB-style contacts 2730a/b or 2730a/b/c by, for example, spot welding or soldering to the arms 2732a/b (for 2-pole design) or 2734a/b/c (for 3-pole design), respectively of the contacts. The sensor wire attachment can be done in an automated manner, such as the row of ten 2755a shown for the bottom contacts 2730a where the sensor wires 2701 are welded or soldered on an automated assembly line.

Figure 29:
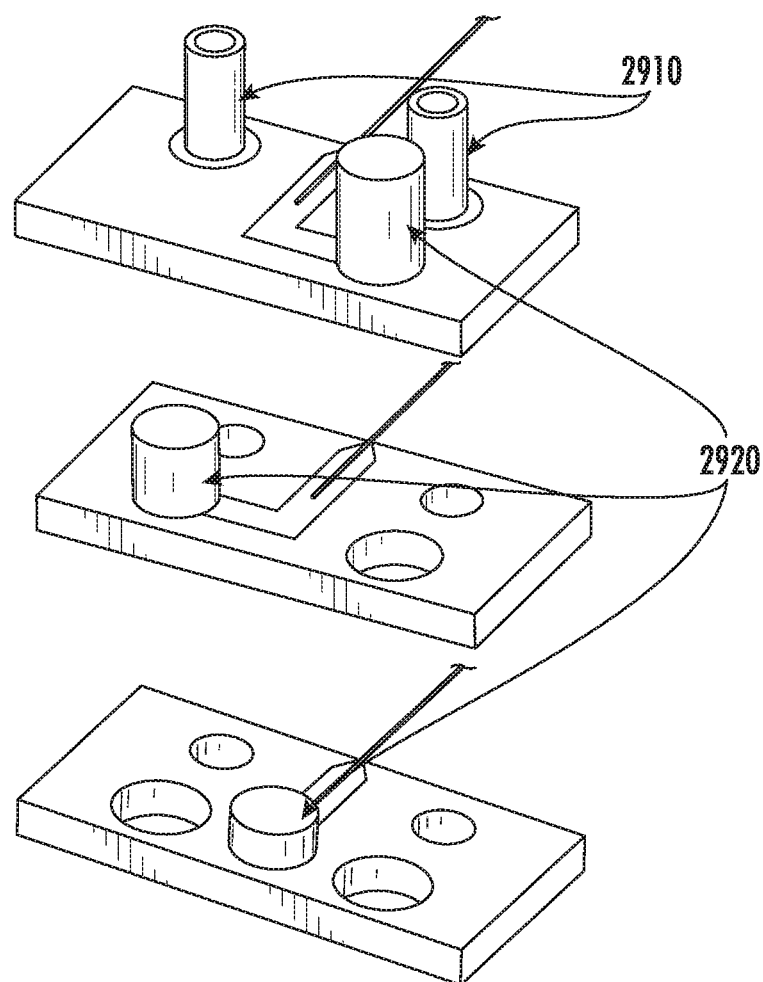
FIG. 29 shows the contacts of FIG. 27 in a further manufacturing stage, in accordance with some embodiments.

In FIG. 29, mounting or locating pins 2910 are attached to the PCB board, where the locating pins 2910 can also be receptacles or threaded inserts. A contact pin or pogo pin 2920 is attached to the contact areas 2732a/b or 2732a/b/c (FIG. 27) of the contacts.

Figure 30:
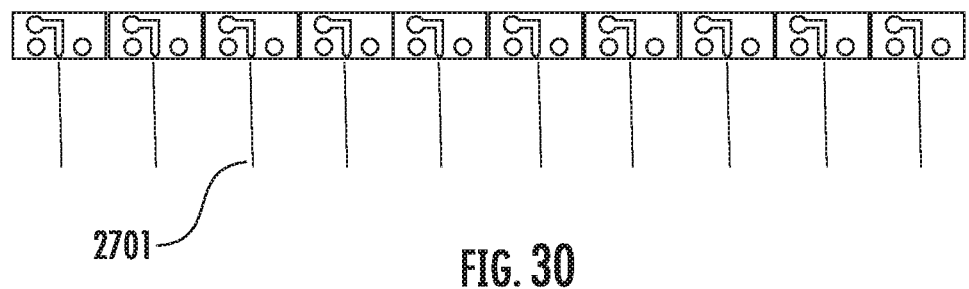
FIG. 30 shows a row of printed circuit board assemblies being coated, in accordance with some embodiments.

In FIG. 30, a coating application is performed. A row of printed circuit board assemblies (PCBAs) are attached to a cassette that coats the wire ends of sensor wires 2701. The contact on each of the PCBAs is attached to a monitoring program, and each wire/PCBA is measured and logged. The PCBAs can now be separated by quality and matched with the other wire/PCBAs for maximum yield or quality top-tier pricing.

Figure 31:
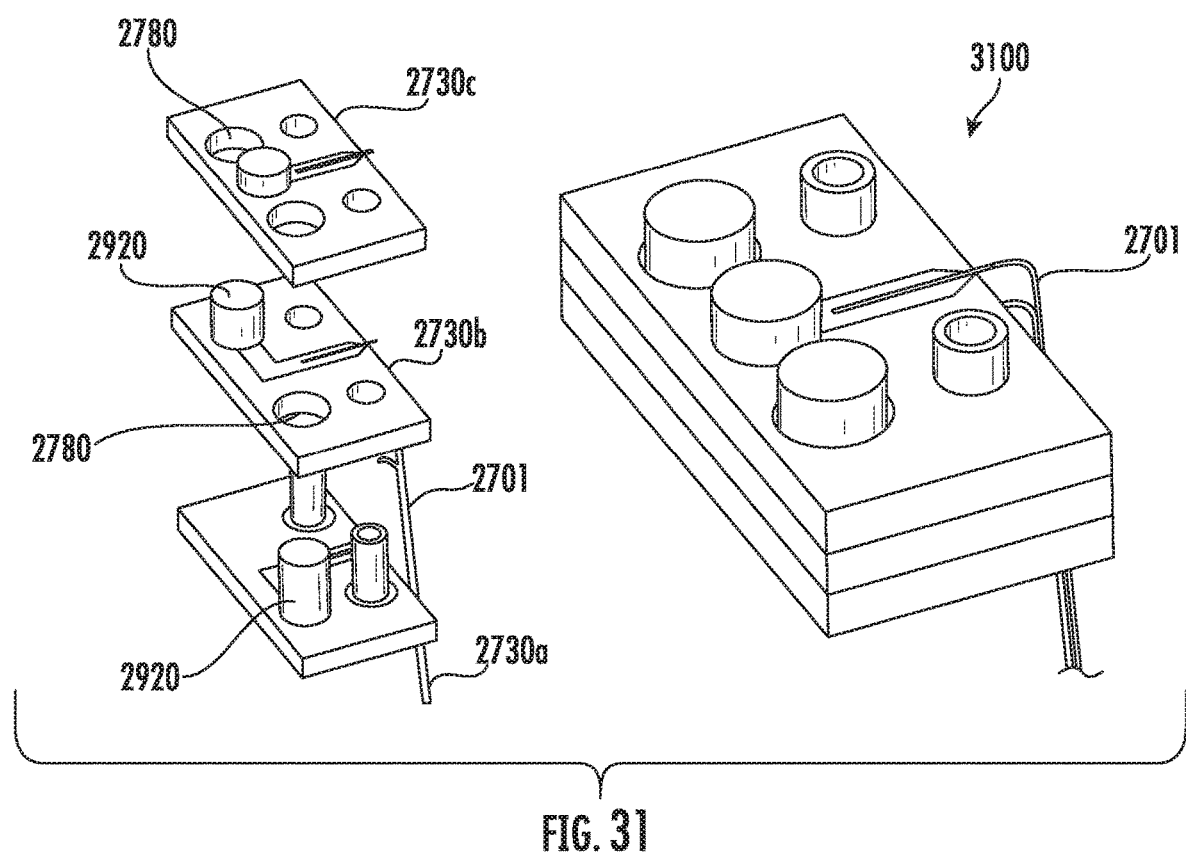
FIG. 31 shows the printed circuit board components of FIG. 27 being stacked into an assembly, in accordance with some embodiments.

In FIG. 31, the PCBAs are assembled. The set of two PCBAs 2730a/b—bottom and middle for a 2-pole design or the set of three PCBAs 2730a/b/c—bottom, middle and top for the 3-pole design—are stacked on each other by placing contact pins 2920 through locating holes 2780. As a result, each contact pin 2920 is accessible from the top of the assembled PCBA stack 3100 (where 3-pole design is shown in this illustration), for amperometric readings to be taken. The contact pins 2920 will make electrical connection to the device's circuit board transmitter (e.g., circuit board 440 or 998) via compression. The sensor wires 2701 are all centrally located on an edge of the PCBA stack 3100 and are vertically aligned for easy insertion of the sensor wires 2701 into the needle.

Figure 32A:
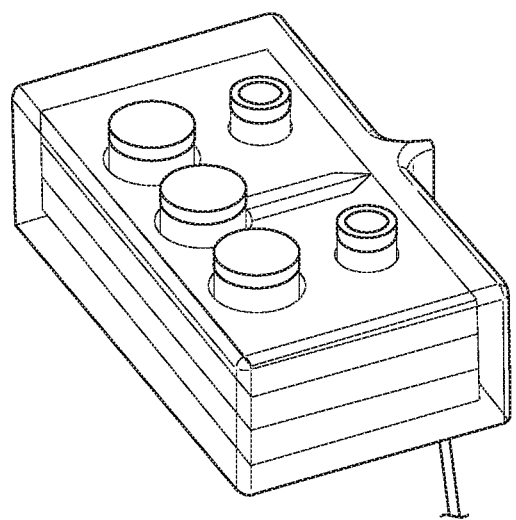
FIGS. 32A-32C are perspective views of sealed wire connection assemblies, in accordance with some embodiments.
Figure 32B:
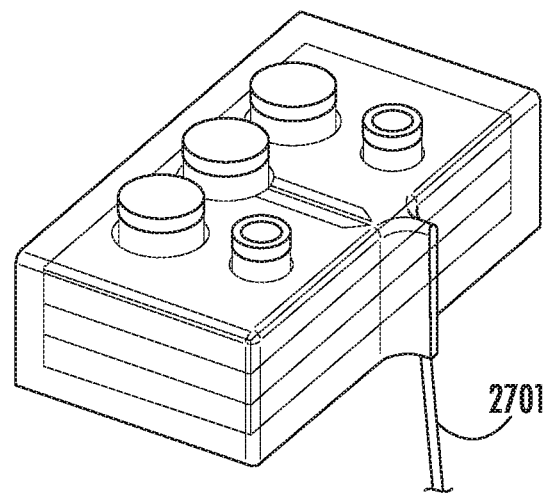
Figure 32C:
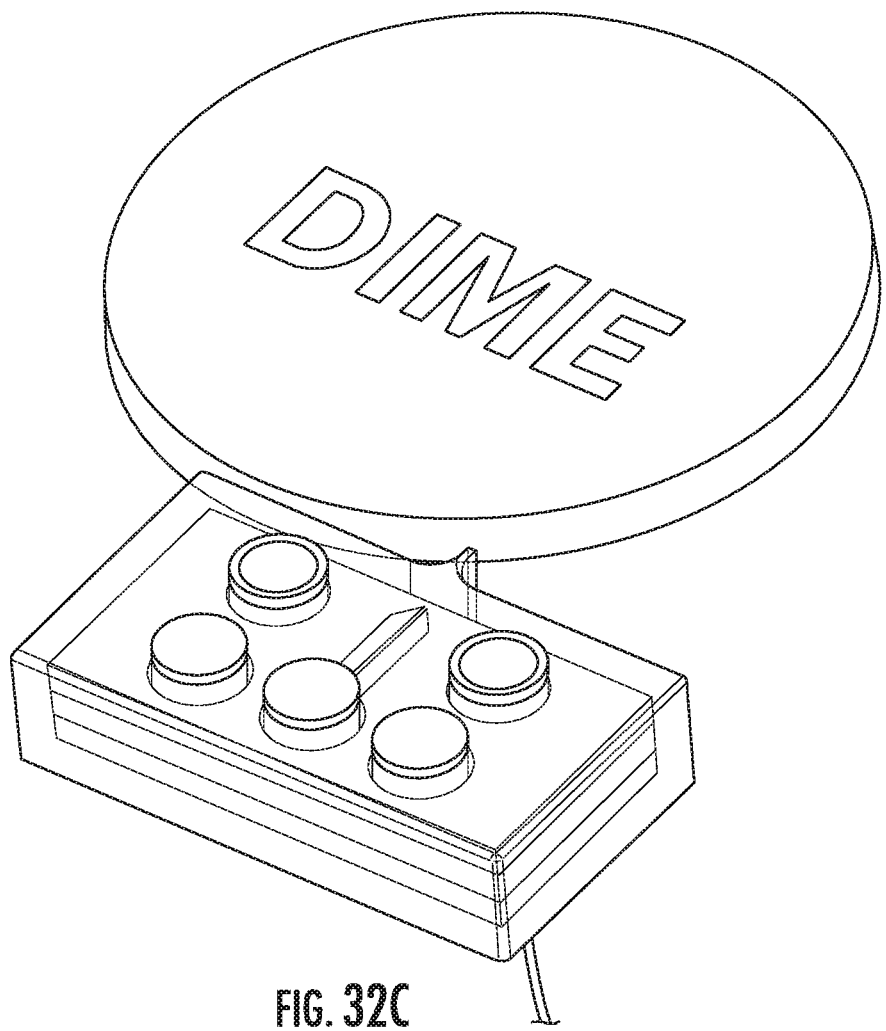

FIGS. 32A-32C show a wire/PCBA assembly sealed (e.g., dipped) in epoxy or other sealant, to protect the electrical connections. FIG. 32A is a front perspective view and FIG. 32B is a rear perspective view, showing that the connections of wires 2701 to the PCBA are also sealed. FIG. 32C shows a size comparison to a dime, where in this example embodiment the height of the finished wire connection PCB assembly is 0.013 inches, the width is 0.030 inches, and the length is 0.055 inches.

Advantages of this PCB style of wire connections include that the design shape of the contacts can be easily modified to accommodate original equipment manufacturer (OEM) variations such as round, square, and triangular. No injection molded parts are required, thus saving tooling costs. The overall design is low-cost with minimal assembly labor required, where the entire manufacturing process can be fully automated up to the sorting process. Wires can be coated in large quantities and measured or logged individually for quality. The components can be sorted and matched based on criteria such as quality, sensor performance or maximum yield. The PCB assemblies can also be sold as a stand-alone product. The "flag" mounting feature allows for a multitude of mounting options. The "flag" mounting can be done in a horizontal plane or in a vertical stack and this gives various options for assembly. Some embodiments of assembly methods may be easier to automate especially in the bonding of the wire to the "flag." Other embodiments of mounting styles may be easier to downsize the overall profile of the applicator.

Figure 33A:
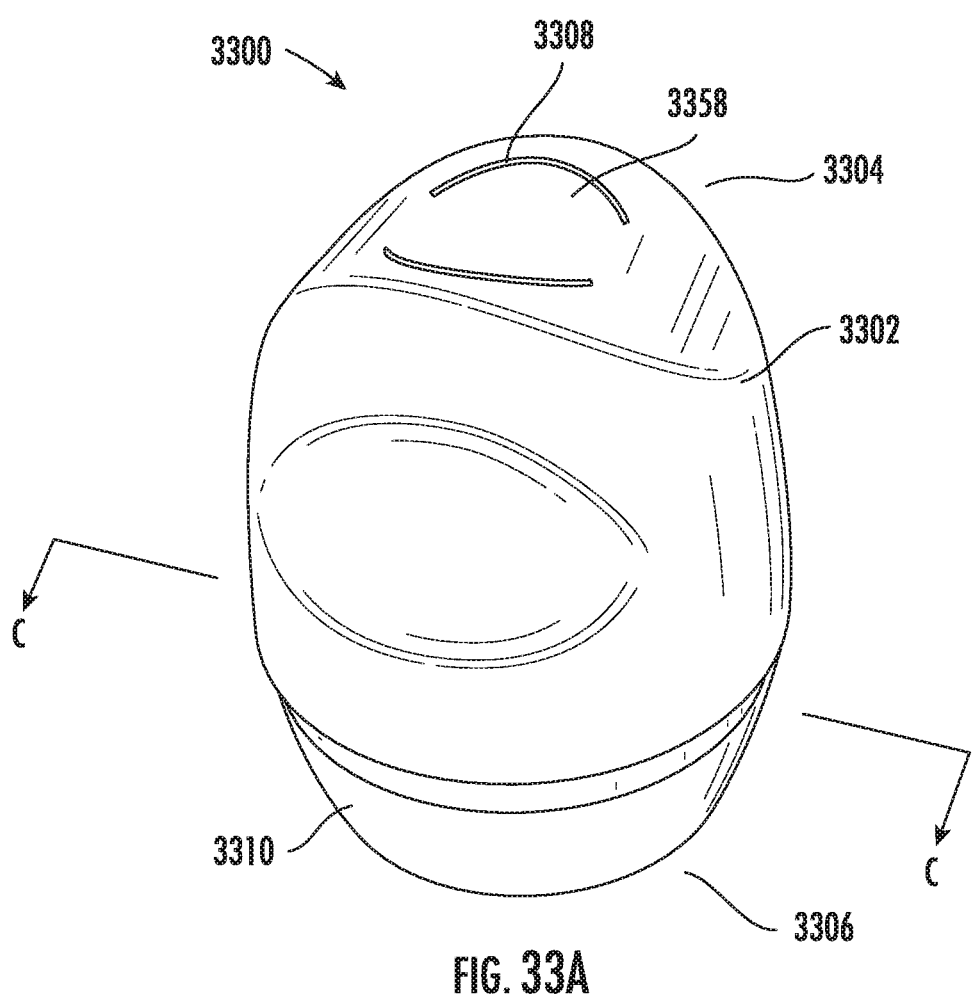
FIG. 33A shows a perspective view of an applicator for a glucose monitoring system, in accordance with some embodiments.

FIG. 33A shows a perspective view of an applicator for a glucose monitoring system, in accordance with some embodiments. The applicator 3300 has a vertical insertion method for implanting the sensor underneath the skin. To use the applicator 3300, the bottom surface of the applicator 3300 is placed on the skin of the patient and a downward force is applied on the top surface deploying a needle with the sensor for placing the sensor underneath the skin. After the sensor is implanted, the needle automatically retracts and the monitoring device is adhered to the skin, and the applicator including all of the components are disposable. As soon as the sensor is placed and the monitoring device is adhered to the skin, the monitoring device is ON and collecting data without input from the patient. The limited number of steps described—placing on the skin and pushing downward on the applicator—provides an easy, hassle-free, convenient method for glucose monitoring that is delivered in a sterile manner.

Figure 33B:
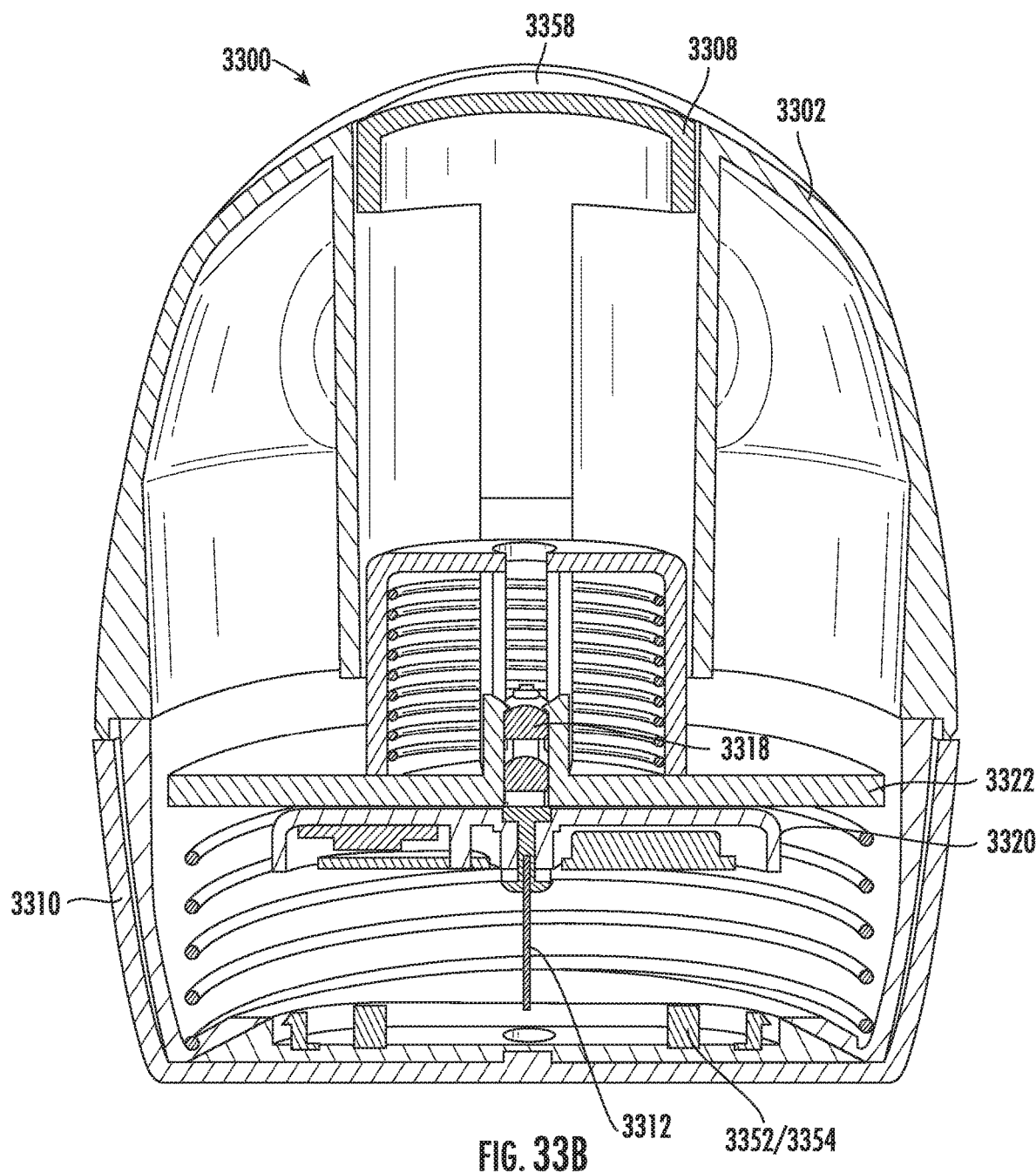
FIG. 33B is a vertical cross-sectional view of the applicator taken along section C-C of FIG. 33A.

The applicator 3300 includes a body 3302 with a top surface 3304 and a bottom surface 3306, and an actuator 3308 coupled to the body 3302 and extending through the top surface 3304 of the body 3302. A cap 3310 is removably coupled the bottom surface 3306 of the body 3302. FIG. 33B is a vertical cross-sectional view of the applicator 3300 taken along section C-C of FIG. 33A.

Figure 34:
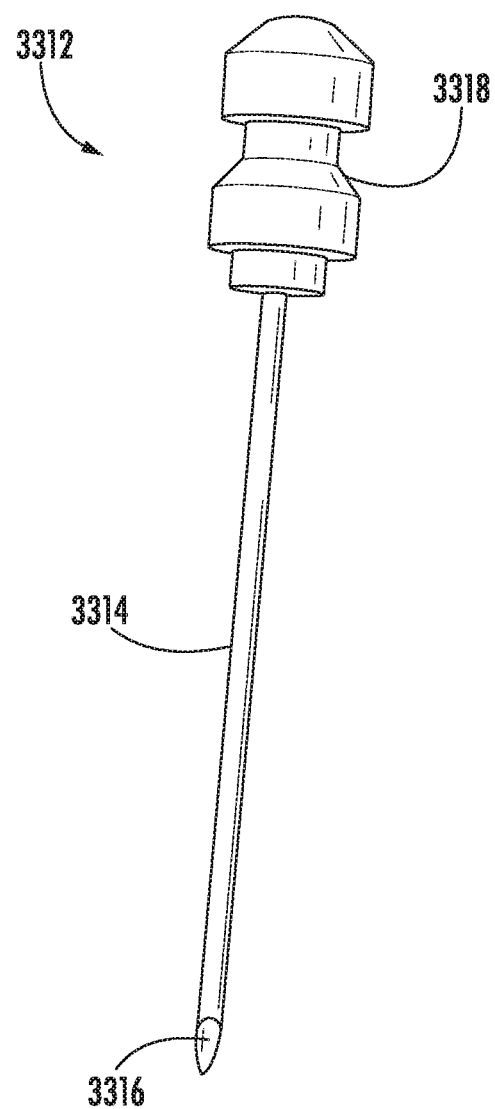
FIG. 34 is a slotted needle, in accordance with some embodiments.

A needle 3312 is mounted to the actuator 3308. FIG. 34 is a slotted needle 3312, in accordance with some embodiments. The needle has an inner diameter and a slot 3314 along a length of the needle to a tip of the needle 3316. The needle 3312 is coupled to a holder 3318 at the top of the needle 3312.

A sensor such as the 2-pole design or the 3-pole design (refer to FIGS. 1-3) is coupled to a plurality of wires 3328 (see FIGS. 35A-35B) at one end of the plurality of wires 3328. In a non-limiting example, the 2-pole design is illustrated so that the sensor includes a working electrode and a reference electrode. The sensor and the plurality of wires 3328 are sized to fit through the inner diameter of the needle 3312.

Figure 35A:
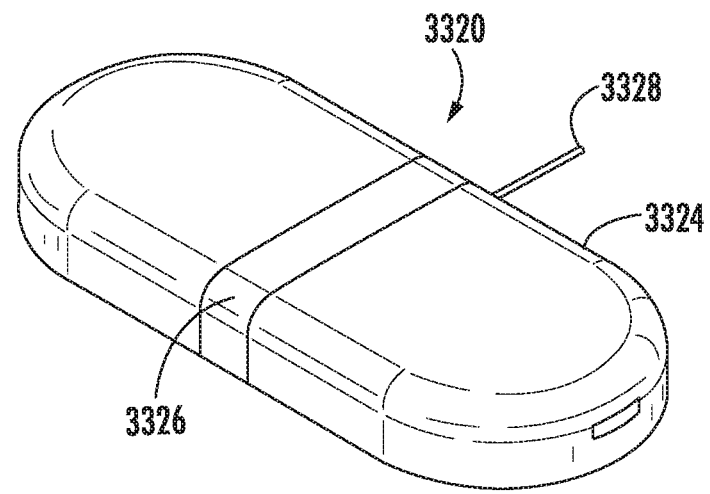
FIGS. 35A and 35B show a base of the applicator, in accordance with some embodiments.
Figure 35B:
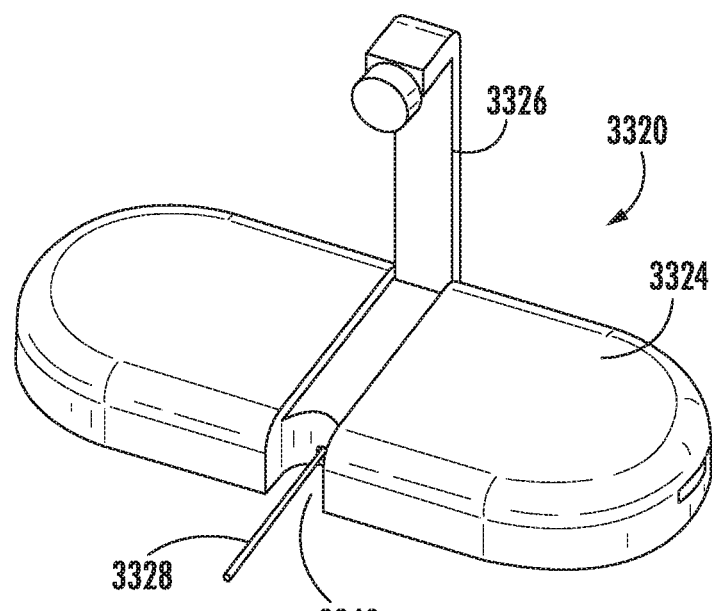

A base 3320 is configured to be moveable by the actuator 3308 and coupled to a plate 3322. The plate 3322 is configured to be moveable by the actuator 3308 and may be part of the actuator 3308. FIGS. 35A and 35B show a base 3320 of the applicator 3300, in accordance with some embodiments. The base has an upper housing 3324 and a tab 3326. The tab 3326 has a closed position as shown in FIG. 35A and an open position as shown in FIG. 35B. The base 3320 and tab 3326 may be comprised of an elastomeric material such as silicone or urethane. The base 3320 has a cutout 3340 which the needle 3312 moves through. The plurality of wires 3328 extend through the upper housing 3324 of the base 3320.

Figure 36A:
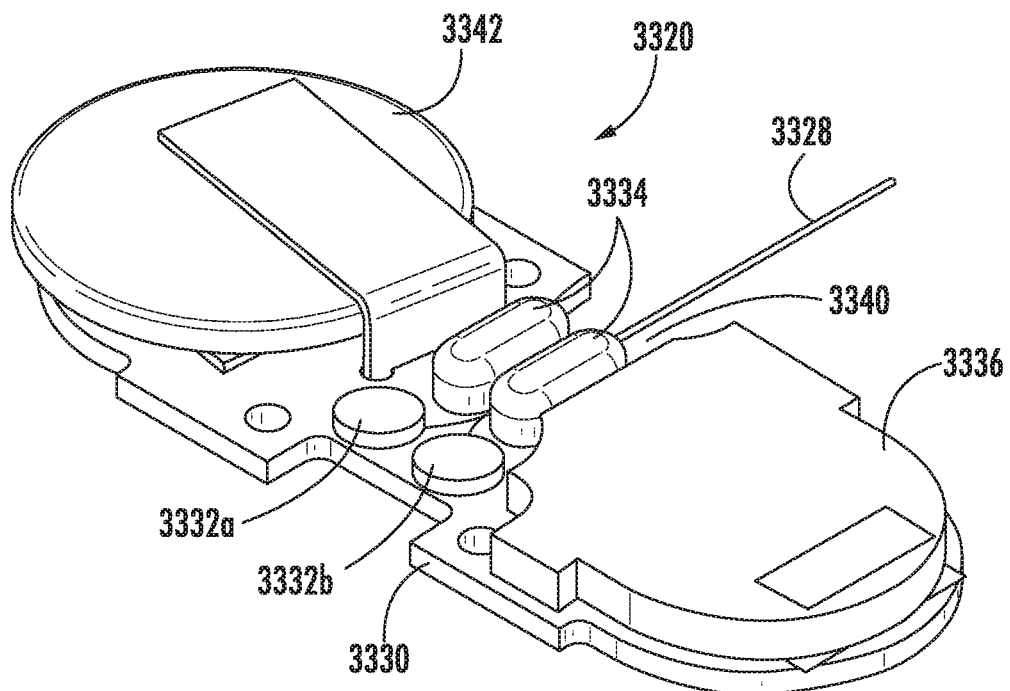
FIGS. 36A and 36B show the internal components of the base of the applicator, in accordance with some embodiments.
Figure 36B:
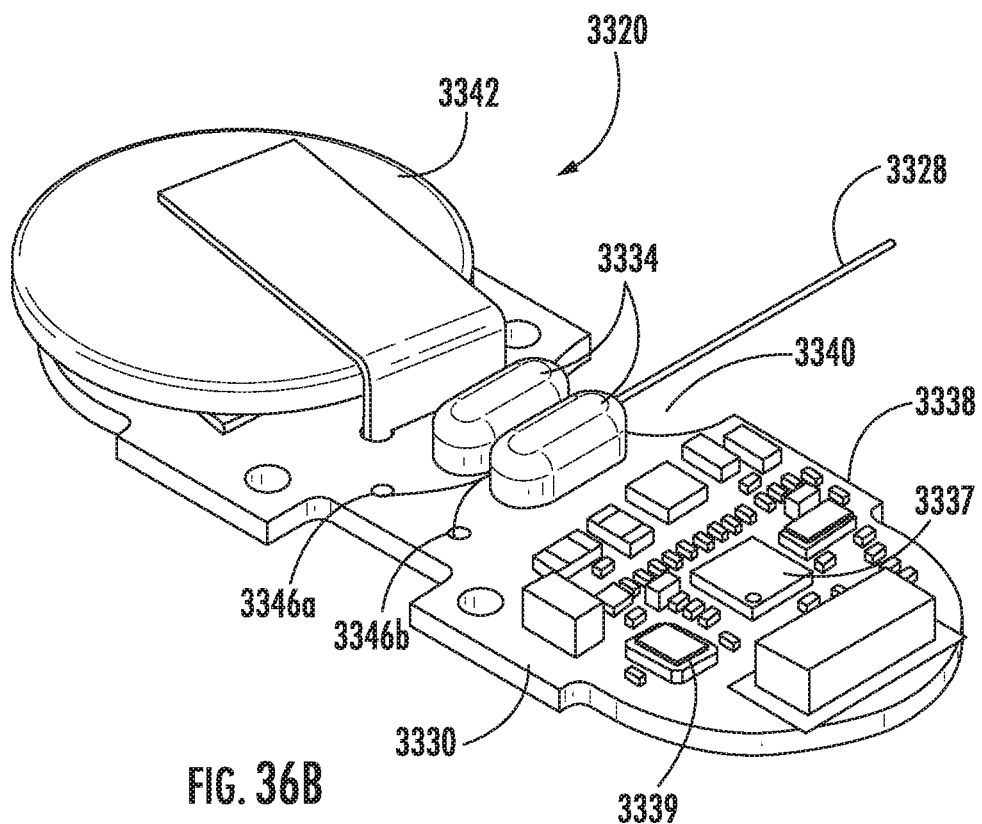

FIGS. 36A and 36B show the internal components of the base 3320 of the applicator 3300, in accordance with some embodiments. The upper housing 3324 is removed from the base 3320 in this illustration and a circuit board 3330 is shown. The circuit board 3330 has a plurality of contacts, such as 3332a and 3332b, and each contact 3332a/b is coupled to a wire of the plurality of wires 3328. A wire guide 3334 is coupled to the circuit board 3330 and aligns, routes and holds the plurality of wires 3328 in place while on the circuit board 3330. A component cover 3336 protects various components 3338, such as a microprocessor 3337, a transmitter 3339 and circuitry on the circuit board 3330. The cutout 3340 on the circuit board 3330 matches and corresponds to the cutout 3340 of the base 3320 and provides access through the base 3320 and the circuit board 3330. A power source 3342, such as a battery, is electrically connected to the circuit board 3330 and coupled to the base 3320 to supply power to the system. The power source 3342 may be a low-profile lithium cell battery.

Figure 37:
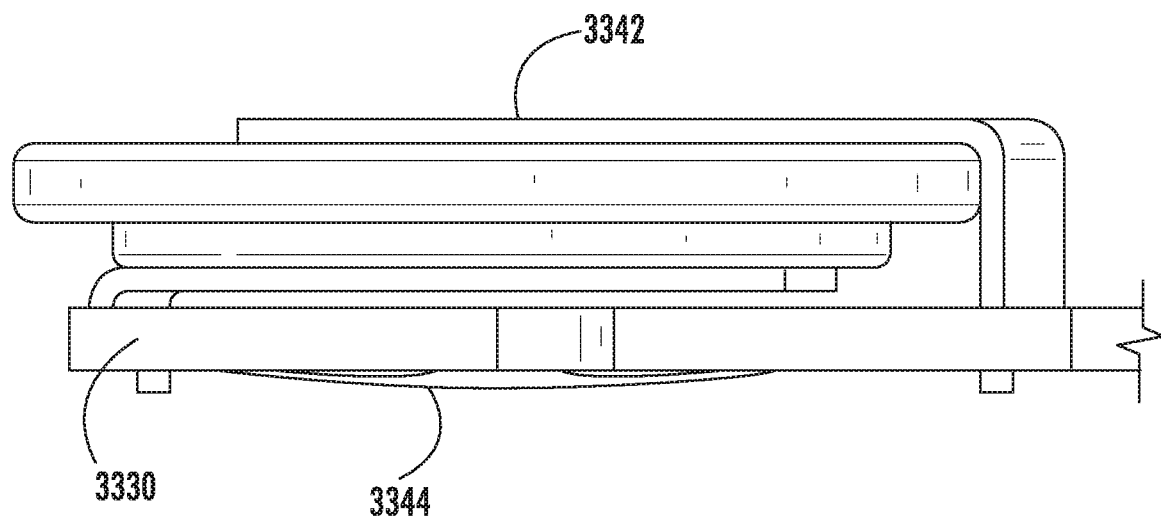
FIG. 37 shows a cutaway front view of the circuit board with the power source, in accordance with some embodiments.

FIG. 37 shows a cutaway front view of the circuit board 3330 with the power source 3342, in accordance with some embodiments. The power source 3342 has a switch 3344 mounted on the underside of the circuit board 3330. This enables the power source 3342 to be activated or turned on at will such as at the beginning of the monitoring session instead of always being in an ON position.

Figure 38:
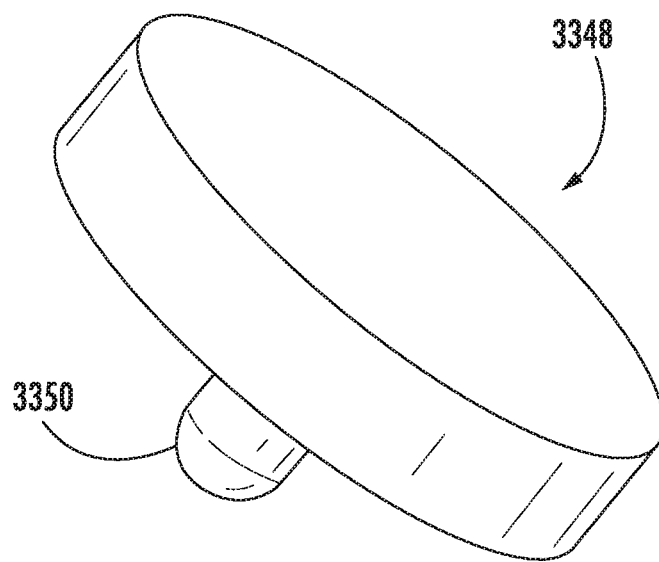
FIG. 38 shows a perspective view of a fastener of the contact, in accordance with some embodiments.

The plurality of contacts 3332, for example, 3332a/b, each includes an opening 3346a and 3346b (shown on FIG. 36B) of a plurality of openings 3346 on the circuit board 3330. The plurality of openings 3346, such as 3346a/b, each have a metal coating on the inner diameter of the opening such as gold-plating which is part of the circuitry. Other types of metal coating may be used such as silver, nickel, rhodium, or platinum. FIG. 38 shows a perspective view of a fastener 3348 of the contact 3332a/b, in accordance with some embodiments. A fastener 3348 has a protrusion 3350, and a diameter of the protrusion 3350 is less than a diameter of the opening 3346a/b so that the protrusion 3350 fits into the opening 3346a/b. The fastener 3348 is made to have a thin, low-profile so the portion of the fastener 3348 that extends from the circuit board 3330 (not the protrusion 3350) is less than 0.1 inches. This enables the base 3320 to also have a thin, low-profile. The wire of the plurality of wires 3328 is between the opening 3346a/b and the protrusion 3350. The protrusion 3350 is sized such that it forces the wire of the plurality of wires 3328 against the metal coating in the opening 3346a/b thus enabling the electrical connection between the wire of the plurality of wires 3328 and the circuit board 3330. In this way, the sensor of the applicator 3300, via the plurality of wires 3328, is hardwired to the circuit board 3330 at the plurality of contacts 3332. The plurality of wires 3328 and the plurality of contacts 3332 are located within the base 3320. In applicator 3300, the sensor, the power source 3342 and the circuit board 3330 are contained within the body 3302. The fastener 3348 may be comprised of a silicone, composite, metal or combination thereof and secured in the opening 3346 by a press-fit or push-fit, or soldering, micro-welding and or conductive adhesives.

Figure 39A:
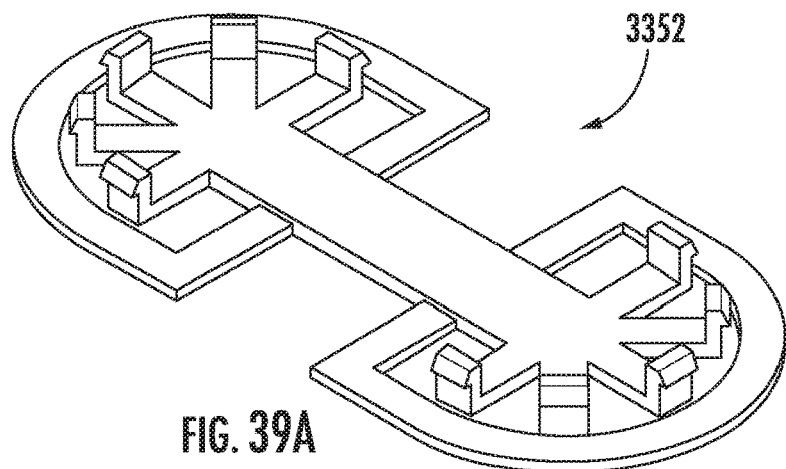
FIGS. 39A-39C show perspective views of the bracket and the patch respectively, in accordance with some embodiments.
Figure 39B:
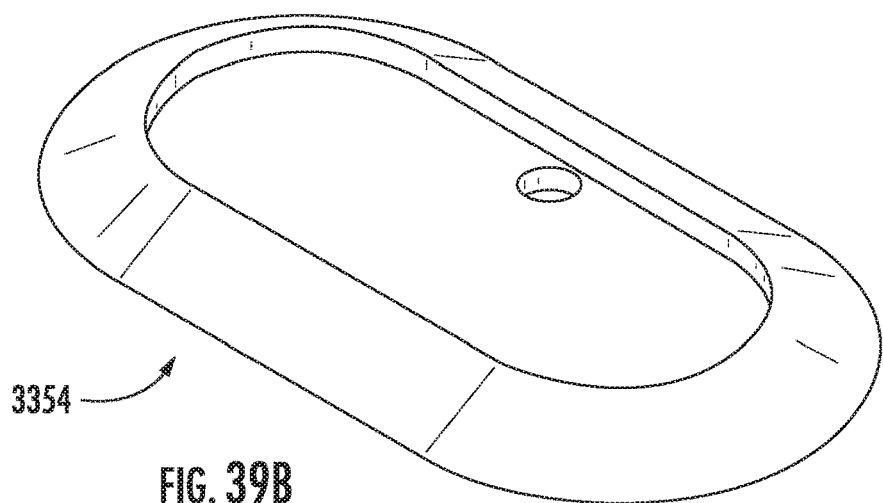
Figure 39C:
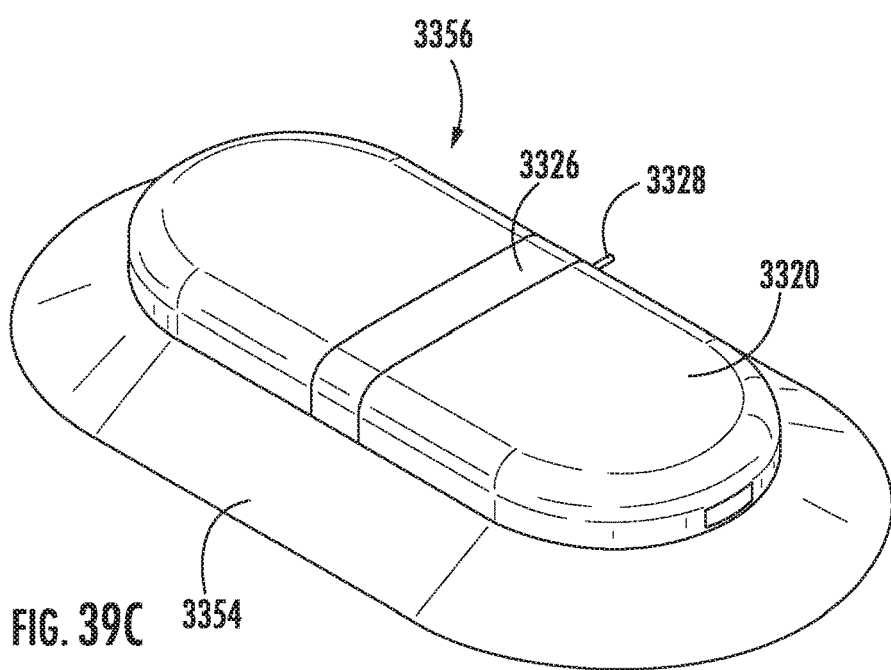

Referring to FIG. 33B, a bracket 3352 is coupled to the bottom surface 3306 of the body 3302 and configured to receive the base 3320. The bracket 3352 may be comprised of a rigid polymer such as polycarbonate, PVA or nylon. A patch 3354 is coupled to the bracket 3352 on the top side of the patch 3354 and has an adhesive on the bottom side of the patch 3354. In some embodiments, the bracket 3352 fits inside of the patch 3354. FIGS. 39A-39B show perspective views of the bracket 3352 and the patch 3354 respectively, in accordance with some embodiments. The base 3320 is received in the bracket 3352. FIG. 39C depicts the base 3320 in the bracket 3352 with the patch 3354, which is a wearable device 3356.

Figure 40A:
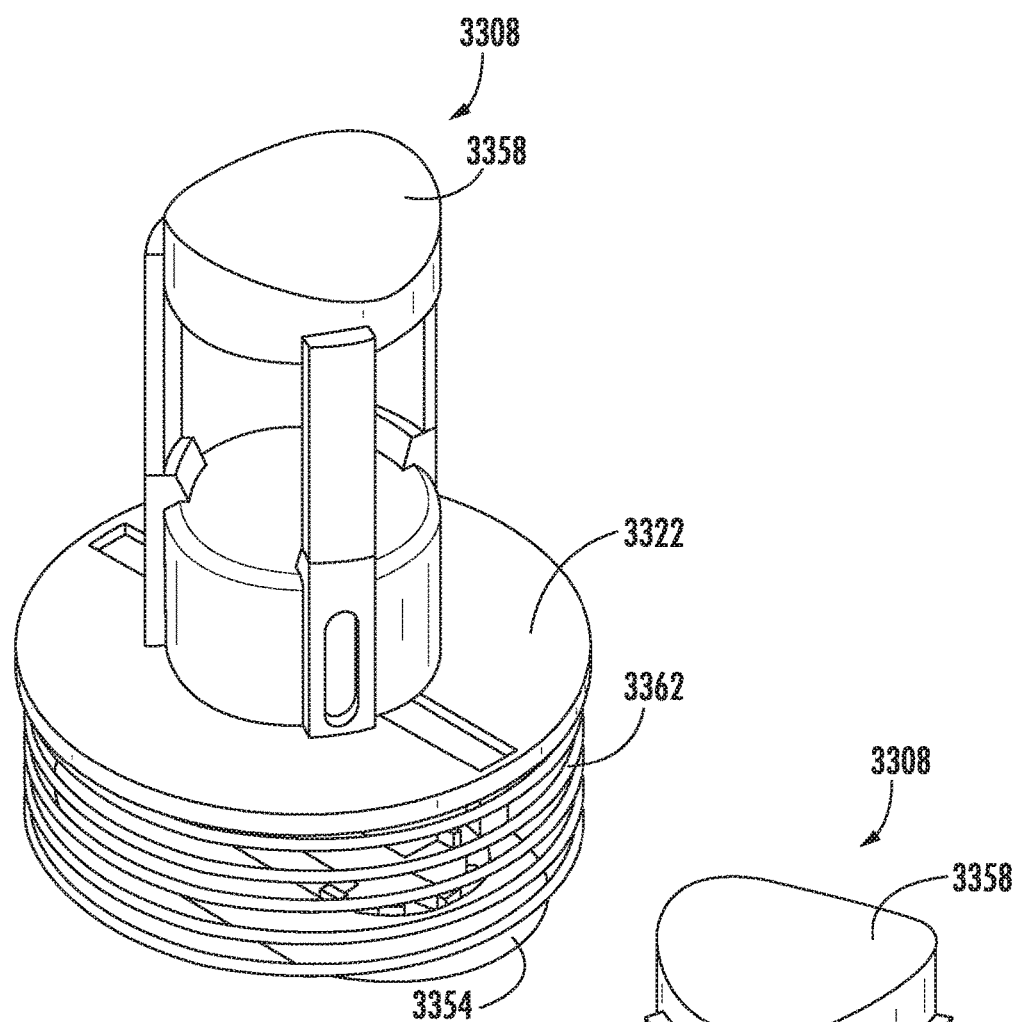
FIGS. 40A and 40B depict perspective views of the actuator, in accordance with some embodiments.
Figure 40B:
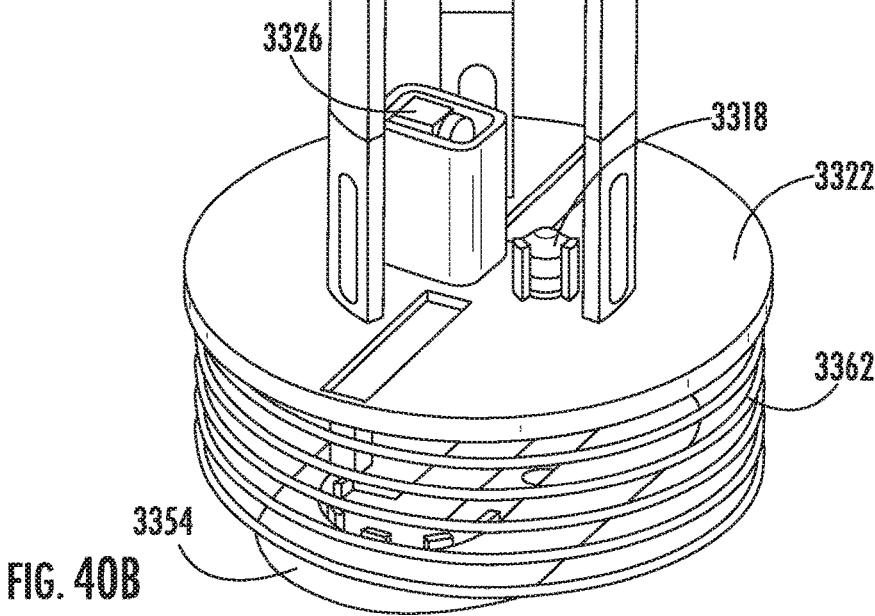
Figure 40C:
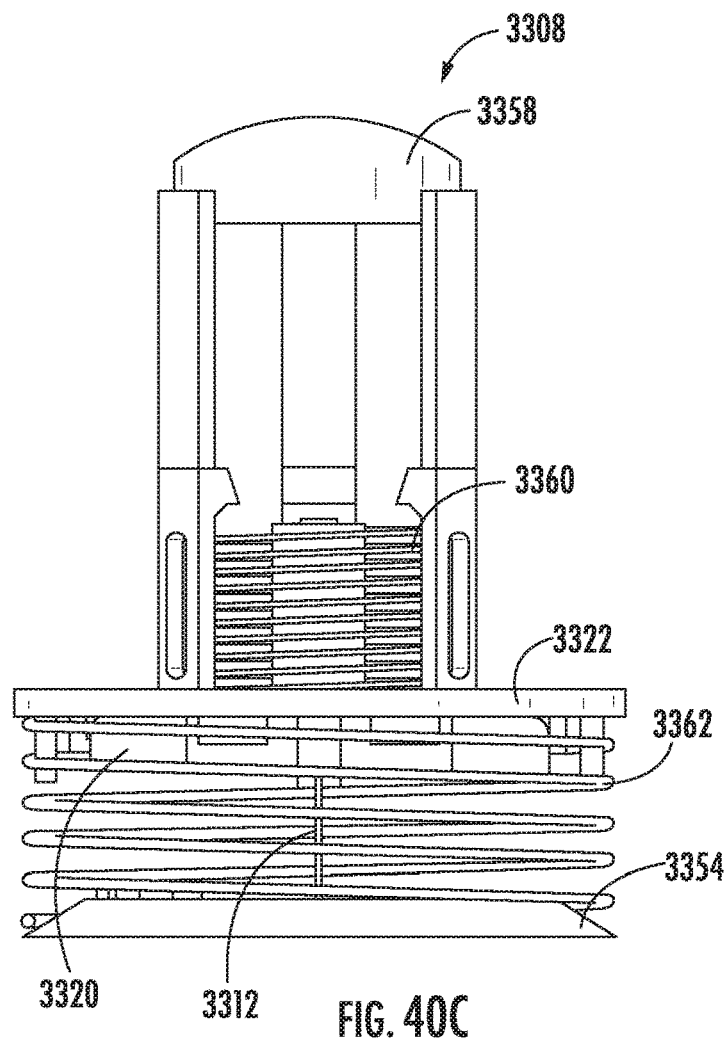
FIG. 40C shows a front view of the actuator, in accordance with some embodiments.

FIGS. 40A and 40B depict perspective views of the actuator 3308, in accordance with some embodiments, and FIG. 40C shows a front view of the actuator 3308, in accordance with some embodiments. In some embodiments, the actuator 3308 includes a button 3358, and a first spring 3360 located above the plate 3322 and having a first uncompressed length and a first compressed length. The plate 3322 is coupled to the first spring 3360, the base 3320 and the needle 3312 (via holder 3318). A second spring 3362 is located below the plate 3322 and coupled to the plate 3322. The second spring 3362 has a second uncompressed length and a second compressed length. The actuator 3308 may be activated when the user desires glucose monitoring. In typical systems, the sensor is implanted underneath the skin and a wearable device in communication with the sensor is worn on the skin.

The applicator 3300 is ready to use 'as is'. There are no preliminary steps such as connecting the sensor to electronics, power source or wearable device. To use the applicator 3300, the bottom surface 3306 of the applicator 3300 may be abutted on the skin of the user and the actuator 3308 is activated by applying a downward force on the top surface 3304 of the body 3302 such as on the button 3358. The first spring 3360 moves from the first uncompressed length to the first compressed length, the second spring 3362 moves from the second uncompressed length to the second compressed length while the plate 3322, the base 3320—including the circuit board 3330, the plurality of contacts 3332 coupled to the plurality of wires 3328, the power source 3342—and the needle 3312 are moved in a downward direction toward the bottom surface 3306 of the body 3302 and into the bracket 3352 coupled to the patch 3354. The needle 3312 is configured to be moveable by the actuator and travels through the cutout 3340 on the base 3320. The plurality of wires 3328 with the sensor at one end extend from the base 3320, through the needle 3312 and out of the slot 3314 of the needle 3312.

The mating of the base 3320 into the bracket 3352 and patch 3354 activates the switch 3344 to the power source 3342 and turns the system ON which confirms the system is deployed on the skin. For example, the switch 3344 is mounted on the bottom side of the circuit board 3330 so that when the switch 3344 contacts the bracket 3352 during actuation, the switch 3344 is depressed and the electrical connection is made to the circuit board 3330 and thus, the power source 3342. The ability to turn the power source 3342 ON in contrast to having the device always ON is unconventional. In known systems, the power source, e.g., the battery, is always ON so a larger, more powerful battery is needed thus having a large footprint making the design bulky and uncomfortable. In other known systems, the battery may be manually activated by when connecting the sensor to the electronics in the wearable device.

Figure 41:
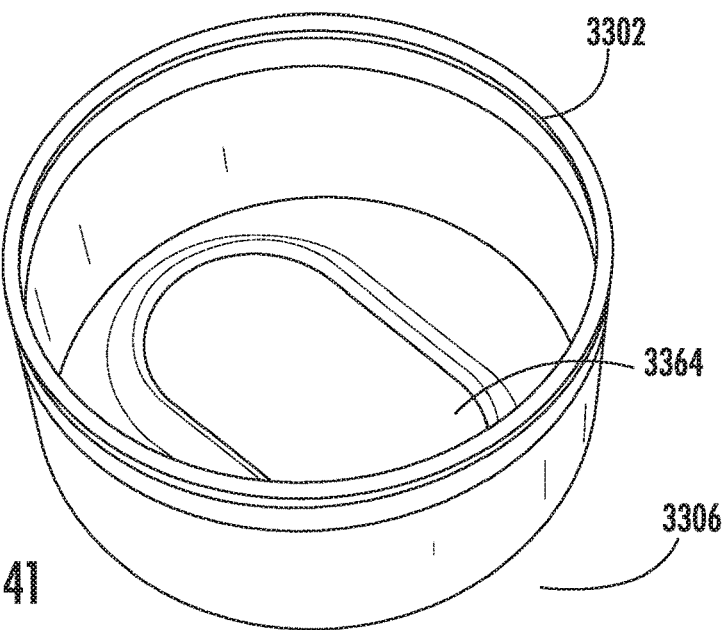
FIG. 41 is a perspective view of the bottom surface of the body, in accordance with some embodiments.

FIG. 41 is a perspective view of the bottom surface 3306 of the body 3302, in accordance with some embodiments. The bottom surface 3306 of the body 3302 has a hole 3364 which the patch 3354 is removably attached to and configured to slide through. Due to the force applied on the button 3358 of the actuator 3308 and the compression of the first spring 3360 and the second spring 3362, the patch 3354 with the attached base 3320 in the bracket 3352, is forced out of the hole 3364 of the bottom surface 3306 of the body 3302 and adhered to the skin of the user. Simultaneously, the sensor attached to the plurality of wires 3328 and routed through the needle 3312 is implanted 6 to 10 mm underneath the skin of the user. Due to the bias of the first spring 3360 and the second spring 3362, the needle 3312 automatically retracts from the skin and the plurality of wires 3328 vacate the needle 3312 through the slot 3314 leaving the sensor underneath the skin. The needle 3312 fixed to the plate 3322 moves the distance of the difference between the second uncompressed length and the second compressed length, for example, 12 to 20 mm.

In short, by placing the applicator 3300 on the skin 'as is' and depressing the button 3358 of the actuator 3308, the sensor is implanted underneath the skin and the wearable device 3356 is adhered to the skin. The applicator 3300, the wearable device 3356—including the electronics and the power source—are disposable. The patch 3354 may be comprised of a flexible material such as silicone or urethane, to aid in the removal from the bottom surface 3306 of the body 3302 and also for comfort when adhered to the skin of the user. As shown in FIG. 40B, the tab 3326 is in the open position in the actuator 3300. Once the wearable device 3356 is adhered to the skin, the tab 3326 remains in the open position and may be rotated to the closed position to cover the cutout 3340 in the base 3320 (see FIGS. 35A and 35B). In some embodiments, the contour of the tab 3326 is inserted into the cutout 3340 and the system is sealed and waterproof.

The base 3320 having the circuit board 3330, the microprocessor 3337, each contact of the plurality of contacts 3332 coupled to the wire of the plurality of wires 3328, and the power source 3342 form a sealed unit. Optionally, the transmitter 3339 may also be included in the base. This is possible because the power source 3342 and each contact of the plurality of contacts 3332 coupled to the wire of the plurality of wires 3328, are hardwired to the circuit board 3330 within the base 3320 meaning there is no handoff. For example, the hardwiring occurs during manufacturing without input from the user. In the absence of the handoff, i.e., mechanically and/or electrically connecting the wires for the sensor to the electronics—the circuit board and power source—the system is sealed being robust, reliable and durable. In some embodiments, the base may be coated with a material by a dip or spray of urethanes, silicones or acrylics or a polymer vapor deposition process (parylene C or N) for further protection and benefits such as being impervious to water or waterproof. The sealing and coating may be done at the time of manufacture which enables a reliable process and advanced techniques to be employed while guarantying a sterile environment for the components.

Having the plurality of wires 3328 of the sensor hardwired to base 3320 which becomes part of the wearable device 3356 is a paradigm shift from conventional systems. In conventional systems, the system is designed such that the wires for the sensor are connected mechanically and/or electrically to the electronics e.g., circuit board and power source, at the time of use or application and most likely, with input from the user. This adds a step to the application process and introduces contaminants to the system thus creating a non-sterile environment. The design may be such that the electronics are in the applicator or already mounted on the skin then the wires of the sensor are connected to the electronics. This handoff creates a weakness in conventional designs.

For example, known systems may use an O-ring or gasket to attempt to seal the electronics after the wires of the sensor is connected. As the unit ages, the O-ring or gasket wear and breakdown which becomes a potential entry path for water or debris resulting in failure of the electronics. In contrast, hardwiring the wires for the sensor to the electronics and power source such as during manufacture as in applicator 3300, creates a more securely sealed unit with little risk of mechanical or electrical failure from water or debris. Additionally, in known systems, connecting the sensor to the circuit board and/or power source at the time of application, creates another potential weak link because the integrity of the connection is unknown, a non-sterile environment may be created and is open to user error.

The base 3320 including all the components, the wearable device 3356, the applicator 3300, the needle 3312 and the sensor are designed to be disposable. In conventional systems, the electronics are typically designed to be reused because of the high cost of the components and in the assembly process. In contrast, the applicator 3300 has the plurality of wires 3328 of the sensor hardwired to base 3320 within the body 3302 which uses fewer, inexpensive components and processes such as the fastener 3348 pushed into the opening 334*a/b* as opposed to more expensive components and processes such as soldering, welding or crimping. There is no need to reuse the components.

In further embodiments, various data may be collected through the sensor by the wearable device and managed by the microprocessor 3337. The transmitter 3339 is configured to transmit the data through a communication technology, such as a WiFi system, Bluetooth® wireless technology, Bluetooth® Low Energy, cellular communications, satellite communications or the like, as well as combinations thereof. A device such as a smartphone, computer, router, hub, cellular network transceiver or the like or combinations thereof receives the data.

FIG. 42 is a simplified flowchart for a method 4200 for constructing the base 3320, in accordance with some embodiments. A method 4200 for constructing the base 3320 begins at step 4210 by coupling a sensor to a plurality of wires. The sensor and the plurality of wires are sized to fit through the inner diameter of the needle. At step 4220, a wire of the plurality of wires is coupled to a contact of the plurality of contacts. Each contact has an opening of a plurality of openings on a circuit board and the opening has a metal coating. At step 4230, a fastener having a protrusion is attached into the opening. A diameter of the protrusion is less than a diameter of the opening, and the wire of the plurality of wires is between the opening and the protrusion. At step 4240, a power source is connected to the circuit board. At step 4250, the circuit board and power source are assembled in a base. The base having the circuit board, the microprocessor, the contact of the plurality of contacts coupled to the wire of the plurality of wires, and the power source is a sealed unit. In this way, each contact of the plurality of contacts coupled to the wire of the plurality of wires, and the power source are hardwired to the circuit board of the base. The method 4200 may further include connecting a transmitter to the circuit board before the assembling step. The transmitter is configured to transmit data.

Figure 43:
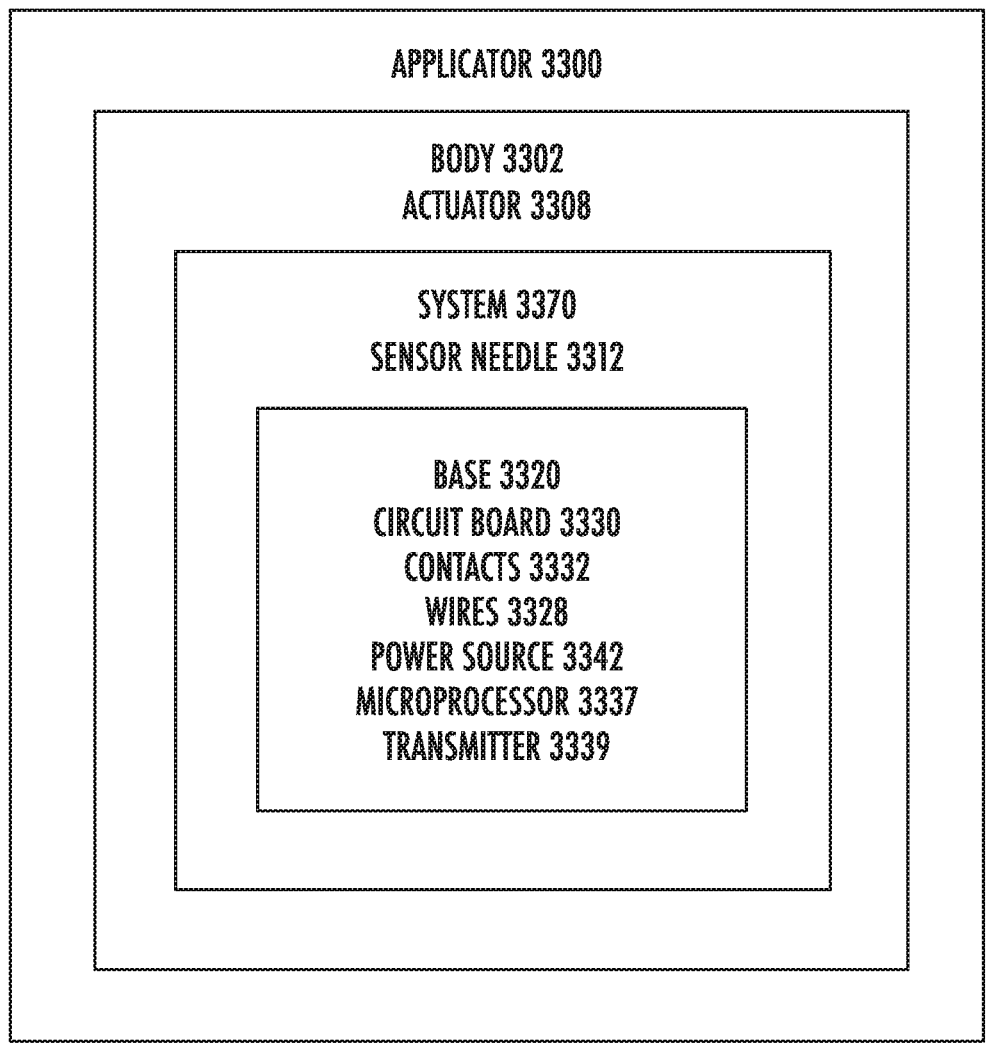
FIG. 43 is a simplified schematic describing the systems in the applicator, in accordance with some embodiments.

The applicator 3300 consists of the three main systems of which the components have been described herein. FIG. 43 is a simplified schematic describing the systems in the applicator 3300, in accordance with some embodiments. The base 3320 includes the circuit board 3330, the plurality of contacts 3332 with the plurality of wires 3328, the power source 3342, the microprocessor 3337 and the transmitter 3339. These components within the base 3320 form a sealed unit.

A system 3370 may include the sensor coupled to a plurality of wires 3328. A base 3320 includes a circuit board 3330 having a microprocessor 3337 electrically connected to the circuit board 3330 and a plurality of contacts 3332. Each contact 3332 is coupled to a wire of the plurality of wires 3328. A power source 3342, such as a battery, is electrically connected to the circuit board 3330 and coupled to the base 3320. A needle 3312 is configured to be moveable through a cutout 3340 on the base 3320. The plurality of wires 3328 extend from the circuit board 3330 of the base 3320, through the needle 3312 and out of the slot 3314 of the needle 3312. As disclosed herein, each contact of the plurality of contacts 3332 coupled to the wire of the plurality of wires 3328 and the power source 3342, are hardwired to the circuit board 3330 of the base 3320. Therefore, the system 3370 includes the sensor, the needle 3312 and the base 3320. The system 3370 may be housed within the applicator 3300 such as in the body 3302.

The body 3302 includes the base 3320, the system 3370 and the actuator 3308 as described herein. In further embodiments, other actuator designs such as a lever or sliding actuator may be used. The applicator 3300 includes the base 3320, the system 3370 and the body 3302.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. An apparatus comprising:
   a body having a bottom surface and a top surface;
   an actuator coupled to the body and extending through the top surface of the body;
   a needle configured to be moveable by the actuator, the needle comprising an inner diameter and a slot along a length of the needle to a tip of the needle;
   a sensor coupled to a plurality of wires, the sensor and the plurality of wires being sized to fit through the inner diameter of the needle;
   a base configured to be moveable by the actuator and comprising:
      a circuit board having a microprocessor electrically connected to the circuit board, and a plurality of contacts, each contact of the plurality of contacts coupled to a respective wire of the plurality of wires, the plurality of wires extending from the circuit board of the base, through the needle and out of the slot of the needle;
      a power source electrically connected to the circuit board and coupled to the base; and
      a cutout configured to allow the needle to pass through;
   a bracket coupled to the bottom surface of the body and configured to receive the base; and
   a patch coupled to the bracket and having an adhesive.

2. The apparatus of claim 1, wherein the each contact comprises:
   an opening of a plurality of openings on the circuit board, the opening of the plurality of openings having a metal coating; and
   a fastener having a protrusion, wherein a diameter of the protrusion is less than a diameter of the opening of the plurality of openings;
   wherein the respective wire of the plurality of wires is between the opening of the plurality of openings and the protrusion.

3. The apparatus of claim 1, wherein the sensor comprises a working electrode and a reference electrode.

4. The apparatus of claim 1, wherein the base having the circuit board, the microprocessor, the each contact of the plurality of contacts coupled to the respective wire of the plurality of wires, and the power source is a sealed unit.

5. The apparatus of claim 1, further comprising:
   a transmitter electrically connected to the circuit board and configured to transmit data.

6. The apparatus of claim 1, wherein:
   the each contact of the plurality of contacts coupled to the respective wire of the plurality of wires, and the power source are hardwired to the circuit board of the base; and
   the sensor, the power source and the circuit board are contained within the body.

7. The apparatus of claim 1, wherein the actuator comprises:
   a spring having an uncompressed length and a compressed length;
   a plate coupled to the spring, the base and the needle;
   wherein the needle moves a distance of a difference between the uncompressed length and the compressed length.

8. The apparatus of claim 1, wherein the base further comprises a tab having an open position and a closed position, and covering the cutout when in the closed position.

9. The apparatus of claim 1, further comprising a cap coupled to the bottom surface of the body and configured to be removable.

10. The apparatus of claim 1, wherein the base and the bracket are comprised of silicone.

11. A system comprising:
    a sensor coupled to a plurality of wires;
    a base comprising:
       a circuit board having a microprocessor electrically connected to the circuit board, and a plurality of contacts, each contact of the plurality of contacts being coupled to a respective wire of the plurality of wires;
       a battery electrically connected to the circuit board and coupled to the base; and
       a cutout;
    a needle configured to be moveable through the cutout on the base, the needle comprising an inner diameter and a slot along a length of the needle to a tip of the needle;
    wherein the sensor and the plurality of wires being sized to fit through the inner diameter of the needle; and
    wherein the plurality of wires extend from the circuit board of the base, through the inner diameter of the needle and out of the slot of the needle.

12. The system of claim 11, wherein the each contact comprises:
    an opening of a plurality of openings on the circuit board, the opening of the plurality of openings having a metal coating; and
    a fastener having a protrusion, wherein a diameter of the protrusion is less than a diameter of the opening of the plurality of openings;
    wherein the respective wire of the plurality of wires is between the opening of the plurality of openings and the protrusion.

13. The system of claim 11, wherein the each contact of the plurality of contacts coupled to the respective wire of the plurality of wires, and a power source are hardwired to the circuit board of the base.

14. The system of claim 11, wherein the base having the circuit board, the microprocessor, the each contact of the plurality of contacts coupled to the respective wire of the plurality of wires, and a power source is a sealed unit.

15. The system of claim 11, further comprising:
    a transmitter electrically connected to the circuit board and configured to transmit data.

16. The system of claim 11, wherein the sensor comprises a working electrode and a reference electrode.

* * * * *